US010851172B2

(12) United States Patent
Oden et al.

(10) Patent No.: US 10,851,172 B2
(45) Date of Patent: Dec. 1, 2020

(54) HUMANIZED ANTIBODIES AGAINST CD269 (BCMA)

(71) Applicant: MAX-DELBRÜCK-CENTRUM FÜR MOLEKULARE MEDIZIN IN DER HELMHOLTZ-GEMEINSCHAFT, Berlin (DE)

(72) Inventors: Felix Oden, Berlin (DE); Stephen Marino, Berlin (DE); Oliver Daumke, Berlin (DE)

(73) Assignee: MAX-DELBRÜCK-CENTRUM FÜR MOLEKULARE MEDIZIN IN DER HELMHOLTZ-GEMEINSCHAFT, Berlin (DE)

(*) Notice: Subject to any disclaimer, the term of this patent is extended or adjusted under 35 U.S.C. 154(b) by 0 days.

(21) Appl. No.: 16/170,575

(22) Filed: Oct. 25, 2018

(65) Prior Publication Data

US 2019/0112382 A1    Apr. 18, 2019

Related U.S. Application Data

(62) Division of application No. 15/306,438, filed as application No. PCT/EP2015/059562 on Apr. 30, 2015, now Pat. No. 10,144,782.

(30) Foreign Application Priority Data

Apr. 30, 2014 (EP) ..................... 14166729

(51) Int. Cl.
C07K 16/28       (2006.01)
C07K 16/30       (2006.01)
A61K 39/395      (2006.01)
A61K 47/68       (2017.01)
A61K 39/00       (2006.01)

(52) U.S. Cl.
CPC ...... *C07K 16/2878* (2013.01); *A61K 47/6849* (2017.08); *A61K 47/6867* (2017.08); *A61K 39/395* (2013.01); *A61K 2039/505* (2013.01); *A61K 2039/545* (2013.01); *C07K 2299/00* (2013.01); *C07K 2317/24* (2013.01); *C07K 2317/33* (2013.01); *C07K 2317/34* (2013.01); *C07K 2317/41* (2013.01); *C07K 2317/54* (2013.01); *C07K 2317/55* (2013.01); *C07K 2317/56* (2013.01); *C07K 2317/565* (2013.01); *C07K 2317/73* (2013.01); *C07K 2317/732* (2013.01); *C07K 2317/76* (2013.01); *C07K 2317/92* (2013.01)

(58) Field of Classification Search
CPC .... C07K 16/28; C07K 16/30; C07K 2317/56; C07K 2317/565; C07K 2317/73; C07K 2317/76; A61K 39/395; A61K 2039/505; A61K 2039/545

See application file for complete search history.

(56) References Cited

U.S. PATENT DOCUMENTS 9,034,324 B2 * 5/2015 Kalled ............... C07K 16/2878
                                                   424/130.1
2003/0012783 A1    1/2003 Kindsvogel
2019/0106499 A1    4/2019 Lipp et al.

FOREIGN PATENT DOCUMENTS

| CN | 101237882 A | 8/2008 |
| CN | 101583626 A | 11/2009 |
| CN | 103562225 A | 2/2014 |
| WO | WO 02/066516 A2 | 8/2002 |
| WO | WO 2010/104949 A2 | 9/2010 |
| WO | WO 2010/115553 A1 | 10/2010 |
| WO | WO 2012/066058 A1 | 5/2012 |
| WO | WO 2012/143498 A1 | 10/2012 |
| WO | WO 2012/163805 A1 | 12/2012 |

OTHER PUBLICATIONS

Bendig, M.M. 1995 "Humanization of rodent monoclonal antibodies by CDR grafting" *Methods: A companion to Methods in Enzymology* 8: 83-93.
Coleman, P.M. 1994 "Effects of amino acid sequence changes on antibody-antigen interactions" *Research in Immunology* 145: 33-36.
Dissertation 2014 "Generation of an antibody targeting B cell maturation antigen for the treatment of multiple myeloma and autoimmune diseases" Retrieved from the Internet at http://www.diss.fu-berlin.de/diss/servlets/MCRFileNodeServlet/FUDISS_derivate_000000016111/Dissertation_FO_ohne.pdf, downloaded Jun. 15, 2015).
GENETEX 2017 "BCMA antibody [Vicky-1]" downloaded from the World-Wide Web at: genetex.com/BCMA-antibody-Vicky-1-GTX17323.html, downloaded Jul. 24, 2017.
Greenspan, N.S. and Di Cera, E. 1999 "Defining epitopes: it's not as easy as it seems" *Nature Biotechnology* 17: 936-937.
Khantasup K. et al. 2015 "Design and generation of humanized single-chain Fv derived from mouse hybridoma for potential targeting application" *Monoclonal Antibodies in Immunodiagnosis and Immunotherapy* 34(6): 404-417.
Paul, W.E. 1993 Fundamental Immunology, 3$^{rd}$ Edition, pp. 292-295, under the header "Fv structure and Diversity in Three Dimensions".
Portolano, S. et al. 1993 "Lack of promiscuity in autoantigen-specific H and L chain combinations as revealed by human H and L chain Roulette" *J Immunol* 150: 880-887.

(Continued)

Primary Examiner — Hong Sang
(74) Attorney, Agent, or Firm — Knobbe, Martens, Olson & Bear, LLP

(57) ABSTRACT

A method of treating a medical disorder associated with the presence of pathogenic B cells expressing B cell maturation antigen (BCMA), the method comprising administering to a subject an isolated antibody or antibody fragment comprising specific VH and VL domain complementary determining region (CDR) sequences, wherein the antibody or fragment thereof specifically binds an epitope of the extracellular domain of CD269 (BCMA).

17 Claims, 20 Drawing Sheets

Specification includes a Sequence Listing.

(56) References Cited

OTHER PUBLICATIONS

R&D Systems 2008 "Monoclonal Anti-human BCMA/TNFRSF17 Antibody" Product Information Sheet (in one page).
R&D Biosystems 2017 "Human BCMA/TNFRSF17 Antibody" downloaded from the World-Wide Web at: rndsystems.com/products/human-bcma-tnfrsf17-antibody-335004_mab193, downloaded Jul. 24, 2017.
Rudikoff S. et al. 1982 "Single amino acid substitution altering antigen-binding specificity" *Proc Natl Acad Sci USA* 79: 1979-1983.
Ryan, M.C. et al. 2007 "Antibody targeting of B-cell maturation antigen on malignant plasma cells" *Molecular Cancer Therapeutics* 6(11): 3009-3018.
Tzartos, S.J. 1996 "Epitope Mapping in antibody competition" in Methods in Molecular Biology, vol. 55, pp. 55-66 (Humana Press Inc, Totowa NJ).
White, CA et al. 2001 "Antibody-targeted immunotherapy for treatment of malignancy" *Annu Rev Med* 52: 125-145.
Caldas, Cristina, et al., "Humanization of the anti-CD18 antibody 6.7: an unexpected effect of a framework residue in binding to antigen," Molecular Immunology 39 (2003) 941-952.
Du, Jiamu, et al., "Molecular Basis of Recognition of Human Osteopontin by 23C3, a Potential Therapeutic Antibody for Treatment of Rheumatoid Arthritis," J. Mol. Biol. (2008) 382, 835-842.
Kunik, Vered, et al., "Structural Consensus among Antibodies Defines the Antigen Binding Site", PLoS Computational Biology, Feb. 2012, vol. 8, Issue 2, e1002388.

\* cited by examiner

Fig. 3
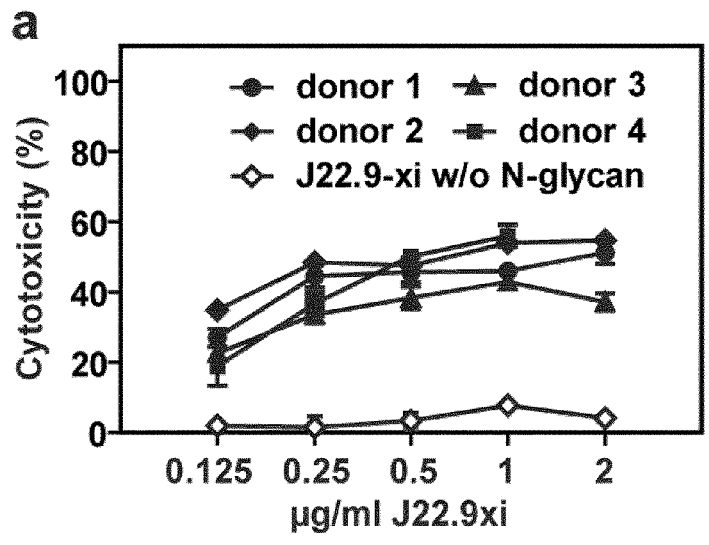
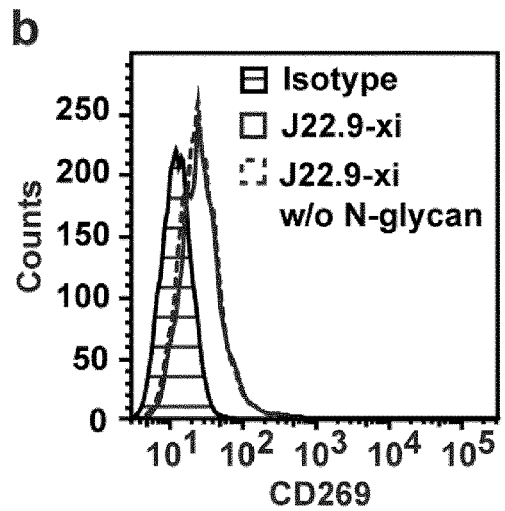
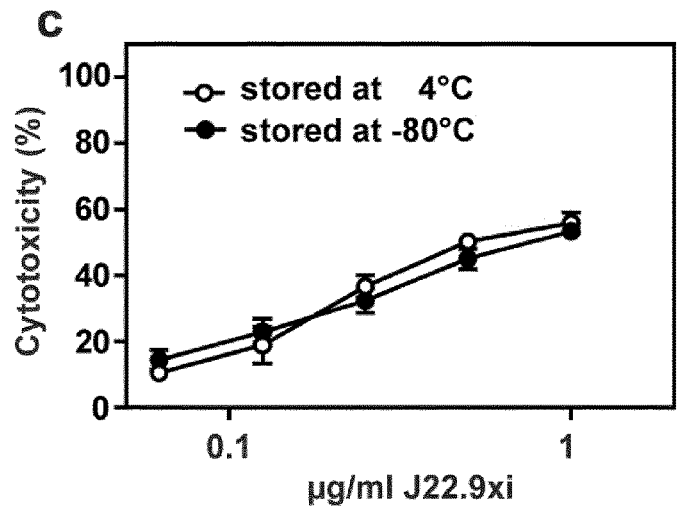

Fig. 4
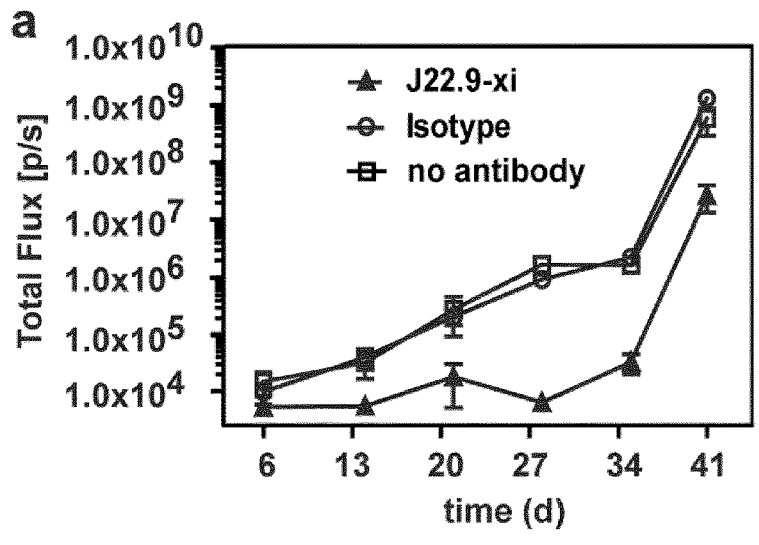
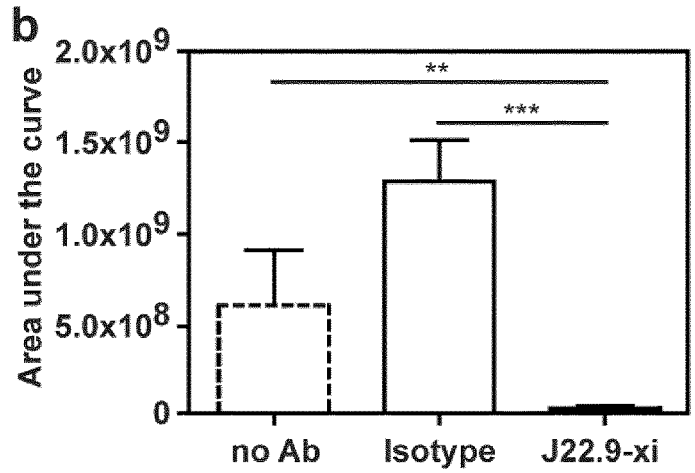
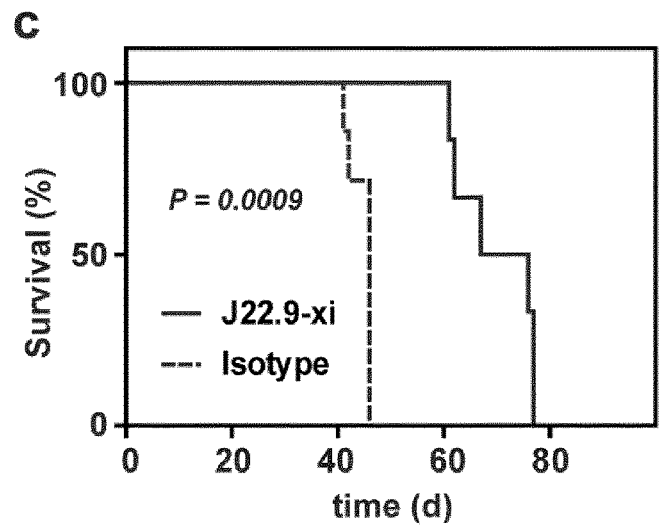

Fig. 4 (cont.)
d-1
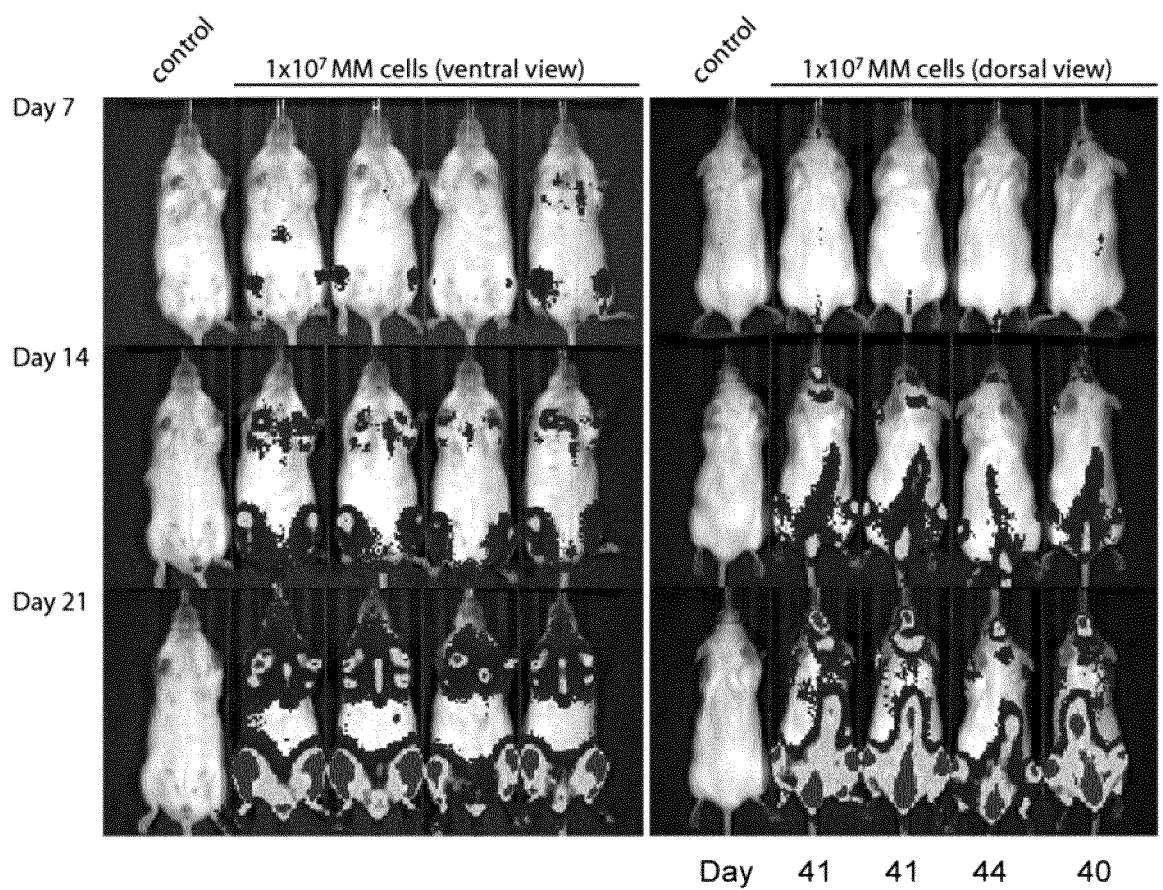
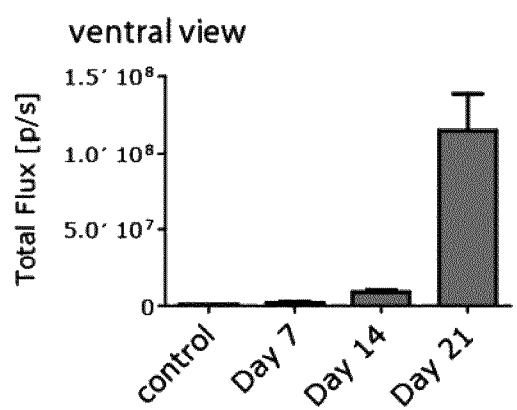
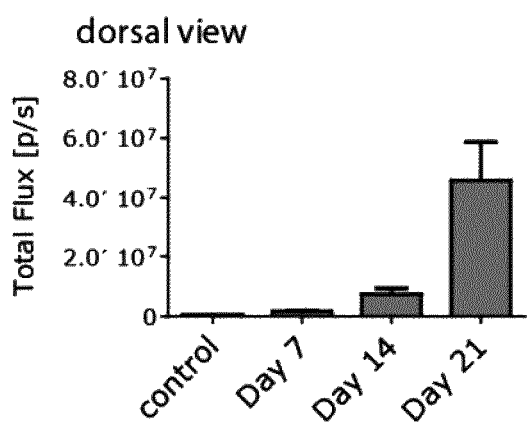

Fig. 4 (cont.)
e
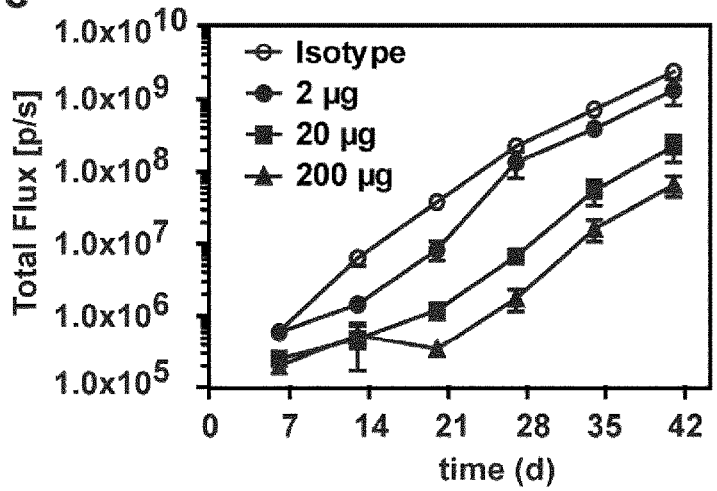
f
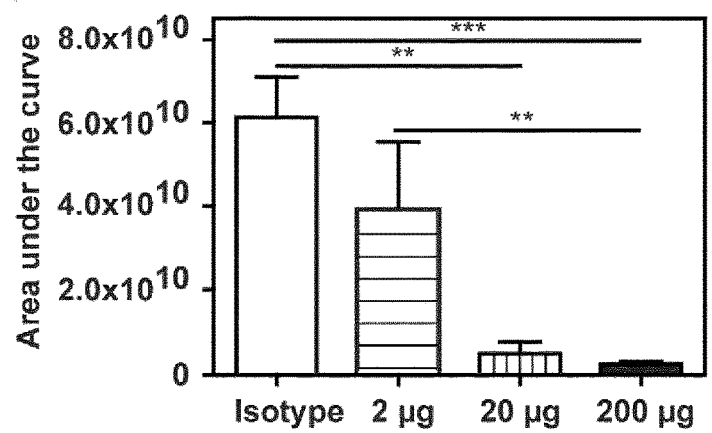
g
Experimental time line
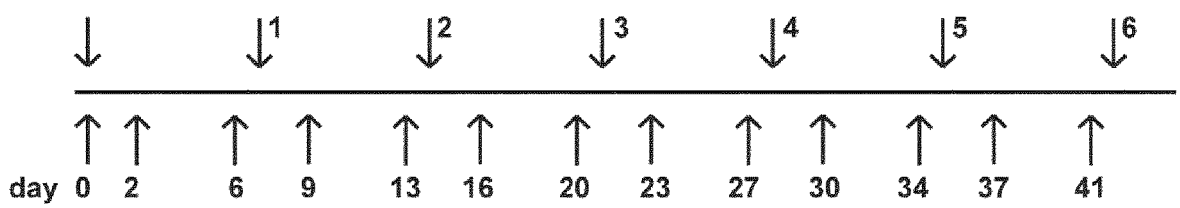

Fig. 5
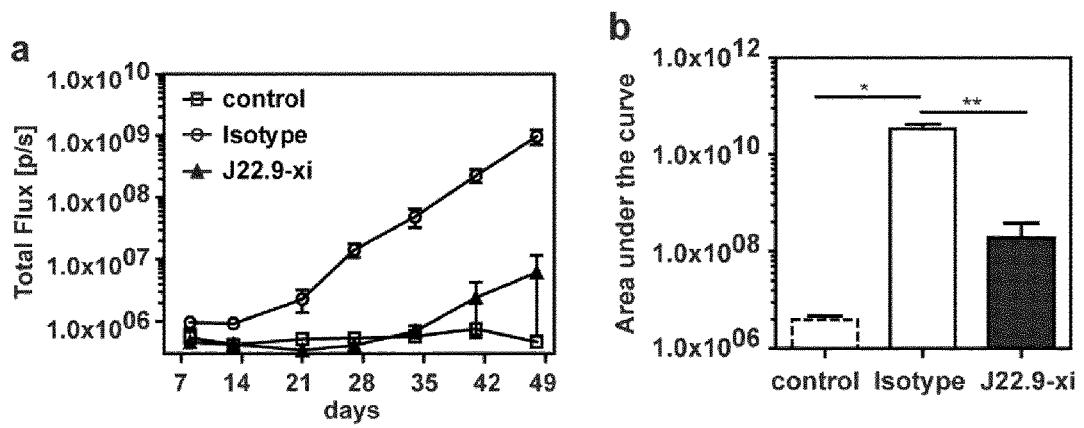
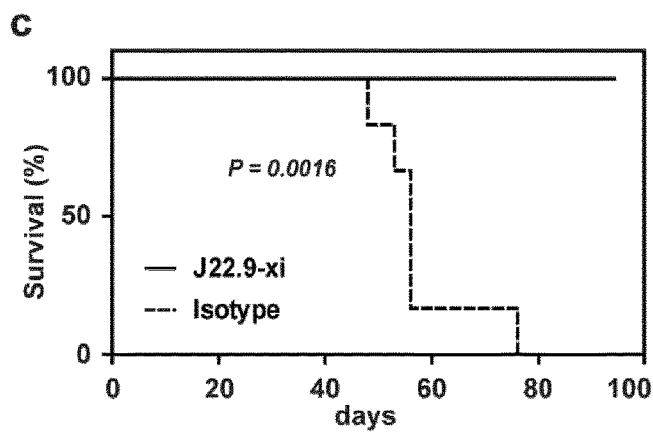
d
Experimental time line
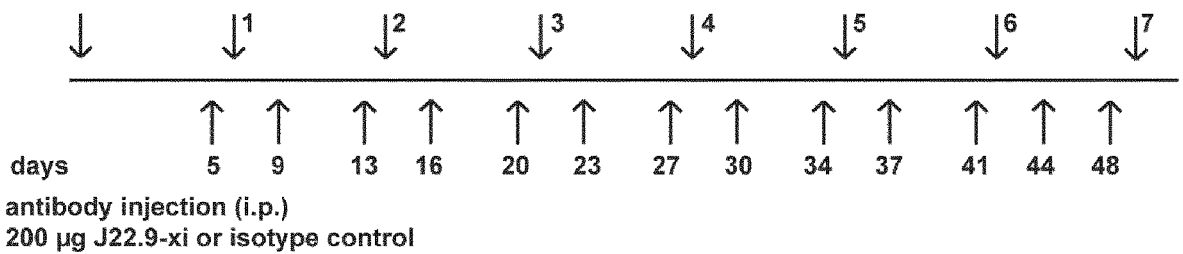

Fig. 6
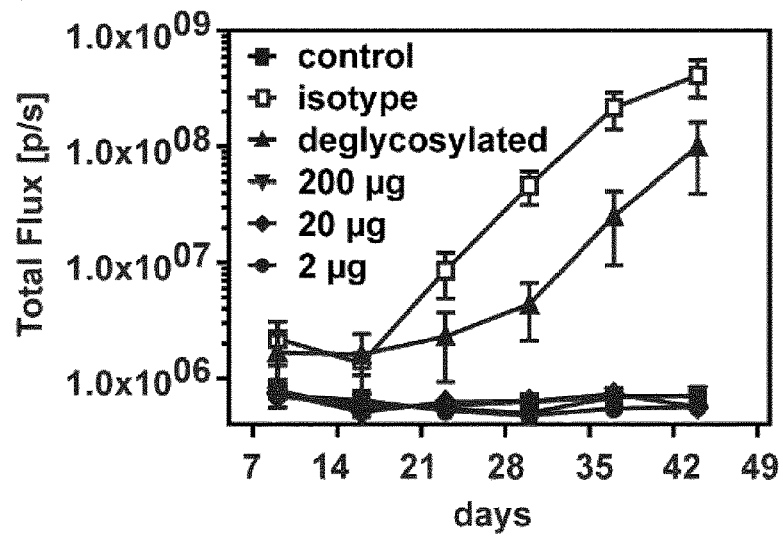
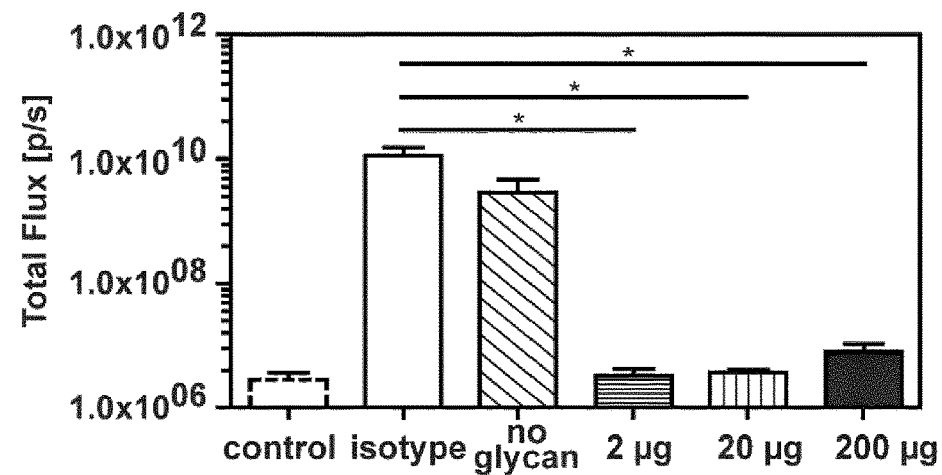
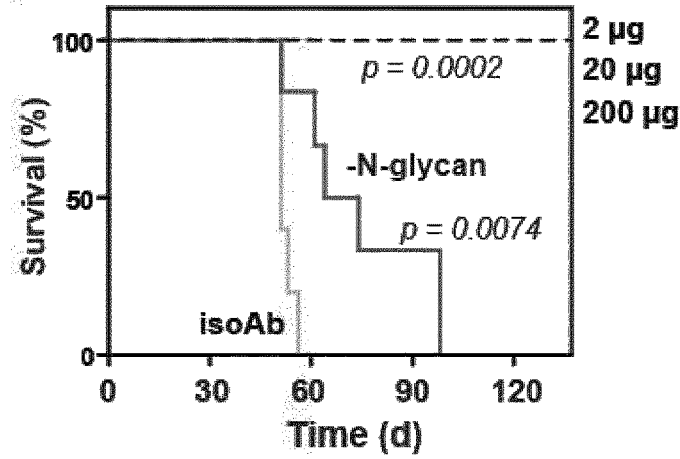

d

Experimental time line

```
         1         10        20        30        40        50
HCg    XVQLXXSGGGLVQPGGSLXLSCAASGXXFXXYXXXWVRXAPGKGLXXXGX
HCm    QVQLQQSGGGLVQPGGSLKLSCAASGIDFSRYWMSWVRRAPGKGLEWIGE
HCpH   EVQLVESGGGLVQPGGSLRLSCAASGFTFDDYWMSWVRQAPGKGLEWVGE
hHC01  EVQLVESGGGLVQPGGSLRLSCAASGFTFSRYWMSWVRQAPGKGLVWVGE
hHC02  EVQLVESGGGLVQPGGSLRLSCAASGFTFSRYWXSWVRQAPGKGLVWVGE
hHC03  EVQLVESGGGLVQPGGSLRLSCAASGFTFSRYXMWVRQAPGKGLVXVGX
hHC04  EVQLVESGGGLVQPGGSLRLSCAASGFTFSRYWISWVRQAPGKGLVWVGE
hHC05  EVQLVESGGGLVQPGGSLRLSCAASGFTFSRYWFSWVRQAPGKGLVWVGE
hHC06  EVQLVESGGGLVQPGGSLRLSCAASGFTFSRYWISWVRQAPGKGLVWVGE
hHC07  EVQLVESGGGLVQPGGSLRLSCAASGFTFSRYWFSWVRQAPGKGLVWVGE 51        60        70        80        90        100
HCg    INPXXSTINYAPSLKXXFXISRDNAKNTLYLQMXXXRSEDTAXYYCASXX
HCm    INPDSSTINYAPSLKDKFIISRDNAKNTLYLQMSKVRSEDTALYYCASLY
HCpH   INPDSSTINYAPSLKGRFTISRDNAKNTLYLQMNSLRAEDTAVYYCASLY
hHC01  INPDSSTINYAPSLKDKFTISRDNAKNTLYLQMNSLRAEDTAVYYCASLY
hHC02  INPXXSTINYAPSLKDKFTISRDNAKNTLYLQMNSLRAEDTAVYYCASLY
hHC03  INPDSSTINYAPSLKDKFTISRDNAKNTLYLQMNSLRAEDTAVYYCASXX
hHC04  INPNSSTINYAPSLKDKFTISRDNAKNTLYLQMNSLRAEDTAVYYCASLY
hHC05  INPNSSTINYAPSLKDKFTISRDNAKNTLYLQMNSLRAEDTAVYYCASLY
hHC06  INPSSSTINYAPSLKDKFTISRDNAKNTLYLQMNSLRAEDTAVYYCASLY
hHC07  INPSSSTINYAPSLKDKFTISRDNAKNTLYLQMNSLRAEDTAVYYCASLY 101       110
HCg    XDYGDXXDYWGQGTXVTVSS
HCm    YDYGDAMDYWGQGTSVTVSS
HCpH   YDYGDAMDYWGQGTLVTVSS
hHC01  YDYGDAMDYWGQGTLVTVSS
hHC02  XDYGDAXDYWGQGTLVTVSS
hHC03  XDYGDXMDYWGQGTLVTVSS
hHC04  YDYGDAYDYWGQGTLVTVSS
hHC05  YDYGDAYDYWGQGTLVTVSS
hHC06  YDYGDAYDYWGQGTLVTVSS
hHC07  YDYGDAYDYWGQGTLVTVSS

X: Variable amino acid according to humanized sequences
HCg: General heavy chain variable sequence
HCm: mouse heavy chain variable sequence
HCpH: partially humanized heavy chain variable sequence
CDRs are underlined in general and mouse sequences.
```

```
            1         10        20        30        40        50
LCg     XIVMTQSXXXXXXXSXGXXVSXXCKASQSVXXXVXWXQQKPXQXPKXLIXX
LCm     DIVMTQSQRFMTTSVGDRVSVTCKASQSVDSNVAWYQQKPRQSPKALIFS
LCpH    DIVMTQSPATLSVSVGDEVTLTCKASQSVDSNVAWYQQKPGQAPKLLIYS
hLC01   EIVMTQSPATLSVSPGERATLSCKASQSVDSNVAWYQQKPGQAPRALIYS
hLC02   EIVMTQSPATLSVSPGERATLSCKASQSVXXNVAWYQQKPGQAPRALIYS
hLC03   EIVMTQSPATLSVSPGERATLSCKASQSVDXXVXWXQQKPGQAPRALIXX
hLC04   EIVMTQSPATLSVSPGERATLSCKASQSVESNVAWYQQKPGQAPRALIYS 51        60        70        80        90        100
LCg     XXXRXSGXPARFXGSXXGTXFTLTISXLQSEDXAXYXCXQXNNXPXTFGA
LCm     ASLRFSGVPARFTGSGSGTDFTLTISNLQSEDLAEYFCQQYNNYPLTFGA
LCpH    DDLRFSGVPARFSGSGSGTDFTLTISSLQSEDFAVYYCQQYNNYPLTFGA
hLC01   ASLRFSGIPARFSGSGSGTEFTLTISSLQSEDFAVYYCQQYNNYPLTFGA
hLC02   ASLRFSGIPARFSGSGSGTEFTLTISSLQSEDFAVYYCQQYNNYPLTFGA
hLC03   AXXRXSGIPARFSGSXXGTEFTLTISSLQSEDFAVYYCXQXNNXPXTFGA
hLC04   ASLRFSGIPARFSGSGSGTEFTLTISSLQSEDFAVYYCQQYNNYPLTFGA

101
LCg     GTKLELKR
LCm     GTKLELKR
LCpH    GTKLELKR
hLC01   GTKLELKR
hLC02   GTKLELKR
hLC03   GTKLELKR
hLC04   GTKLELKR
```

```
X: Variable amino acid according to either mouse or humanized
sequences
LCg: General heavy chain variable sequence
LCm: mouse heavy chain variable sequence
LCpH: partially humanized heavy chain variable sequence
CDRs are underlined in general and mouse sequences.
```

Fig. 10
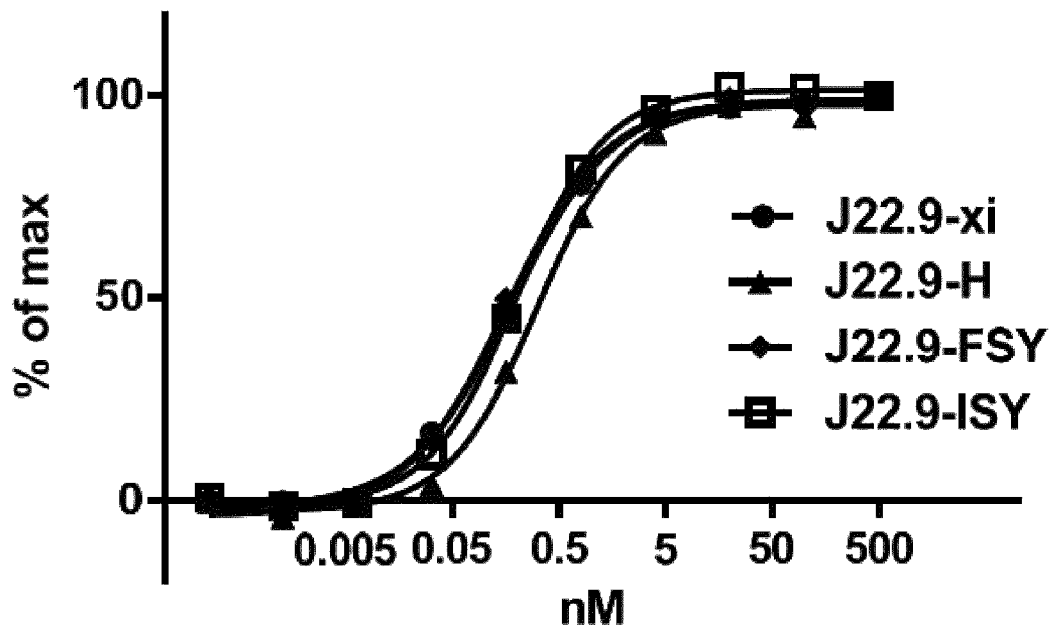
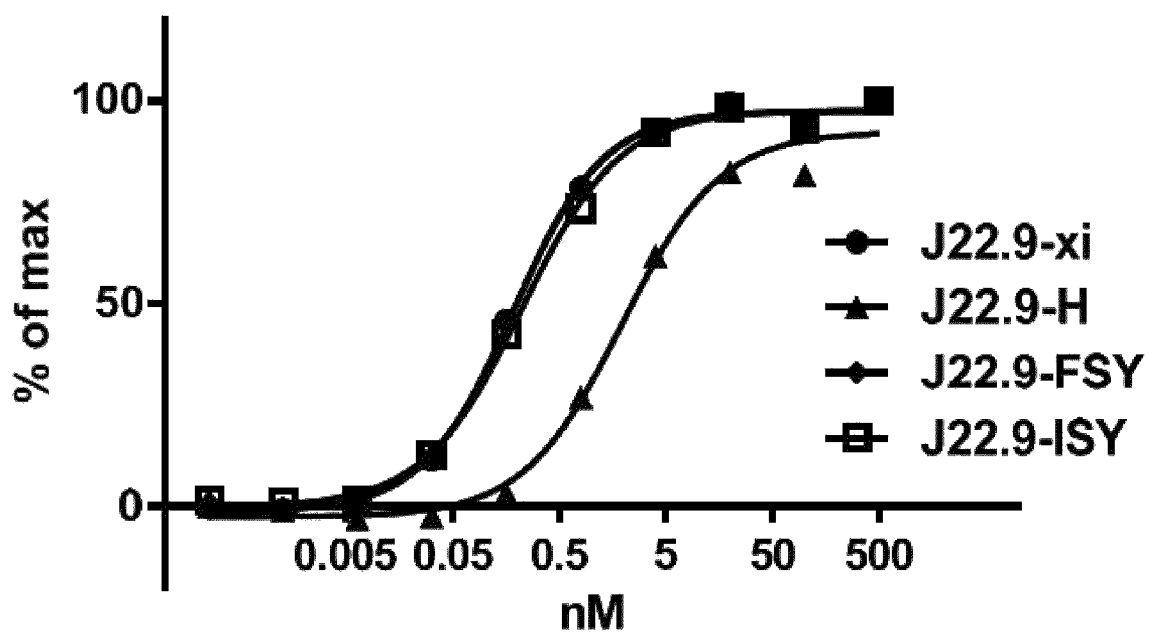

A (continued)

B (continued)

HUMANIZED ANTIBODIES AGAINST CD269 (BCMA)

The invention relates to humanized antibodies or antibody fragments that bind CD269 (BCMA), thereby disrupting the interaction between CD269 and its native ligands (BAFF and APRIL), and their use in the treatment of plasma cell-mediated diseases such as multiple myeloma and autoimmune diseases.

REFERENCE TO SEQUENCE LISTING

A Sequence Listing submitted as an ASCII text file via EFS-Web is hereby incorporated by reference in accordance with 35 U.S.C. § 1.52(e). The name of the ASCII text file for the Sequence Listing is 29276125_1. TXT, the date of creation of the ASCII text file is Oct. 25, 2018, and the size of the ASCII text file is 53.8 KB.

BACKGROUND OF THE INVENTION

The B cell maturation antigen (BCMA) is member 17 of the tumor necrosis factor receptor superfamily (TNFRSF). Its native ligands are the B cell activating factor (BAFF; also called BLyS or TALL-1, TNFSF13B) and a proliferation-inducing ligand (APRIL, TNFSF13, CD256) which are involved (through interaction with further ligands) in regulating various aspects of humoral immunity, B cell development, and homeostasis.

BCMA is highly expressed on malignant plasma cells, for example in multiple myeloma, (MM), which is a B cell non-Hodgkin lymphoma of the bone marrow, and plasma cell leukemia (PCL), which is more aggressive than MM and constitutes around 4% of all cases of plasma cell disorders. In addition to MM and PCL, BCMA has also been detected on Hodgkin and Reed-Sternberg cells in patients suffering from Hodgkin's lymphoma (Chiu et al. (2007) Blood 109: 729-739). Similar to its function on plasma cells, ligand binding to BCMA has been shown to modulate the growth and survival of multiple myeloma cells expressing BCMA (Novak et al. (2004) Blood 103:689-694). Signalling of BAFF and APRIL via BCMA are considered as pro-survival factors for malignant plasma cells; hence, the depletion of BCMA-positive tumour cells and/or the disruption of ligand-receptor interaction should improve the therapeutic outcome for multiple myeloma and autoantibody-dependent autoimmune diseases.

There are presently various approaches available for the treatment of multiple myeloma (Raab et al. (2009) Lancet 374:324-339). Chemotherapy leads in most subjects only to partial control of multiple myeloma; only rarely does chemotherapy lead to complete remission. Combination approaches are therefore often applied, commonly involving an additional administration of corticosteroids, such as dexamethasone or prednisone. Corticosteroids are however plagued by side effects, such as reduced bone density. Stem cell transplantation has also been proposed, using one's own stem cells (autologous) or using cells from a close relative or matched unrelated donor (allogeneic). In multiple myeloma, most transplants performed are of the autologous kind. Such transplants, although not curative, have been shown to prolong life in selected patients (Suzuki (2013) Jpn J Clin Oncol 43:116-124). Alternatively thalidomide and derivatives thereof have recently been applied in treatment but are also associated with sub-optimal success rates and high costs. More recently, the proteasome inhibitor bortezomib (PS-341) has been approved for the treatment of relapsed and refractory MM and was used in numerous clinical trials alone or in combination with established drugs resulting in an encouraging clinical outcome (Richardson et al. (2003) New Engl J Med 348:2609-2617; Kapoor et al. (2012) Semin Hematol 49:228-242). The costs for combined treatments are correspondingly high and success rates still leave significant room for improvement. The combination of treatment options is also not ideal due to an accumulation of side effects if multiple medicaments are used simultaneously. Novel approaches for the treatment of plasma cell diseases, in particular multiple myeloma, are required.

The ability to specifically target plasma cells is also of great benefit for the treatment of autoimmune diseases. Mild forms of autoimmune disease are usually initially treated with nonsteroidal anti-inflammatory drugs (NSAID) or disease-modifying anti-rheumatic drugs (DMARD). More severe forms of Systemic Lupus Erythematosus (SLE), involving organ dysfunction due to active disease, usually are treated with steroids in conjunction with strong immunosuppressive agents such as cyclophosphamide, a cytotoxic agent that targets cycling cells. Only recently Belimumab, an antibody targeting the cytokine BAFF, which is found at elevated levels in serum of patients with autoimmune diseases, received approval by the Food and Drug Administration (FDA) for its use in SLE. However, only newly formed B cells rely on BAFF for survival in humans, whereas memory B cells and plasma cells are less susceptible to selective BAFF inhibition (Jacobi et al. (2010) Arthritis Rheum 62:201-210). For rheumatoid arthritis (RA), TNF inhibitors were the first licensed biological agents, followed by abatacept, rituximab, and tocilizumab and others: they suppress key inflammatory pathways involved in joint inflammation and destruction, which, however, comes at the price of an elevated infection risk due to relative immunosuppression (Chan et al. (2010) Nat Rev Immunol 10:301-316, Keyser (2011) Curr Rheumatol Rev 7:77-87). Despite the approval of these biologicals, patients suffering from RA and SLE often show a persistence of autoimmune markers, which is most likely related to the presence of long-lived, sessile plasma cells in bone marrow that resist e.g. CD20-mediated ablation by rituximab and high dosage glucocorticoid and cyclophosphamid therapy.

Antibodies which bind CD269 (BCMA) and their use in the treatment of various B-cell related medical disorders have been described in the art. Ryan et al (Molecular Cancer Therapeutics, 2007 6(11), 3009) describe an anti-BCMA antibody obtained via vaccination in rats using a peptide of amino acids 5 to 54 of the BCMA protein. WO 2012/163805 describes BCMA binding proteins, such as chimeric and humanized antibodies, their use to block BAFF and/or APRIL interaction with BCMA and their potential use in treating plasma cell malignancies such as multiple myeloma. The antibody disclosed therein was obtained via vaccination in mouse using a recombinant peptide of amino acids 4 to 53 of the BCMA protein. WO 2010/104949 also discloses various antibodies that bind preferably the extracellular domain of BCMA and their use in treating B cell mediated medical conditions and disorders. WO 2002/066516 and WO 2012/066058 disclose bivalent antibodies that bind both BCMA and additional targets and their potential use in the treatment of B cell related medical disorders. Details regarding the binding properties and specific epitopes of the bivalent antibodies are not provided in either disclosure.

SUMMARY OF THE INVENTION

In light of the prior art the technical problem underlying the invention was the provision of an agent suitable for treating human diseases associated with pathogenic plasma cells, such as multiple myeloma and autoimmune diseases. This problem is solved by the features of the independent claims. Preferred embodiments of the present invention are provided by the dependent claims.

Therefore, an object of the invention is to provide a humanized antibody or antibody fragment that binds CD269 (BCMA), in particular an epitope of the extracellular domain of CD269 (BCMA).

The antibodies disclosed herein comprise humanized sequences, especially of the preferred VL and VH binding regions, which maintain the appropriate ligand affinities as described with respect to the chimeric antibody J22.9-xi.

In various embodiments of the invention the amino acid sequence modification to obtain said humanized sequences may occur in either the CDR regions of the original chimeric antibody J22.9-xi or in the framework regions, wherein the framework region is to be understood as a region in the variable domain of a protein which belongs to the immunoglobulin superfamily, and which is less "variable" than the CDRs.

It was entirely surprising that the particular humanized sequences provided herein, preferably the CDR regions of the VL and VH regions involved in binding, exhibit the specific and strong binding as demonstrated in the experimental examples, and maintain the binding characteristics of the original chimeric antibody J22.9-xi to such an extent as to maintain their desired therapeutic effect.

The invention therefore relates to an antibody or antibody fragment, comprising a VH domain that comprises CDR sequences of:

RYWX$_1$S,  (H-CDR1; SEQ ID NO. 15)

wherein X$_1$: I, F, L, V, Y. C, G, A, S, T);

EINPX$_2$X$_3$STINYAPSLKDK,  (H-CDR2; SEQ ID No. 16)

wherein X$_2$X$_3$: SS, NS, TS, GS, KS, RS, SD, SN, DE; and/or

SLYX$_4$DYGDAX$_5$DYW,  (H-CDR3; SEQ ID NO. 17)

wherein X$_4$: Y, L, A, V, F, I, W, and/or X$_5$: Y, L, F, I, V, A, C, wherein said antibody or fragment thereof specifically binds an epitope of the extracellular domain of CD269 (BCMA).

It was particularly surprising that the humanized antibodies described herein, that exhibit sequence changes compared to the original chimeric antibody, in particular sequence changes in the CDRs of said chimeric antibody, maintain sufficient binding properties towards their target for therapeutic efficacy.

A skilled person would not have expected that the binding characteristics of the humanized variants would be similar to the original chimeric or mouse antibody. Considering the sequence changes in the variable domains, in particular the CDRs, the beneficial binding characteristics of the humanized sequences demonstrated herein are considered a surprising technical effect. The comparison in binding characteristics between the partially and fully humanized antibodies also shows improvements in the fully humanized sequences. This represents an entirely unexpected result. The initial modifications to the chimera (partially human-ized) led to some loss in binding affinity. However, the introduction of further humanizations subsequently lead to enhanced binding, whereby the "fully humanized" sequences show similar binding properties compared to the original chimera, thereby showing a surprising technical effect after having made such significant sequence modifications without severe loss of binding affinity.

In a preferred embodiment the antibody or antibody fragment as described herein is characterised in that the VH domain comprises the CDR sequence RYWIS (SEQ ID NO. 18) or RYWFS (SEQ ID NO. 19).

In a preferred embodiment the antibody or antibody fragment as described herein is characterised in that said VH domain comprises the CDR sequence EINPNSSTINY-APSLKDK (SEQ ID No. 20) or EINPSSSTINYAPSLKDK (SEQ ID No. 21).

In further embodiments of the invention amino acid 54 of the VH domain may relate to any given amino acid or modified amino acid. As shown in the examples below, potential glycosylation of the N amino acid at this residue does not significantly disrupt specific and strong binding of the antibody to the target epitope. In light of this information, the invention relates to an antibody or antibody fragment comprising an CDR2 sequence as described herein, wherein any given amino acid or modified amino acid may be present at amino acid 54 of the VH domain in the CDR2 sequence.

In a preferred embodiment the antibody or antibody fragment as described herein is characterised in that said VH domain comprises the CDR sequence SLYYDYGDAY-DYW (SEQ ID NO. 22).

The invention further relates to an antibody or antibody fragment, comprising a VL domain that comprises CDR sequences of:

KASQSVX$_1$X$_2$NVA,  (L-CDR1; SEQ ID NO. 23)

wherein X$_1$X$_2$: ES, SS, TS, QS, HS, DH;

SASLRFS;  (L-CDR2; SEQ ID NO 24)
and/or

QQYNNYPLTFG,  (L-CDR3; SEQ ID NO. 25)

wherein said antibody or fragment thereof specifically binds an epitope of the extracellular domain of CD269 (BCMA).

Also with respect to the LC sequence, it was surprising that the modified sequence of the CDR3 sequence had no significant detrimental effect on binding to the BCMA target.

Furthermore, antibodies of the present invention also show unexpected and beneficial stability characteristics when in solution, both when isolated or purified, or in vitro, and in vivo, post administration, that would not have been expected from the sequence changes carried out to the original chimeric antibody.

In a preferred embodiment the antibody or antibody fragment as described herein is characterised in that the VL domain comprises the CDR sequence KASQSVDSNVA (SEQ ID NO. 26).

In a preferred embodiment the antibody or antibody fragment as described herein comprises a VH domain that comprises the sequence EVQLVESGGGLVQPG-GSLRLSCAASGFTFSRYWX$_1$SWVRQAPGKGLVWV-GEINPX$_2$X$_3$STIN YAPSLKDKFTISRDNAKNTLYL-QMNSLRAEDTAVYYCASLYX$_4$DYGDAX$_5$DYWGQ- GTLVTVSS (SEQ ID NO. 4), wherein $X_1$: I, F, L, V, Y, C, G, A, S, T; $X_2X_3$: SS, NS, TS, GS, KS, RS, SD, SN, DE, preferably SS; $X_4$: Y, L, A, V, F, I, W; and $X_5$: Y, L, F, I, V, A, C.

In a preferred embodiment the antibody or antibody fragment as described herein is characterised in that the antibody or fragment comprises a VH domain that comprises the sequence according to SEQ ID NO. 6, SEQ ID NO. 7, SEQ ID NO. 8 or SEQ ID NO. 9.

In a preferred embodiment the antibody or antibody fragment as described herein comprises a VL domain that comprises the sequence EIVMTQS-PATLSVSPGERATLSCKASQSVX$_1$X$_2$NVAWYQQKP-GQAPRALIYSASLRFSGIPAR FSGSGSGTEFTLTISS-LQSEDFAVYYCQQYNNYPLTFGAGTKLELKR (SEQ ID NO. 12), wherein $X_1X_2$: ES, SS, TS, QS, HS, DH.

In a preferred embodiment the antibody or antibody fragment as described herein comprises a VL domain that comprises the sequence according to SEQ ID NO. 14.

In a preferred embodiment the antibody or antibody fragment as described herein comprises a VH domain that comprises the sequence according to SEQ ID NO. 6, SEQ ID NO. 7, SEQ ID NO. 8 or SEQ ID NO. 9 and a VL domain that comprises the sequence according to SEQ ID NO. 14.

The invention further relates to an antibody or antibody fragment as described herein comprising a VH domain, wherein said VH domain comprises a sequence according to X$_1$VQLX$_2$X$_3$SGGGLVQPGGSLX$_4$LSCAASGX$_5$X$_6$F-X$_7$X$_8$YWZ$_1$ SWVRX$_9$APGKGLEWX$_{10}$GEI-NPZ$_2$SSTINYAPSLKX$_{11}$X$_{12}$FX$_{13}$I SRDNAKNTLYLQMX$_{14}$X$_{15}$X$_{16}$RX$_{17}$EDTAX$_{18}$YYC-ASLYYDYGDAZ$_3$DYWGQGTX$_{19}$VTVSS (SEQ ID No. 41), wherein $X_1$: Q, E; $X_2$: Q, V; $X_3$: Q, E; $X_4$: K, R; $X_5$: I, F; $X_6$: D, T; $X_7$: S, D; $X_8$: R, D; $X_9$: R, Q; $X_{10}$: I, V; $X_{11}$: D, G; $X_{12}$: K, R; $X_{13}$: I, T; $X_{14}$: S, N; $X_{15}$: K, S; $X_{16}$: V, L; $X_{17}$: S, A; $X_{18}$: L, V; $X_{19}$: S, L; and wherein at least one of $Z_1$: I, F, L, V, Y, C, G, A, S, T, preferably I or F; $Z_2$: S, N, T, G, K, R, D, preferably S and/or $Z_3$: Y, L, F, I, V, A, C, preferably Y; and wherein said antibody or fragment thereof specifically binds an epitope of the extracellular domain of CD269 (BCMA).

This embodiment encompasses various humanized antibodies, in particular the VH sequences thereof, all variants defined by the advantageous humanization carried out in the CDRs as described herein.

The invention further relates to an antibody or antibody fragment as described herein comprising a VL domain, wherein said VL domain comprises a sequence according to DIVMTQSX$_1$X$_2$X$_3$X$_4$X$_5$X$_6$SVGDX$_7$VX$_8$X$_9$TCKASQS-VESNVAWYQQKPX$_{10}$QX$_{11}$PKX$_{12}$LIX$_{13}$SX$_{14}$X$_{15}$LRFS-GVPARFX$_{16}$GSGSGTDFTLTISX$_{17}$LQSEDX$_{18}$AX$_{19}$Y-X$_{20}$CQQYNNYPLTFGAGTKLELK R (SEQ ID No. 42), wherein $X_1$: Q, P; $X_2$: R, A; $X_3$: F, T; $X_4$: M, L; $X_5$: T, S; $X_6$: T, V; $X_7$: R, E; $X_8$: S, T; $X_9$: V, L; $X_{10}$: R, G; $X_{11}$: S, A; $X_{12}$: A, L; $X_{13}$: F, Y; $X_{14}$: A, D; $X_{15}$: S, D; $X_{16}$: T, S; $X_{17}$: N, S; $X_{18}$: L, F; $X_{19}$: E, V; $X_{20}$: F, Y; and wherein said antibody or fragment thereof specifically binds an epitope of the extracellular domain of CD269 (BCMA). This embodiment encompasses various humanized antibodies, in particular the VL sequences thereof, all variants defined by the advantageous humanization carried out in the CDRs as described herein.

Preferred Embodiments Regarding Humanized Antibody Variants

As disclosed in detail herein, the sequence of the preferred embodiments of the invention according to J22.9-xi was humanized in order to provide a more compatible reagent for administration in human subjects. Various humanized sequence variants of J22.9-xi have been generated and tested for their binding affinity and specificity to both human and cynomolgus CD269 (BCMA). The results from binding assays demonstrate that the humanized sequences maintain the desired binding properties of the chimeric reagent J22.9-xi. In the below sequences the underlined regions represent the CDRs or putative CDRs.

Preferred Embodiments Regarding Humanized VH Variants

Additional information is provided below on the humanized antibody sequence of the present invention.

Chimeric Sequence:

```
HC mouse (SEQ ID No. 1):
QVQLQQSGGGLVQPGGSLKLSCAASGIDFSRYWMSWVRRAPGKGLEWIGE

INPDSSTINYAPSLKDKFIISRDNAKNTLYLQMSKVRSEDTALYYCASLY

YDYGDAMDYWGQGTSVTVSS
```

The HC mouse sequence represents the variable region of the heavy chain (VH) originally developed for the chimeric antibody J22.9-xi, which comprises VL and VH domains obtained from a mouse antibody, capable of binding an epitope of the extracellular domain of CD269 (BCMA), and the VL and VH domains are fused to human CL and CH domains, respectively.

Partially Humanized Sequences:

```
HC partially humanized (SEQ ID No. 2):
EVQLVESGGGLVQPGGSLRLSCAASGFTFDDYWMSWVRQAPGKGLEWVGE

INPDSSTINYAPSLKGRFTISRDNAKNTLYLQMNSLRAEDTAVYYCASLY

YDYGDAMDYWGQGTLVTVSS
```

The HC partially humanized sequence represents a modified amino acid sequence (via amino acid substitutions) in comparison to the chimeric antibody disclosed herein, whereby the VL and VH binding regions have been modified with respect to their sequence to make them more suitable for administration in humans.

Humanized VH Sequence:

```
hHC01 (SEQ ID No. 3)
EVQLVESGGGLVQPGGSLRLSCAASGFTFSRYWMSWVRQAPGKGLVWVGE

INPDSSTINYAPSLKDKFTISRDNAKNTLYLQMNSLRAEDTAVYYCASLY

YDYGDAMDYWGQGTLVTVSS
```

Humanized VH Sequence with Removal of Post Translational Modification Motifs:

```
hHC02 (SEQ ID No. 4)
EVQLVESGGGLVQPGGSLRLSCAASGFTFSRYWX1SWVRQAPGKGLVWVG

EINPX2X3STINYAPSLKDKFTISRDNAKNTLYLQMNSLRAEDTAVYYCA

SLYX4DYGDAX5DYWGQGTLVTVSS
```

Wherein:
$X_1$: I, F, L, V, Y, C, G, A, S, T, preferably I or F;
$X_2X_3$: SS, NS, TS, GS, KS, RS, SD, SN, DE, preferably SS;
$X_4$: Y, L, A, V, F, I, W, preferably Y; and/or
$X_5$: Y, L, F, I, V, A, C, preferably Y;

The "hHC01" and "hHC02" humanized sequences represent novel amino acid sequences that comprise sequence changes in comparison to both the original chimeric sequence and the partially humanized sequences described herein.

The PTM mutations are intended to remove potentially detrimental post translational modification motifs from said proteins, whilst maintaining the advantageous binding properties. The positions 1, 5, 6, 19, 27, 28, 34, 39, 46, 48, 54, 69, 84, 85, 86, 88, 93, 107 and/or 115 of hHC01 and hHC02 are preferably mutated (substituted) in comparison to the original chimeric sequence. The importance of the substitution relates primarily to the resulting amino acid, not the originating amino acid. The change may therefore also be carried out from the corresponding amino acid of the original chimeric amino acid or other variant, such as the partially humanized sequences.

The following substitutions are novel in comparison to the chimeric (SEQ ID No 1) sequence:
- the amino acid M34 of the HC (VH) sequence is substituted with any amino acid, preferably I, L, F, V, Y. C, G, A, S, T;
- the amino acid E46 of the HC (VH) sequence is substituted with V;
- the amino acids D54 and S55 of the HC (VH) sequence is substituted with any amino acid combination, preferably SS, TS, GS, KS, RS, SD, SN, DE;
- the amino acid Y101 of the HC (VH) sequence is substituted with any amino acid, preferably L, A, V, F, I, W; and/or
- the amino acid M107 of the HC (VH) sequence is substituted with any amino acid, preferably L, Y, F, I, V, A, C.

Sequences that May be Modified at Those Residues Required for Direct Interaction with BCMA:

hHC03 - modified amino acids involved in interaction with BCMA (SEQ ID No 5):
EVQLVESGGGLVQPGGSLRLSCAASGFTFSRY$X_1$M$X_2$WVRQAPGKGLV$X_3$

VG$X_4$INPDSSTINYAPSLKDKFTISRDNAKNTLYLQMNSLRAEDTAVYYC

AS$X_5X_6X_7$DYGD$X_8$MDYWGQGTLVTVSS

Wherein preferred amino acids are:
$X_1$: W, F, Y, preferred W;
$X_2$: S, T, N, Q, D, E, preferred S;
$X_3$: W, F, Y, preferred W;
$X_4$: E, Q, preferred E;
$X_5$: L, I, V, G, A, preferred L;
$X_6$: Y, X, preferred Y;
$X_7$: Y, F, L, I, V, M, preferred Y; and/or
$X_8$: A, G, V, preferred A.

The "hHC03" humanized sequence represents novel amino acid sequences that comprise amino acid sequence changes in comparison to both the original chimeric sequence and the partially humanized sequence. These sequence changes are intended to reflect potential changes in the amino acids that bind the BCMA target, which may be substituted, whilst maintaining the advantageous binding properties. The importance of the substitution relates primarily to the resulting amino acid, not the originating amino acid. The change may therefore also be carried out from the corresponding amino acid of the original chimeric amino acid or other variant.

For example:
- the amino acid W33 of the HC (VH) sequence is W, F, Y;
- the amino acid S35 of the HC (VH) sequence is S, T, N, Q, D, E;
- the amino acid W47 of the HC (VH) sequence is W, F, Y;
- the amino acid E50 of the HC (VH) sequence is E, Q;
- the amino acid L99 of the HC (VH) sequence is L, I, V, G, A;
- the amino acid Y100 of the HC (VH) sequence is Y, X;
- the amino acid Y101 of the HC (VH) sequence is Y, F, L, I, V, M; and/or
- the amino acid A106 of the HC (VH) sequence is A, G, V.

In general, any change to a CDR region made during humanization may also be considered as a feature of a CDR sequence when considered independently of the framework sequence as a whole. Such modified CDR sequences may be considered defining features of the present invention, either within or independent of their context in the entire framework region described herein. For example, the CDR sequences identified by underline in the hHC01 to hHC03 may be considered a defining feature of the invention independently of the surrounding framework sequence.

Specific Examples of Humanized HC (VH) Sequences:

hHC04 (SEQ ID NO 6):
EVQLVESGGGLVQPGGSLRLSCAASGFTFS<u>RYWIS</u>WVRQAPGKGLVWVGE

<u>INPNSSTINYAPSLKDKFTISRDNAKNTLYLQMNSLRAEDTAVYYCASLY</u>

<u>YDYGDAYDYW</u>GQGTLVTVSS hHC05 (SEQ ID NO 7):
EVQLVESGGGLVQPGGSLRLSCAASGFTFS<u>RYWFS</u>WVRQAPGKGLVWVGE

<u>INPNSSTINYAPSLKDKFTISRDNAKNTLYLQMNSLRAEDTAVYYCASLY</u>

<u>YDYGDAYDYW</u>GQGTLVTVSS hHC06 (SEQ ID NO 8):
EVQLVESGGGLVQPGGSLRLSCAASGFTFS<u>RYWIS</u>WVRQAPGKGLVWVGE

<u>INPSSSTINYAPSLKDKFTISRDNAKNTLYLQMNSLRAEDTAVYYCASLY</u>

<u>YDYGDAYDYW</u>GQGTLVTVSS hHC07 (SEQ ID NO 9):
EVQLVESGGGLVQPGGSLRLSCAASGFTFS<u>RYWFS</u>WVRQAPGKGLVWVGE

<u>INPSSSTINYAPSLKDKFTISRDNAKNTLYLQMNSLRAEDTAVYYCASLY</u>

<u>YDYGDAYDYW</u>GQGTLVTVSS

Alignments:
A CLUSTAL W (1.83) multiple sequence alignment of the various substituted positions within the HC sequence provides appropriate sequence comparisons in FIG. 8. The "General sequence" represents an HC sequence, whereby each X represents a potential amino acid change to any given amino acid. Preferred amino acid substitutions are those described above for each of the potentially mutated positions.

Preferred Embodiments Regarding Humanized VL Variants Chimeric Sequence:

LCmouse (SEQ ID NO. 43):
DIVMTQSQRFMTTSVGDRVSVTC<u>KASQSVDSNVA</u>WYQQKPRQSPKALIF<u>S</u>

<u>ASLRFS</u>GVPARFTGSGSGTDFTLTISNLQSEDLAEYFC<u>QQYNNYPLTFGA</u>

GTKLELKR

The LC mouse sequence represents the variable region of the light chain (VL) originally developed for the chimeric antibody J22.9-xi, which comprises VL and VH domains obtained from a mouse antibody, capable of binding an epitope of the extracellular domain of CD269 (BCMA), and the VL and VH domains are fused to human CL and CH domains, respectively.

Partially Humanized Sequences:

```
LC partially humanized (SEQ ID NO 10):
DIVMTQSPATLSVSVGDEVTLTCKASQSVDSNVAWYQQKPGQAPKLLIYS

DDLRFSGVPARFSGSGSGTDFTLTISSLQSEDFAVYYCQQYNNYPLTFGA

GTKLELKR
```

The LC partially humanized sequence represents a modified sequence (via amino acid substitutions) in comparison to the chimeric antibody disclosed in the examples of the present invention, whereby the VL and VH binding regions have been modified with respect to their sequence to make them more suitable for administration in humans.

Humanized VL Sequence:

```
hLC01 (SEQ ID NO 11):
EIVMTQSPATLSVSPGERATLSCKASQSVDSNVAWYQQKPGQAPRALIYS

ASLRFSGIPARFSGSGSGTEFTLTISSLQSEDFAVYYCQQYNNYPLTFGA

GTKLELKR
```

Humanized VL sequence with removal of post translational modification motifs:

```
hLC02 (SEQ ID NO 12):
EIVMTQSPATLSVSPGERATLSCKASQSVX₁X₂NVAWYQQKPGQAPRALIY

SASLRFSGIPARFSGSGSGTEFTLTISSLQSEDFAVYYCQQYNNYPLTFG

AGTKLELKR
```

Wherein:
X₁X₂: ES, SS, TS, QS, HS, DH, preferably ES.

The "hLC01" and "hLC02" humanized sequences represent novel amino acid sequences that comprise amino acid sequence changes in comparison to both the original chimeric sequence and the partially humanized sequences described herein.

The PTM mutations are intended to remove potentially detrimental post translational modification motifs from said proteins, whilst maintaining the advantageous binding properties. The positions 1, 8, 9, 10, 13, 15, 17, 19, 20, 21, 22, 30, 41, 43, 45, 49, 58, 63, 70, 77, 83, 85 and/or 87 of hLC01 and hLC02 are preferably mutated (substituted) in comparison to the original chimeric sequence.) The importance of the substitution relates primarily to the resulting amino acid, not the originating amino acid. The change may therefore also be carried out from the corresponding amino acid of the original chimeric amino acid or other variant.

The following substitutions are novel over the chimeric and partially humanized sequences:
the amino acid D1 of the LC (VL) sequence is substituted with E;
the amino acid V15 of the LC (VL) sequence is substituted with P;
the amino acid D17 of the LC (VL) sequence is substituted with E;
the amino acid V19 of the LC (VL) sequence is substituted with A;
the amino acid T22 of the LC (VL) sequence is substituted with S;
the amino acids D30 and S31 of the LC (VL) sequence is substituted with any amino acid combination, preferably ES, SS, TS, QS, HS, DH;
the amino acid V58 of the LC (VL) sequence is substituted with I; and/or
the amino acid D70 of the LC (VL) sequence is substituted with E.

Sequences that May be Modified in their CDR Binding Regions at Those Residues Required for Interaction with BCMA:

```
hLC03 - modified amino acids involved in
interaction with BCMA (SEQ ID NO 13):
EIVMTQSPATLSVSPGERATLSCKASQSVDX₁X₂VX₃WX₄QQKPGQAPRA

LIX₅X₆AX₇X₈RX₉SGIPARFSGSX₁₀X₁₁GTEFTLTISLQSEDFAVYYC

X₁₂QX₁₃NNX₁₄PX₁₅TFGAGTKLELKR
```

Wherein preferred amino acids are:
X₁: S, H, T, N, D, Q;
X₂: N, E, Q;
X₃: A, G, V, S, T, L, I;
X₄: Y, F, L, I, V, A, G;
X₅: Y, F, L;
X₆: S, T;
X₇: S, T, D, N, H, E, Q;
X₈: L, V, I, M;
X₉: F, L, I, V, Y, M;
X₁₀: G, X;
X₁₁: S, X;
X₁₂: Q, V, L, I, M;
X₁₃: Y, F, L, I, Q;
X₁₄: Y, F, R, Q, K; and/or
X₁₅: L, I, V, F.

The "hLC03 humanized sequence" represents novel amino acid sequences that comprise amino acid sequence changes in comparison to both the original chimeric sequence and the partially humanized sequence. These sequence changes are intended to reflect potential changes in the amino acids that bind the BCMA target, which may be substituted, whilst maintaining the advantageous binding properties. The importance of the substitution relates primarily to the resulting amino acid, not the originating amino acid. The change may therefore also be carried out from the corresponding amino acid of the original chimeric amino acid or other variant.

For example:
the amino acid S31 of the LC (VL) sequence is S, H, T, N, D, Q;
the amino acid N32 of the LC (VL) sequence is N, E, Q;
the amino acid A34 of the LC (VL) sequence is A, G, V, S, T, L, I;
the amino acid Y36 of the LC (VL) sequence is Y, F, L, I, V, A, G;
the amino acid Y49 of the LC (VL) sequence is Y, F, L;
the amino acid S50 of the LC (VL) sequence is S, T;
the amino acid S52 of the LC (VL) sequence is S, T, D, N, H, E, Q;
the amino acid L53 of the LC (VL) sequence is L, V, I, M;
the amino acid F55 of the LC (VL) sequence is F, L, I, V, Y, M;
the amino acid G66 of the LC (VL) sequence is G, X;
the amino acid S67 of the LC (VL) sequence is S, X;
the amino acid Q89 of the LC (VL) sequence is Q, V, L, I, M;
the amino acid Y91 of the LC (VL) sequence is Y, F, L, I, Q;
the amino acid Y94 of the LC (VL) sequence is Y, F, R, Q, K; and/or the amino acid L96 of the LC (VL) sequence is L, I, V, F.

In general, any change to a CDR region may also be considered as a feature of a CDR sequence when considered independently of the framework sequence as a whole. Such modified CDR sequences may be considered defining features of the present invention, either within or independent of their context in the entire framework region described herein. For example, the CDR sequences identified by underline in the hLC01 to hLC03 may—in their unmodified or substituted form—be considered a defining feature of the invention independently of the surrounding framework sequence.

Example of Humanized LC Sequence:

hLC04 (SEQ ID NO 14):
EIVMTQSPATLSVSPGERATLSC<u>KASQSVESNVA</u>WYQQKPGQAPRALIY<u>S</u>
<u>ASLRFS</u>GIPARFSGSGSGTEFTLTISSLQSEDFAVYYC<u>QQYNNYPLTFGA</u>
GTKLELKR

Alignments:

A CLUSTAL W (1.83) multiple sequence alignment of the various potentially amended sites within the LC sequence provides appropriate sequence comparisons in FIG. 9. The "General sequence" represents an LC sequence, whereby each X represents a potential amino acid change. Preferred amino acid substitutions are those described above for each of the potentially mutated positions.

The present invention therefore relates to the humanized sequences according to hHC01, hHC02, hHC03, hHC04, hHC05, hHC06, hHC07, hLC01, hLC02, hLC03 and/or hLC04, or any given combination thereof.

All possible combinations of potential modifications for any given potentially variant residue proposed herein (as identified by X in the "general" sequence) are encompassed by the present invention. By combining one or more of these various substitutions, humanized variants may be generated that exhibit the desired binding properties of the chimeric antibody originally developed and demonstrated herein. The antibodies or parts thereof described herein also encompass a sequence with at least 80%, preferably 90%, sequence identity to those humanized sequences disclosed explicitly or disclosed through a sequence formula.

Preferred Embodiments Regarding the Antibody Epitope

The invention therefore relates to an isolated antibody or antibody fragment that binds CD269 (BCMA), wherein the antibody binds an epitope comprising one or more amino acids of residues 13 to 32 of CD269 (BCMA).

The amino acid sequence of residues 13 to 32 of CD269 are shown in SEQ ID No. 40. The N-terminus sequence of CD269 is provided in SEQ ID No. 39. The extracellular domain of CD269 is provided as SEQ ID No. 38.

An antigen comprising the extracellular domain of CD269 according to SEQ ID No. 38 was used in vaccination in order to generate the binding specificity of the mouse and chimeric antibody described herein. Use of the entire CD269 protein, or fragments thereof comprising either a membrane-bound or intracellular domain, as an antigen during antibody generation could produce antibodies that bind concealed or intracellular domains of CD269, thereby rendering such agents unsuitable or disadvantageous for therapeutic application. The antibodies of the present invention are therefore defined by their binding to the extracellular portion of CD269. The specific epitope within the extracellular domain also represents a preferred novel and unexpected characterising feature of the invention.

Fab fragments prepared from mouse or chimeric antibodies were crystallized in complex with the purified BCMA extracellular domain and the complex structure solved. The structural analysis has revealed detailed information of the epitope of the antibody of the present invention and its biological relevance. The binding of an epitope comprising one or more amino acids of residues 13 to 32 of CD269 (BCMA) of the extracellular domain by the antibody of the present invention is an advantageous property, as this region shows a significant overlap with the binding sites of BAFF and APRIL, the two natural ligands of CD269. No anti-CD269 antibody described in art to date has shown such comprehensive overlap with the BAFF and APRIL binding sites.

In one embodiment the isolated antibody or antibody fragment of the present invention is characterised in that the antibody binds an epitope comprising one or more of amino acids 13, 15, 16, 17, 18, 19, 20, 22, 23, 26, 27 or 32 of CD269 (BCMA). In another embodiment the isolated antibody or antibody fragment of the present invention is characterised in that the antibody binds an epitope consisting of amino acids 13, 15, 16, 17, 18, 19, 20, 22, 23, 26, 27 and 32 of CD269 (BCMA). These residues represent the amino acids that interact directly with the antibody of the present invention, as identified by the crystal structure data provided herein. The numbering of these residues has been carried out with respect to SEQ ID No. 39, which provides the N-terminal sequence of CD269.

In one embodiment of the invention the isolated antibody or antibody fragment is characterised in that the antibody binding to CD269 (BCMA) disrupts the BAFF-CD269 and/or APRIL-CD269 interaction.

The binding of the antibodies of the present invention to the extracellular domain of CD269 disrupts the BAFF-CD269 interaction. Due to the fact that the binding sites of APRIL and BAFF are positioned at similar sites to the antibody epitope, the binding of the antibody to CD269 will also block the APRIL-CD269 interaction.

Comparison of the specific epitope of the antibody of the present invention with the binding sites of APRIL and BAFF, for which crystal structures have been solved and their interaction sites mapped, reveals a comprehensive overlap in the binding sites of the natural ligands and the antibody as described herein. This represents a beneficial and unexpected aspect of the invention and enables a reliable and effective disruption of BAFF-CD269 and/or APRIL-CD269 interactions.

The invention therefore relates to an isolated antibody or antibody fragment as described herein, wherein the antibody disrupts the APRIL-CD269 interaction by binding an epitope comprising one or more amino acids of residues 13, 15, 17, 18, 19, 22, 26, 27, 30, 31, 32, 33, 34, 35 of CD269 (BCMA), in particular consisting of amino acids 13, 15, 17, 18, 19, 22, 26, 27, 32. These amino acids correspond to the binding site of APRIL on CD269, and the overlapping residues of CD269 that bind both the antibody as described herein and APRIL, respectively.

The invention therefore relates in another embodiment to an isolated antibody or antibody fragment as described herein, wherein the antibody disrupts the BAFF-CD269 interaction by binding an epitope comprising one or more amino acids of residues 13, 15, 16, 17, 18, 19, 22, 25, 26, 27, 29, 30, 31, 32, 34, 35 of CD269 (BCMA), in particular an epitope consisting of amino acids 13, 15, 16, 17, 18, 19, 22, 26, 27, 32. These amino acids correspond to the binding site of BAFF on CD269, and the overlapping residues of CD269 that bind both the antibody as described herein and BAFF, respectively.

Although antibodies that bind CD269 have been described in the art that also potentially disrupt APRIL- or BAFF-interactions with CD269, no relevant disclosure is provided relating to the specific epitope of such antibodies. It cannot be assumed that the previously described antibodies also bind an epitope with such a comprehensive overlap as the antibodies of the present invention. Even if APRIL- or BAFF-interactions with CD269 have been shown to be disrupted, this could potentially occur due to binding a considerably different epitope and subsequent steric hindrance of APRIL or BAFF docking. The degree of disruption of APRIL- or BAFF-interactions with CD269 caused by the antibodies of the prior has not been documented previously.

The antibodies of the present invention enable an effective and reliable disruption, which potentially represents an improved technical effect in comparison to those antibodies described in the art. An in vitro blocking assay can be performed for determination and comparison of BAFF and/or APRIL disruption, for example with the extracellular domain of human BCMA and recombinant BAFF or APRIL.

In a preferred embodiment the epitope specificity, in combination with the high affinity shown by the antibodies described herein, represents a novel and unexpected technical effect. In essence, the exceptionally high affinity of the J22.9 antibody and the humanized variants thereof, provides not only "disruption" or "blocking" of the binding of the natural ligands; but rather the ultra-high affinity of the antibodies of the invention ensures that the native ligands are essentially excluded completely or almost completely from binding their BCMA target when the antibody is present.

As disclosed in the examples below, the affinity of the humanized antibodies as described herein is surprisingly high and comparatively better than similar approaches attempted in the prior art. A Kd in the pM range (as shown below) is commonly accepted as an outstanding affinity not to be expected in common practice.

In another aspect the humanized antibody or antibody fragment of the invention binds CD269 with high affinity, for example when measured by surface plasmon resonance, such as Biacore, the antibody binds to human CD269 with an affinity of 100 nM, 90, 80, 70, 60, 50, 40, 30 nM or less, or 20 nM or less, or an affinity of 15 nM or less, or an affinity of 5 nM or less, or an affinity of 1000 pM or less, or an affinity of 500 pM or less, or an affinity of 100 pM or less, or 80 pM or less, or for example about 50 pM.

In a further embodiment the antibody binds to human CD269 when measured by surface plasmon resonance, such as Biacore, of between about 1 pM and about 100 nM, or between about 100 pM and about 50 nM, or between about 200 pM and about 20 nM.

Further Preferred Embodiments of the Invention

In one embodiment the invention relates to an antibody or antibody fragment comprising an amino acid sequence defined by one or more of the amino acids that directly interact with the CD269 target and/or one or more amino acids that interact via water interactions (see Tables 1 to 6). The large number of water interactions involved in the binding of the antibody as described herein to the epitope represents an unusual and surprising aspect of the binding. In particular the high affinity of the antibody directed to the particular epitope described herein, in combination with the large number of water interactions involved in the binding surface between the antibody and epitope, represents a surprising and unexpected aspect of the invention.

The invention therefore relates to an antibody or antibody fragment comprising an amino acid sequence as described herein, wherein the sequence is characterised by the presence of the specific amino acid residues that are involved in the interaction surface with the target epitope via a water bridge according to table 5, selected from the group comprising Ser31, Asn32, Tyr36, Ser50, Ser52, Gly66, Gln89, Tyr91 and/or Tyr94 of the light chain, and/or Trp33, Ser35, Trp47, Glu50, Leu99 and/or Tyr101 of the heavy chain, with respect to the chimera disclosed herein, or with respect to the corresponding residue of the humanized sequence variants disclosed herein.

Although the examples with respect to water bridge formation of the antibody were carried out with the J22.9-xi chimera, the inventors assert that this technical effect is maintained in the humanized variants of the present invention due to the maintenance of binding characteristics in the humanized variants compared to the original chimeric antibody tested. In the heavy chain, the only mutated water bridge residue is Y101, but its water interaction involves a main chain (i.e. backbone) atom, and therefore can be reasonably assumed not to change due to mutating the sidechain; in the light chain there are no mutations of residues involved in water bridges.

The antibody of the invention can be further characterised by the amino acid residues of the epitope involved in the interaction via water bridges with the antibody as described herein. The relevant features are provided in Table 5. The invention is therefore, for example in one embodiment, characterised in that residue Ser31 of the light chain interacts with Thr32 of CD269 via a water molecule. Such a description of the binding properties of the antibody of the present invention is intended for each interaction as provided in Table 5.

Furthermore, sequence variants of the antibodies described herein are encompassed in the present invention, in which one or more residues involved in a "water bridging" interaction is modified in order to "substitute" a direct side-chain interaction into the sequence at the expense of a water "bridge". For example, a mutation or change could be made in the amino acid sequence displacing the water from the interaction interface but not substantially affecting the affinity of the interaction. The invention therefore relates to an antibody or antibody fragment comprising an amino acid sequence as described herein, wherein the sequence is characterised by sequence variation of those amino acid residues that are involved in the interaction surface with the target epitope via a water bridge according to table 5, selected from the group comprising Ser31, Ser31, Asn32, Tyr36, Ser50, Ser52, Gly66, Gln89, Tyr91 and/or Tyr94 of the light chain, and/or Trp33, Ser35, Trp47, Glu50, Leu99 and/or Tyr101 of the heavy chain, with respect to the chimera disclosed herein, or with respect to the corresponding residue of the humanized sequence variants disclosed herein. Variation at the corresponding positions of the humanized antibodies described herein may relate to any given amino acid substitution, preferably an amino acid substitution that would effectively displace the water from the interaction but maintain similar binding properties with respect to epitope affinity and specificity.

In one embodiment of the invention the isolated antibody or antibody fragment is characterised in that the antibody is glycosylated, preferably comprising an N-linked oligosaccharide chain, preferably at Asn297 of the heavy chain.

Glycosylation of the antibody refers to the attachment of carbohydrates or glycans to the antibody. N-linked glycans are attached to the nitrogen of asparagine or arginine sidechains. The carbohydrate chains attached to the target proteins serve various functions. For instance, some proteins do not fold correctly unless they are glycosylated first. Also, polysaccharides linked at the amide nitrogen of asparagine in the protein can confer stability on some secreted glycoproteins. Glycosylation in this case is not a strict requirement for proper folding, but unglycosylated protein can be degraded more quickly.

As is demonstrated in the examples of the present invention, the deglycosylation of the antibody disclosed therein leads to a reduction in therapeutic effect in comparison to glycosylated forms of the antibody. It was surprising, that the glycosylation would play a significant role in maintaining activity of the antibody. The glycosylation therefore represents a preferred embodiment of the invention associated with unexpected technical advantages.

As demonstrated in the examples herein, although the overall tumor load of animals treated with J22.9-xi-N-glycan (deglycosylated) was not significantly different from animals receiving the isotype control antibody, the lifespan of these mice was substantially increased compared to the isoAb-treated group. Since J22.9-xi-N-glycan was shown to be unable to induce ADCC or CDC, this result indicates that alone the binding of J22.9-xi to BCMA hinders tumor growth. It may be reasonably considered that this is due to blocking of the interaction between the receptor and its native ligands (APRIL and BAFF). This aspect of the invention and the antibodies described herein represents a surprising technical effect, which could not have been derived from the antibodies of the prior art. The J22.9-xi-N-glycan (deglycosylated) can be considered a control sample in the experiments described which enables the binding of the antibody to its target epitope, without the downstream effects of ADCC or CDC, to be assessed for potentially therapeutic effect. The antibodies of the invention, preferably with glycosylation, therefore demonstrate such an effective epitope binding that enables the prevention (or significant disruption) of binding by the natural ligands to lead to cell toxicity. This characteristic of the antibodies described herein has not been described for similar antibodies described in the art.

Although the examples with respect to glycosylation of the antibody were carried out with the J22.9-xi chimera, the inventors assert that this technical effect is maintained in the humanized variants of the present invention due to the maintenance of binding characteristics in the humanized variants compared to the original chimeric antibody tested. The preferred position of glycosylation (Asn297 of the heavy chain) has no direct connection to any of the mutated residues and lies in the human constant region of the full IgG. It is therefore reasonable to assume that no differences in the glycosylation pattern at this position exist in any of the J22.9 variants compared to the chimeric antibody.

Use and Functional Aspects of the Invention

The antibodies of the present invention are capable of binding the epitopes described herein, blocking interaction of the natural ligands of this epitope, and inducing CDC and ADCC.

Antibody-Dependent Cell-Mediated Cytotoxicity (ADCC) is one factor induced by the antibody of the present invention that generates the desired therapeutic effect. ADCC is a mechanism of cell-mediated immune defense, whereby an effector cell of the immune system actively lyses a target cell, whose membrane-surface antigens have been bound by specific antibodies. After binding of CD269-expressing cells by the antibodies of the present invention ADCC may be induced. Classical ADCC is mediated by natural killer (NK) cells; macrophages, neutrophils and eosinophils can also mediate ADCC. ADCC is part of the adaptive immune response due to its dependence on a prior antibody response. Experiments in mice may indicate that ADCC is an important mechanism of action of therapeutic antibodies as described herein.

A preferred embodiment of the invention relates to the isolated antibody or antibody fragment as described herein for use as a medicament in the treatment of a medical disorder associated with the presence of pathogenic B cells.

In one embodiment of the invention the medical disorder is a CD269-associated disorder, preferably associated with pathogenic B cells, which is preferably a disease of plasma cells and/or memory B cells.

A disease of plasma cells may be a cancer of plasma cells, for example multiple myeloma, plasmacytoma, Waldenström macroglobulinemia or plasma cell leukemia. A disease of plasma cells may be a cancer of B lymphocytes, such as Hodgkin's disease.

In one embodiment of the invention the medical disorder is an autoimmune disease associated with autoreactive plasma cells and/or autoreactive memory B cells, such as an inflammatory autoimmune disease, for example systemic lupus erythematosus or rheumatic arthritis.

The invention therefore also encompasses a method of treatment for the medical disorders as disclosed herein, preferably comprising the administration of a therapeutically effective amount of antibody to a subject in need of such treatment.

A further aspect of the invention relates to an antibody-drug conjugate (ADC) comprising the antibody or antibody fragment as described herein. Anti-CD269 Antibody-Drug Conjugates "anti-CD269 ADC" can be described as an anti-CD269 antibody or fragment thereof conjugated to a therapeutic agent. In certain embodiments, the ADC comprises an anti-CD269 antibody (e.g., a humanized variant of J22.9-xi as described herein).

The ADCs or ADC derivatives as described herein produce clinically beneficial effects on CD269-expressing cells when administered to a subject with a CD269-expressing medical condition, such as cancer or autoimmune disorder. In one embodiment, the anti-CD269 antibody or derivative thereof is conjugated to a cytotoxic agent, such that the resulting ADC or ADC derivative exerts a cytotoxic effect on a CD269-expressing cancer cell, preferably when taken up or internalized by the cell.

The anti-CD269 ADC or ADC derivative is preferably internalized and accumulates within a CD269-expressing cell, where the ADC or ADC derivative exerts a therapeutic effect (e.g., a cytotoxic effect). Particularly suitable moieties for conjugation to antibodies or antibody derivatives are chemotherapeutic agents, prodrug converting enzymes, radioactive isotopes or compounds, or toxins. For example, an anti-CD269 antibody or derivative thereof can be conjugated to a cytotoxic agent such as a chemotherapeutic agent, or a toxin (e.g., a cytostatic or cytocidal agent).

Another aspect of the invention relates to a preferably isolated nucleic acid molecule selected from the group consisting of:

a) a nucleic acid molecule comprising a nucleotide sequence
which encodes an isolated antibody or antibody fragment according to any one of the preceding claims, which encodes an amino acid sequence selected from the group consisting of those sequences according to SEQ ID 1 to 31 and 41 to 42, comprising a sequence or sequence fragment of SEQ ID No. 32 to 36, b) a nucleic acid molecule which is complementary to a nucleotide sequence in accordance with a);

c) a nucleic acid molecule comprising a nucleotide sequence having sufficient sequence identity to be functionally analogous/equivalent to a nucleotide sequence according to a) or b), comprising preferably a sequence identity to a nucleotide sequence according to a) or b) of at least 80%, preferably 90%, more preferably 95%;

d) a nucleic acid molecule which, as a consequence of the genetic code, is degenerated into a nucleotide sequence according to a) through c); and e) a nucleic acid molecule according to a nucleotide sequence of a) through d) which is modified by deletions, additions, substitutions, translocations, inversions and/or insertions and functionally analogous/equivalent to a nucleotide sequence according to a) through d).

A further aspect of the invention relates to a host cell, such as a bacterial cell or mammalian cell, preferably a hybridoma cell or cell line, capable of producing an antibody or antibody fragment as described herein, and/or comprising a nucleic acid molecule as described herein.

A further aspect of the invention relates to a pharmaceutical composition comprising the isolated antibody or antibody fragment as described herein, a nucleic acid molecule as described herein or a host cell as described herein, together with a pharmaceutically acceptable carrier.

An additional and surprising aspect of the invention is an improved stability of the antibody as disclosed herein. The antibody can readily be stored for extended periods under appropriate conditions without any loss of binding affinity. Appropriate tests have been carried out regarding maintenance of activity after storage at either −80 or 4 deg C., which demonstrate unexpectedly good stability of the antibody and maintenance of activity after storage at both aforementioned temperatures (FIG. 3c). This improved stability is evident for the chimeric antibody, and surprisingly also for the humanized variants thereof. Unexpectedly the stability of the humanized variants is improved over the chimera under long term storage.

A further advantage of the antibodies as described herein the effective systemic depletion of myeloma cells as demonstrated in the examples. Antibodies previously disclosed in the prior art have not been demonstrated to exhibit the desired anti-plasma cell effect in a systemic manner. Studies carried out on the antibodies of the prior art disclose only sub-cutaneous injection with myeloma cells and subsequent treatment of the isolated cell mass. The present invention provides an antibody capable of systemic depletion of cancerous multiple myeloma cells after their i.v. injection, as demonstrated in the examples. The effective depletion of targeted cells represents a technical effect that has not previously been demonstrated in the prior art in addition to a beneficial property of the antibodies of the present invention.

BRIEF DESCRIPTION OF THE DRAWINGS

The invention is demonstrated by way of the example by the examples and figures disclosed herein. The figures provided herein represent particular embodiments of the invention and are not intended to limit the scope of the invention. The figures are to be considered as providing a further description of possible and potentially preferred embodiments that enhance the technical support of one or more non-limiting embodiments.

FIG. 3: In vitro cytotoxicity of J22.9-xi. (a) CD269-positive MM.1S-Luc cells mixed with human PBMCs at an effector to target ratio of 20:1 were incubated with the indicated concentrations of J22.9-xi for 4 hours. Open symbols indicate cytotoxic activity of J22.9-xi without —N-glycans when incubated with PBMCs from donor 1 and 2. Error bars indicate SEM. (b) Deglycosylation does not affect J22.9-xi binding to MM.1S cells. (c) Storage of J22.9-xi for 3 weeks at 4° C. or −80° C. does not affect cytotoxicity.

FIG. 5: Treatment of established tumors. (a) Tumor development over time with administration of 200 µg of J22.9-xi or control antibody twice weekly, and untreated control mice. (b) Total tumor load between day 8 and 48 (AUC of (a)). Plotted are the mean values with SEM (*P<0.05, **P<0.01, t-test). (c) Overall survival of J22.9-xi and isotype control mice. The P value was calculated using the Log-rank (Mantel-Cox) Test. (d) An overview of the experimental time line is provided.

FIG. 8: Summary of the sequences of the humanized antibodies compared to J22.9-xi. Sequence comparisons were carried out using standard alignment software. HCg: SEQ ID NO: 41; HCm: SEQ ID NO: 1; HCpH: SEQ ID NO: 2; hHC01: SEQ ID NO: 3; hHC02: SEQ ID NO: 4; hHC03: SEQ ID NO: 5; hHC04: SEQ ID NO: 6; hHC05: SEQ ID NO: 7; hHC06: SEQ ID NO: 8; and hHC07: SEQ ID NO: 9.

FIG. 9: Summary of the sequences of the humanized antibodies compared to J22.9-xi. Sequence comparisons were carried out using standard alignment software. LCg: SEQ ID NO: 42; LCm: SEQ ID NO: 43; LCpH: SEQ ID NO: 10; hLC01: SEQ ID NO: 11; hLC02: SEQ ID NO: 12; hLC03: SEQ ID NO: 13; and hLC04: SEQ ID NO: 14.

FIG. 10: Sequence optimized variants of J22.9-xi show similar binding in ELISA. Binding of the chimeric J22.9-xi and humanized variants was tested via ELISA using human BCMA (hBCMA) or cynomolgous BCMA (cyBCMA) coated microtiter plates (J22.9-H corresponds to humanized sequence SEQ ID No. 27; J22.9-FSY corresponds to humanized and PTM modified SEQ ID No. 28; J22.9-ISY corresponds to humanized and PTM modified SEQ ID No. 29).

DETAILED DESCRIPTION OF THE INVENTION

Figure 1:
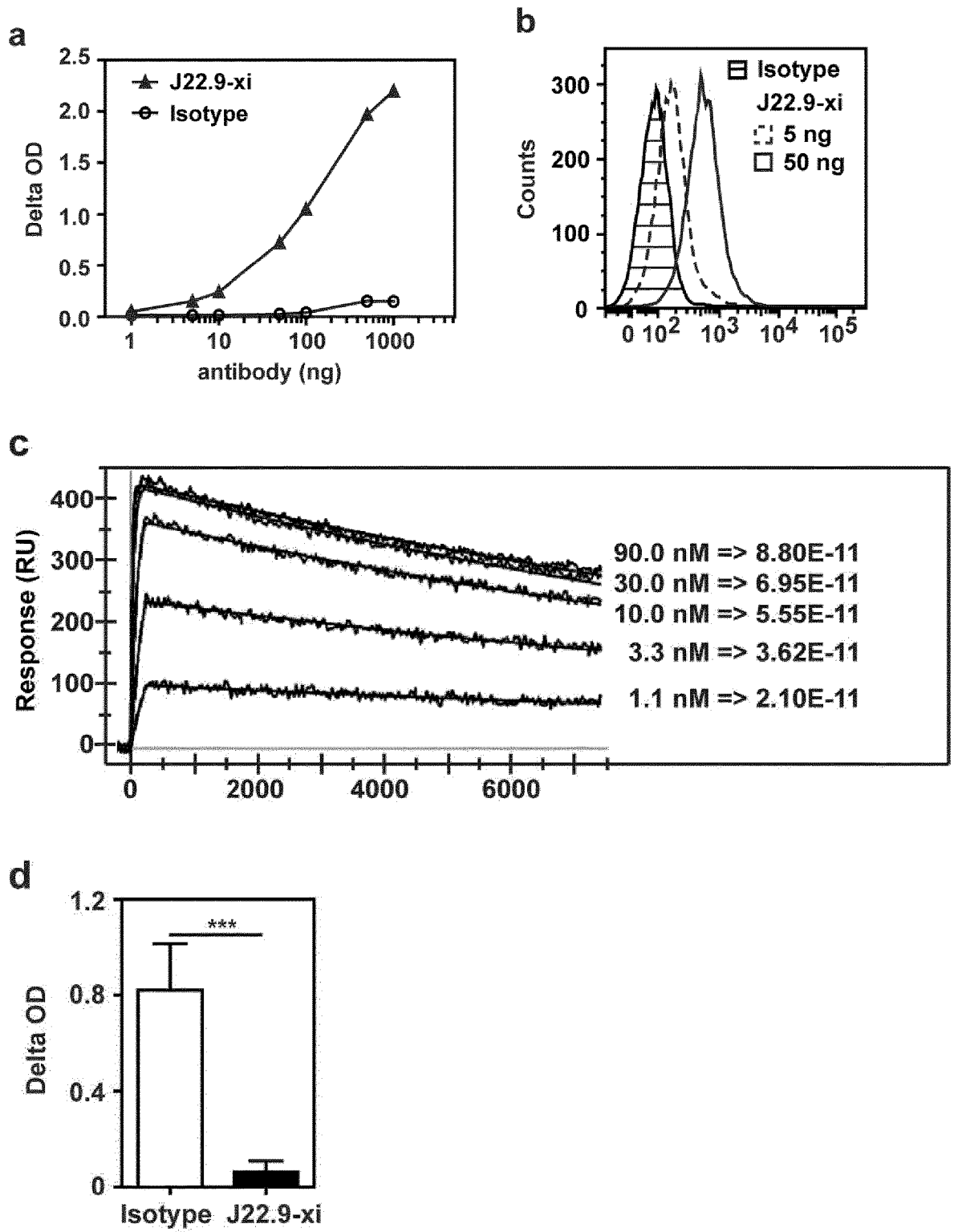
FIG. 1: In vitro characterization of J22.9-xi. Concentration dependent binding of J22.9-xi to BCMA in (a) ELISA and (b) by flow cytometry using CD269-positive MM.1S cells. (c) Binding affinity of J22.9-xi to BCMA was determined from surface plasmon resonance measurements with the indicated concentrations of BCMA. (d) J22.9-xi blocks the interaction between BAFF and BCMA adsorbed onto microtiter plates.

As used herein, an "antibody" generally refers to a protein consisting of one or more polypeptides substantially encoded by immunoglobulin genes or fragments of immunoglobulin genes. Where the term "antibody" is used, the term "antibody fragment" may also be considered to be referred to. The recognized immunoglobulin genes include the kappa, lambda, alpha, gamma, delta, epsilon and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD, and IgE, respectively. The basic immunoglobulin (antibody) structural unit is known to comprise a tetramer or dimer. Each tetramer is composed of two identical pairs of polypeptide chains, each pair having one "light" (L) (about 25 kD) and one "heavy" (H) chain (about 50-70 kD). The N-terminus of each chain defines a variable region of about 100 to 110 or more amino acids, primarily responsible for antigen recognition. The terms "variable light chain" and "variable heavy chain" refer to these variable regions of the light and heavy chains respectively. Optionally, the antibody or the immunological portion of the antibody, can be chemically conjugated to, or expressed as, a fusion protein with other proteins.

The antibodies of the invention are intended to bind against mammalian, in particular human, protein targets. The use of protein names may correspond to either mouse or human versions of a protein.

"Specific binding" is to be understood as via one skilled in the art, whereby the skilled person is clearly aware of various experimental procedures that can be used to test binding and binding specificity. Some cross-reaction or background binding may be inevitable in many protein-protein interactions; this is not to detract from the "specificity" of the binding between antibody and epitope. The term "directed against" is also applicable when considering the term "specificity" in understanding the interaction between antibody and epitope.

Antibodies of the invention include, but are not limited to polyclonal, monoclonal, bispecific, human, humanized or chimeric antibodies, single variable fragments (ssFv), single domain antibodies (such as VHH fragments from nanobodies), single chain fragments (scFv), Fab fragments, F(ab')$_2$ fragments, fragments produced by a Fab expression library, anti-idiotypic antibodies and epitope-binding fragments or combinations thereof of any of the above, provided that they retain the original binding properties. Also mini-antibodies and multivalent antibodies such as diabodies, triabodies, tetravalent antibodies and peptabodies can be used in a method of the invention. The immunoglobulin molecules of the invention can be of any class (i.e. IgG, IgE, IgM, IgD and IgA) or subclass of immunoglobulin molecules. Thus, the term antibody, as used herein, also includes antibodies and antibody fragments either produced by the modification of whole antibodies or synthesized de novo using recombinant DNA methodologies.

Humanized antibody comprising one or more CDRs of antibodies of the invention or one or more CDRs derived from said antibodies can be made using any methods known in the art. For example, four general steps may be used to humanize a monoclonal antibody. These are: (1) determining the nucleotide and predicted amino acid sequence of the starting antibody light and heavy variable domains (2) designing the humanized antibody, i.e., deciding which antibody framework region to use during the humanizing process (3) the actual humanizing methodologies/techniques and (4) the transfection and expression of the humanized antibody. See, for example, U.S. Pat. Nos. 4,816,567; 5,807, 715; 5,866,692; 6,331,415; 5,530,101; 5,693,761; 5,693,762; 5,585,089; 6,180,370; 5,225,539; 6,548,640.

The term humanized antibody means that at least a portion of the framework regions, and optionally a portion of CDR regions or other regions involved in binding, of an immunoglobulin is derived from or adjusted to human immunoglobulin sequences. The humanized, chimeric or partially humanized versions of the mouse monoclonal antibodies can, for example, be made by means of recombinant DNA technology, departing from the mouse and/or human genomic DNA sequences coding for H and L chains or from cDNA clones coding for H and L chains. Humanized forms of mouse antibodies can be generated by linking the CDR regions of non-human antibodies to human constant regions by recombinant DNA techniques (Queen et al., 1989; WO 90/07861). Alternatively the monoclonal antibodies used in the method of the invention may be human monoclonal antibodies. Human antibodies can be obtained, for example, using phage-display methods (WO 91/17271; WO 92/01047).

As used herein, humanized antibodies refer also to forms of non-human (e.g. murine, camel, llama, shark) antibodies that are specific chimeric immunoglobulins, immunoglobulin chains, or fragments thereof (such as Fv, Fab, Fab', F(ab')$_2$ or other antigen-binding subsequences of antibodies) that contain minimal sequence derived from non-human immunoglobulin.

As used herein, human or humanized antibody means an antibody having an amino acid sequence corresponding to that of an antibody produced by a human and/or has been made using any of the techniques for making human antibodies known in the art or disclosed herein. Human antibodies can be selected by competitive binding experiments, or otherwise, to have the same epitope specificity as a particular mouse antibody. The humanized antibodies of the present invention surprisingly share the useful functional properties of the mouse antibodies to a large extent. Human polyclonal antibodies can also be provided in the form of serum from humans immunized with an immunogenic agent. Optionally, such polyclonal antibodies can be concentrated by affinity purification using amyloid fibrillar and/or non-fibrillar polypeptides or fragments thereof as an affinity reagent. Monoclonal antibodies can be obtained from serum according to the technique described in WO 99/60846.

The present invention further relates to the use of the antibodies, or fragments thereof, as described herein, for example the variable regions, in recognition molecules or affinity reagents that are suitable for selective binding to a target. The affinity reagent, antibody or fragment thereof according to the invention may be PEGylated, whereby PEGylation refers to covalent attachment of polyethylene glycol (PEG) polymer chains to the inventive antibody. PEGylation may be routinely achieved by incubation of a reactive derivative of PEG with the target molecule. PEGylation to the antibody can potentially mask the agent from the host's immune system, leading to reduced immunogenicity and antigenicity or increase the hydrodynamic size of the agent which may prolong its circulatory time by reducing renal clearance.

A variable region of an antibody refers to the variable region of the antibody light chain or the variable region of the antibody heavy chain, either alone or in combination. The variable regions of the heavy and light chain each consist of four framework regions (FR) connected by three complementarity determining regions (CDRs) also known as hypervariable regions. The CDRs in each chain are held together in close proximity by the FRs and, with the CDRs from the other chain, contribute to the formation of the antigen-binding site of antibodies. There are at least two techniques for determining CDRs: (1) an approach based on cross-species sequence variability (i.e., Kabat et al. Sequences of Proteins of Immunological Interest, (5th ed., 1991, National Institutes of Health, Bethesda Md.)); and (2) an approach based on crystallographic studies of antigen-antibody complexes (Al-lazikani et al. (1997) J. Molec. Biol. 273:927-948). As used herein, a CDR may refer to CDRs defined by either approach or by a combination of both approaches.

In some embodiments, the invention provides an antibody, which comprises at least one CDR, at least two, at least three, or more CDRs that are substantially identical to at least one CDR, at least two, at least three, or more CDRs of the antibody of the invention. Other embodiments include antibodies which have at least two, three, four, five, or six CDR(s) that are substantially identical to at least two, three, four, five or six CDRs of the antibodies of the invention or derived from the antibodies of the invention. In some embodiments, the at least one, two, three, four, five, or six CDR(s) are at least about 85%, 86%, 87%, 88%, 89%, 90%, 95%, 96%, 97%, 98%, or 99% identical to at least one, two or three CDRs of the antibody of the invention. It is understood that, for purposes of this invention, binding specificity and/or overall activity is generally retained, although the extent of activity may vary compared to said antibody (may be greater or lesser).

The half life and cytotoxic potential of an antibody are dependent primarily on the interaction of the Fc-domain with different Fc-gamma-receptors. In the case of the antibody half life, the neonatal Fc receptor (FcRn) plays a major role. This receptor is expressed on several cell types and tissues such as monocytes and vascular endothelia cells that are able to take up serum proteins into their recycling endosomes. In the endosomes, the pH is decreased to approximately 6 and under these conditions the antibodies are able to bind to FcRn. This interaction protects the antibodies from degradation until they are again released into the blood where the physiological pH disrupts the binding to the receptor (Roopenian and Akilesh (2007) Nat Rev Immunol 7:715-725). The higher the affinity of the antibody to the FcRn at pH 6, the greater the half life of that antibody. Fc-fragment mutations known to stabilize this interaction are summarised in Presta (2008, Curr Opin Immunol 20:460-470).

Therapeutic antibodies can act through several mechanisms upon binding to their target. The binding itself can trigger signal transduction, which can lead to programmed cell death (Chavez-Galan et al. (2009) Cell Mol Immunol 6:15-25). It can also block the interaction of a receptor with its ligand by either binding to the receptor or the ligand. This interruption can cause apoptosis if signals important for survival are affected (Chiu et al. (2007) Blood 109:729-739). With regard to cell-depletion there are two major effector mechanisms known. The first is the complement-dependent cytotoxicity (CDC) towards the target cell. There are three different pathways known. However, in the case of antibodies the important pathway for CDC is the classical pathway which is initiated through the binding of C1q to the constant region of IgG or IgM (Wang and Weiner (2008) Expert Opin Biol Ther 8:759-768).

The second mechanism is called antibody-dependent cellular cytotoxicity (ADCC). This effector function is characterized by the recruitment of immune cells which express Fc-receptors for the respective isotype of the antibody.

ADCC is largely mediated by activating Fc-gamma receptors (FcγR) which are able to bind to IgG molecules either alone or as immune complexes. Mice exhibit three (FcγRI, FcγRIII and FcγRIV) and humans five (FcγRI, FcγRIIA, FcγRIIC, FcγRIIIA and FcγRIIIB) activating Fcγ-receptors. These receptors are expressed on innate immune cells like granulocytes, monocytes, macrophages, dendritic cells and natural killer cells and therefore link the innate with the adaptive immune system. Depending on the cell type there are several modes of action of FcgR-bearing cells upon recognition of an antibody-marked target cell. Granulocytes generally release vasoactive and cytotoxic substances or chemoattractants but are also capable of phagocytosis. Monocytes and macrophages respond with phagocytosis, oxidative burst, cytotoxicity or the release of pro-inflammatory cytokines whereas Natural killer cells release granzymes and perforin and can also trigger cell death through the interaction with FAS on the target cell and their Fas ligand (Nimmerjahn and Ravetch (2008) Nat Rev Immunol 8:34-47; Wang and Weiner (2008) Expert Opin Biol Ther 8:759-768; Chavez-Galan et al. (2009) Cell Mol Immunol 6:15-25).

The antibody-dependent cellular cytotoxicity (ADCC) can also be improved by strengthening the binding of the Fc-domain to activating Fc-gamma receptors (FcγR). This can also be achieved through mutations in the Fc-gamma domain as summarized in Presta (2008, Curr Opin Immunol 20:460-470).

Another way to change the ADCC is manipulation of the sugar moiety present on each IgG at Asn297. Defucolylation and removal of sialic acid from the end of the sugar molecules are known to increase the cytotoxic potential of an antibody (Anthony and Ravetch (2010) J Clin Immunol 30 Suppl 1:S9-14).

Sequence variants of the claimed nucleic acids, proteins and antibodies, for example defined by the claimed % sequence identity, that maintain the said properties of the invention are also included in the scope of the invention. Such variants, which show alternative sequences, but maintain essentially the same binding properties, such as target specificity, as the specific sequences provided are known as functional analogues, or as functionally analogous. Sequence identity relates to the percentage of identical nucleotides or amino acids when carrying out a sequence alignment.

It will be appreciated by those of ordinary skill in the art that, as a result of the degeneracy of the genetic code, there are many nucleotide sequences that encode a polypeptide as described herein. Some of these polynucleotides bear minimal homology or sequence identity to the nucleotide sequence of any native gene. Nonetheless, polynucleotides that vary due to differences in codon usage are specifically contemplated by the present invention. Deletions, substitutions and other changes in sequence that fall under the described sequence identity are also encompassed in the invention.

Protein sequence modifications, which may occur through substitutions, are also included within the scope of the invention. Substitutions as defined herein are modifications made to the amino acid sequence of the protein, whereby one or more amino acids are replaced with the same number of (different) amino acids, producing a protein which contains a different amino acid sequence than the primary protein, preferably without significantly altering the function of the protein. Like additions, substitutions may be natural or artificial. It is well known in the art that amino acid substitutions may be made without significantly altering the protein's function. This is particularly true when the modification relates to a "conservative" amino acid substitution, which is the substitution of one amino acid for another of similar properties. Such "conserved" amino acids can be natural or synthetic amino acids which because of size, charge, polarity and conformation can be substituted without significantly affecting the structure and function of the protein. Frequently, many amino acids may be substituted by conservative amino acids without deleteriously affecting the protein's function.

In general, the non-polar amino acids Gly, Ala, Val, Ile and Leu; the non-polar aromatic amino acids Phe, Trp and Tyr; the neutral polar amino acids Ser, Thr, Cys, Gln, Asn and Met; the positively charged amino acids Lys, Arg and His; the negatively charged amino acids Asp and Glu, represent groups of conservative amino acids. This list is not exhaustive. For example, it is well known that Ala, Gly, Ser and sometimes Cys can substitute for each other even though they belong to different groups.

Substitution variants have at least one amino acid residue in the antibody molecule removed and a different residue inserted in its place. The sites of greatest interest for substitutional mutagenesis include the hypervariable regions, but FR alterations are also contemplated. If such substitutions result in a change in biological activity, then more substantial changes, denominated "exemplary substitutions" in the table immediately below, or as further described below in reference to amino acid classes, may be introduced and the products screened.

Potential Amino Acid Substitutions:

| Original residue | Preferred conservative substitutions | Examples of exemplary substitutions |
|---|---|---|
| Ala (A) | Val | Val; Leu; Ile |
| Asg (R) | Lys | Lys; Gln; Asn |
| Asn (N) | Gln | Gln; His; Asp, Lys; Arg |
| Asp (D) | Glu | Glu; Asn |
| Cys (C) | Ser | Ser; Ala |
| Gln (Q) | Asn | Asn, Glu |
| Glu (E) | Asp | Asp; Gln |
| Gly (G) | Ala | Ala |
| His (H) | Arg | Asn; Gln; Lys; Arg |
| Ile (I) | Leu | Leu; Val; Met; Ala; Phe; Norleucine |
| Leu (L) | Ile | Norleucine; Ile; Val; Met; Ala; Phe |
| Lys (K) | Arg | Arg; Gln; Asn |
| Met (M) | Leu | Leu; Phe; Ile |
| Phe (F) | Tyr | Leu; Val; Ile; Ala; Tyr |
| Pro (P) | Ala | Ala |
| Ser (S) | Thr | Thr |
| Thr (T) | Ser | Ser |
| Trp (W) | Tyr | Tyr; Phe |
| Tyr (Y) | Phe | Trp; Phe; Thr; Ser |
| Val (V) | Leu | Ile; Leu; Met; Phe; Ala; Norleucine |

Substantial modifications in the biological properties of the antibody are accomplished by selecting substitutions that differ significantly in their effect on maintaining (a) the structure of the polypeptide backbone in the area of the substitution, for example, as a sheet or helical conformation, (b) the charge or hydrophobicity of the molecule at the target site, or (c) the bulk of the side chain.

Conservative amino acid substitutions are not limited to naturally occurring amino acids, but also include synthetic amino acids. Commonly used synthetic amino acids are omega amino acids of various chain lengths and cyclohexyl alanine which are neutral non-polar analogs; citrulline and methionine sulfoxide which are neutral non-polar analogs, phenylglycine which is an aromatic neutral analog; cysteic acid which is a negatively charged analog and ornithine which is a positively charged amino acid analog. Like the naturally occurring amino acids, this list is not exhaustive, but merely exemplary of the substitutions that are well known in the art.

The antibodies of the present invention may be produced by transfection of a host cell with an expression vector comprising the coding sequence for the antibody of the invention. An expression vector or recombinant plasmid is produced by placing these coding sequences for the antibody in operative association with conventional regulatory control sequences capable of controlling the replication and expression in, and/or secretion from, a host cell. Regulatory sequences include promoter sequences, e.g., CMV promoter, and signal sequences which can be derived from other known antibodies. Similarly, a second expression vector can be produced having a DNA sequence which encodes a complementary antibody light or heavy chain. In certain embodiments this second expression vector is identical to the first except insofar as the coding sequences and selectable markers are concerned, so to ensure as far as possible that each polypeptide chain is functionally expressed. Alternatively, the heavy and light chain coding sequences for the antibody may reside on a single vector.

A selected host cell is co-transfected by conventional techniques with both the first and second vectors (or simply transfected by a single vector) to create the transfected host cell of the invention comprising both the recombinant or synthetic light and heavy chains. The transfected cell is then cultured by conventional techniques to produce the engineered antibody of the invention. The antibody which includes the association of both the recombinant heavy chain and/or light chain is screened from culture by appropriate assay, such as ELISA or RIA. Similar conventional techniques may be employed to construct other antibodies.

Suitable vectors for the cloning and subcloning steps employed in the methods and construction of the compositions of this invention may be selected by one of skill in the art. For example, the conventional pUC series of cloning vectors may be used. One vector, pUC19, is commercially available. The components of such vectors, e.g. replicons, selection genes, enhancers, promoters, signal sequences and the like, may be obtained from commercial or natural sources or synthesized by known procedures for use in directing the expression and/or secretion of the product of the recombinant DNA in a selected host. Other appropriate expression vectors of which numerous types are known in the art for mammalian, bacterial, insect, yeast, and fungal expression may also be selected for this purpose.

The present invention also encompasses a cell line transfected with a recombinant plasmid containing the coding sequences of the antibodies of the present invention. Host cells useful for the cloning and other manipulations of these cloning vectors are also conventional.

Suitable host cells or cell lines for the expression of the antibodies of the invention include mammalian cells such as NSO, Sp2/0, CHO (e.g. DG44), COS, HEK, a fibroblast cell (e.g., 3T3), and myeloma cells, for example it may be expressed in a CHO or a myeloma cell. Human cells may be used, thus enabling the molecule to be modified with human glycosylation patterns. Alternatively, other prokaryotic or eukaryotic cell lines may be employed. The selection of suitable mammalian host cells and methods for transformation, culture, amplification, screening and product production and purification are known in the art.

In accordance with the present invention there is provided a method of producing an anti-CD269-antibody of the present invention which binds to and neutralises the activity of human CD269 which method comprises the steps of; providing a first vector encoding a heavy chain of the antibody; providing a second vector encoding a light chain of the antibody; transforming a mammalian host cell (e.g. CHO) with said first and second vectors; culturing the host cell of step (c) under conditions conducive to the secretion of the antibody from said host cell into said culture media; recovering the secreted antibody of step (d). Once expressed, the antibody can be assessed for the desired binding properties using methods as described herein.

The invention encompasses immunoconjugates (interchangeably referred to as "antibody-drug conjugates" or "ADCs") comprising an antibody according to the invention as herein described including, but not limited to, an antibody conjugated to one or more cytotoxic agents, such as a chemotherapeutic agent, a drug, a growth inhibitory agent, a toxin (e.g., a protein toxin, an enzymatically active toxin of bacterial, fungal, plant, or animal origin, or fragments thereof), or a radioactive isotope (i.e., a radioconjugate). Techniques for conjugating therapeutic agents to proteins, and in particular to antibodies, such as for the Anti-CD269 Antibody-Drug Conjugates of the present invention, are well-known. (See, e.g., Arnon et al., "Monoclonal Antibodies For Immunotargeting Of Drugs In Cancer Therapy," in Monoclonal Antibodies And Cancer Therapy (Reisfeld et al. eds., Alan R. Liss, Inc., 1985); Hellstrom et al., "Antibodies For Drug Delivery," in Controlled Drug Delivery (Robinson et al. eds., Marcel Dekker, Inc., 2nd ed. 1987); Thorpe, "Antibody Carriers Of Cytotoxic Agents In Cancer Therapy: A Review," in Monoclonal Antibodies '84: Biological And Clinical Applications (Pinchera et al. eds., 1985); "Analysis, Results, and Future Prospective of the Therapeutic Use of Radiolabeled Antibody In Cancer Therapy," in Monoclonal Antibodies For Cancer Detection And Therapy (Baldwin et al. eds., Academic Press, 1995); and Thorpe et al., 1982, Immunol. Rev. 62:119-58. See also, e.g., PCT publication WO 89/12624.)

Typically, the ADC or ADC derivative comprises a linker region between the therapeutic agent and the anti-CD269 antibody or derivative thereof. As noted supra, in typical embodiments, the linker is cleavable under intracellular conditions, such that cleavage of the linker releases the therapeutic agent from the antibody in the intracellular environment. For example, in some embodiments, the linker is cleavable by a cleaving agent that is present in the intracellular environment (e.g., within a lysosome or endosome or caveolae). The linker can be, e.g., a peptidyl linker that is cleaved by an intracellular peptidase or protease enzyme, including, but not limited to, a lysosomal or endosomal protease. In other embodiments, the cleavable linker is pH-sensitive, i.e., sensitive to hydrolysis at certain pH values. Typically, the pH-sensitive linker is hydrolyzable under acidic conditions. In yet other embodiments, the linker is cleavable under reducing conditions (e.g., a disulfide linker). A variety of disulfide linkers are known in the art (See for example Wawrzynczak et al., In Immunoconjugates: Antibody Conjugates in Radioimagery and Therapy of Cancer (C. W. Vogel ed., Oxford U. Press, 1987. See also U.S. Pat. No. 4,880,935.)

Typically, the linker is not substantially sensitive to the extracellular environment. In other, non-mutually exclusive embodiments, the linker promotes cellular internalization. In certain embodiments, the linker promotes cellular internalization when conjugated to the therapeutic agent (i.e., in the milieu of the linker-therapeutic agent moiety of the ADC or ADC derivate as described herein). In yet other embodiments, the linker promotes cellular internalization when conjugated to both the therapeutic agent and the anti-CD269 antibody or derivative thereof (i.e., in the milieu of the ADC or ADC derivative as described herein). A variety of linkers that can be used with the present compositions and methods are described in WO 2004010957 entitled "Drug Conjugates and Their Use for Treating Cancer, An Autoimmune Disease or an Infectious Disease" filed Jul. 31, 2003, and U.S. Provisional Application No. 60/400,403, entitled "Drug Conjugates and their use for treating cancer, an autoimmune disease or an infectious disease", filed Jul. 31, 2002 (the disclosure of which is incorporated by reference herein).

In certain embodiments, an immunoconjugate comprises an antibody as described herein, including but not limited to, an antibody and a chemotherapeutic agent or other toxin. Enzymatically active toxins and fragments thereof that can be used include diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *Momordica charantia* inhibitor, curcin, crotin, *Sapaonaria officinalis* inhibitor, gelonin, mitogellin, restrictocin, phenomycin, enomycin, and the tricothecenes. A variety of radionuclides are available for the production of radioconjugated antibodies.

Antibodies or fragments thereof of the present invention may also be conjugated to one or more toxins, including, but not limited to, a calicheamicin, maytansinoids, dolastatins, aurostatins, a trichothecene, and CC1065, and the derivatives of these toxins that have toxin activity. Suitable cytotoxic agents include, but are not limited to, an auristatin including dovaline-valine-dolaisoleunine-dolaproine-phenylalanine (MMAF) and monomethyl auristatin E (MMAE) as well as ester forms of MMAE, a DNA minor groove binding agent, a DNA minor groove alkylating agent, an enediyne, a lexitropsin, a duocarmycin, a taxane, including paclitaxel and docetaxel, a puromycin, a dolastatin, a maytansinoid, and a *vinca* alkaloid. Specific cytotoxic agents include topotecan, morpholino-doxorubicin, rhizoxin, cyanomorpholino-doxorubicin, dolastatin-10, echinomycin, combretatstatin, chalicheamicin, maytansine, DM-1, DM-4, netropsin. Other suitable cytotoxic agents include antitubulin agents, such as an auristatin, a *vinca* alkaloid, a podophyllotoxin, a taxane, a baccatin derivative, a cryptophysin, a maytansinoid, a combretastatin, or a dolastatin. Antitubulin agent include dimethylvaline-valine-dolaisoleuine-dolaproine-phenylalanine-p-phenylened-iamine (AFP), MMAF, MMAE, auristatin E, vincristine, vinblastine, vindesine, vinorelbine, VP-16, camptothecin, paclitaxel, docetaxel, epothilone A, epothilone B, nocodazole, colchicines, colcimid, estramustine, cemadotin, discodermolide, maytansine, DM-1, DM-4 or eleutherobin.

In some embodiments, the immunoconjugate comprises an antibody conjugated to dolastatins or dolostatin peptidic analogs and derivatives, the auristatins (U.S. Pat. Nos. 5,635,483; 5,780,588). Dolastatins and auristatins have been shown to interfere with microtubule dynamics, GTP hydrolysis, and nuclear and cellular division (Woyke et al. (2001) Antimicrob. Agents and Chemother. 45(12):3580-3584) and have anticancer (U.S. Pat. No. 5,663,149) and antifungal activity (Pettit et al. (1998) Antimicrob. Agents Chemother. 42:2961-2965). The dolastatin or auristatin (which are pentapeptide derivatives of dolastatins) drug moiety may be attached to the antibody through the N (amino) terminus or the C (carboxyl) terminus of the peptidic drug moiety (WO 02/088172). Exemplary auristatin embodiments include the N-terminus linked monomethylauristatin drug moieties DE and DF, disclosed in "Monomethylvaline Compounds Capable of Conjugation to Ligands," U.S. Pat. No. 7,498, 298. As used herein, the abbreviation "MMAE" refers to monomethyl auristatin E. As used herein the abbreviation "MMAF" refers to dovaline-valine-dolaisoleuine-dolaproine-phenylalanine.

Typically, peptide-based drug moieties can be prepared by forming a peptide bond between two or more amino acids and/or peptide fragments. Such peptide bonds can be prepared, for example, according to the liquid phase synthesis method (see E. Schroder and K. Lubke, "The Peptides," volume 1, pp 76-136, 1965, Academic Press) that is well known in the field of peptide chemistry. Maytansinoids may be used as an active agent coupled to the antibody or fragment thereof according to the invention. Maytansinoids are mitototic inhibitors which act by inhibiting tubulin polymerization. Maytansine was first isolated from the east African shrub *Maytenus serrata* (U.S. Pat. No. 3,896,111). Subsequently, it was discovered that certain microbes also produce maytansinoids, such as maytansinol and C-3 maytansinol esters (U.S. Pat. No. 4,151,042). Highly cytotoxic maytansinoid drugs drugs can be prepared from ansamitocin precursors produced by fermentation of microorganisms such as Actinosynnema. Antibody-maytansinoid conjugates are prepared by chemically linking an antibody to a maytansinoid molecule without significantly diminishing the biological activity of either the antibody or the maytansinoid molecule. See, e.g., U.S. Pat. No. 5,208,020. An average of 3-4 maytansinoid molecules conjugated per antibody molecule has shown efficacy in enhancing cytotoxicity of target cells without negatively affecting the function or solubility of the antibody, although even one molecule of toxin/ antibody would be expected to enhance cytotoxicity over the use of naked antibody. Maytansinoids are well known in the art and can be synthesized by known techniques or isolated from natural sources.

Selected examples of the calicheamicin family of antibiotics may be used as an active agent coupled to the antibody or fragment thereof according to the invention. The calicheamicin family of antibiotics is capable of producing double-stranded DNA breaks at sub-picomolar concentrations. For the preparation of conjugates of the calicheamicin family, see U.S. Pat. Nos. 5,712,374, 5,714,586, 5,739,116, 5,767,285, 5,770,701, 5,770,710, 5,773,001, 5,877,296. Another anti-tumor drug that the antibody can be conjugated is QFA which is an antifolate. Both calicheamicin and QFA have intracellular sites of action and do not readily cross the plasma membrane. Therefore, cellular uptake of these agents through antibody mediated internalization greatly enhances their cytotoxic effects.

Other antitumor agents that can be conjugated to the antibodies include BCNU, streptozoicin, vincristine and 5-fluorouracil, the family of agents known collectively LL-E33288 complex described in U.S. Pat. Nos. 5,053,394, 5,770,710, as well as esperamicins (U.S. Pat. No. 5,877, 296). The present invention further contemplates an immunoconjugate formed between an antibody and a compound with nucleolytic activity (e.g., a ribonuclease or a DNA endonuclease such as a deoxyribonuclease; DNase). For selective destruction of the tumor, the antibody may comprise a highly radioactive atom.

A pharmaceutically acceptable carrier in the sense of the present invention may be any non-toxic material that does not significantly interfere in a detrimental sense with the effectiveness of the biological activity of the antibodies of the present invention. Evidently, the characteristics of the carrier will depend on the route of administration. Such a composition may contain, in addition to the active substance and carrier, diluents, fillers, salts, buffers, stabilizers, solubilizers, and other materials well known in the art. Formulation of pharmaceutically-acceptable excipients and carrier solutions is well-known to those of skill in the art, as is the development of suitable dosing and treatment regimens for using the particular compositions described herein in a variety of treatment regimens, including e.g., oral, parenteral, intravenous, intranasal, and intra-muscular administration and formulation.

The medicament, otherwise known as a pharmaceutical composition, containing the active ingredient (antibody or antibody fragment) may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated. The present invention also refers to a pharmaceutical composition for topical application, oral ingestion, inhalation, or cutaneous, subcutaneous, or intravenous injection. A skilled person is aware of the carriers and additives required for particular application forms.

When a therapeutically effective amount of the active substance (antibody or antibody fragment) of the invention is administered by intravenous, cutaneous or subcutaneous injection, the active substance may be in the form of a pyrogen-free, parenterally acceptable aqueous solution.

The invention also relates to administration of a therapeutically relevant amount of antibody as described herein in the treatment of a subject who has the medical disorders as disclosed herein. As used herein, the term "therapeutically effective amount" means the total amount of each active component of the pharmaceutical composition or method that is sufficient to show a meaningful patient benefit. The amount of active substance in the pharmaceutical composition of the present invention will depend upon the nature and severity of the condition being treated, and on the nature of prior treatments which the patient has undergone. Larger doses may be administered until the optimal therapeutic effect is obtained for the patient, and at that point the dosage is not increased further.

The preparation of such parenterally acceptable solutions, having due regard to pH, isotonicity, stability, and the like, is within the skill in the art. A preferred pharmaceutical composition for intravenous, cutaneous, or subcutaneous injection should contain, in addition to the active substance, an isotonic vehicle such as Sodium Chloride Injection, Ringer's Injection, Dextrose Injection, Dextrose and Sodium Chloride Injection, Lactated Ringer's Injection, or other vehicle as known in the art. The pharmaceutical composition of the present invention may also contain stabilizers, preservatives, buffers, antioxidants, or other additives known to those of skill in the art.

The dose of the antibody administered evidently depends on numerous factors well-known in the art such as, e.g., the chemical nature and pharmaceutical formulation of the antibody, and of body weight, body surface, age and sex of the patient, as well as the time and route of administration. For an adult, the dose may exemplarily be between 0.001 µg and 1 g per day, preferably between 0.1 µg and 100 mg per day, more preferably between 1 µg and 100 mg per day, even more preferably between 5 µg and 10 mg per day. In a continuous infusion, the dose may exemplarily be between 0.01 µg and 100 mg, preferably between 1 µg and 10 mg per kilogram body mass per minute.

In another aspect of the present invention there is provided an antibody according to the invention as herein described for use in the treatment of a B-cell mediated or plasma cell mediated disease or antibody mediated disease or disorder selected from Multiple Myeloma (MM), chronic lymphocytic leukemia (CLL), Non-secretory multiple myeloma, Smoldering multiple myeloma, Monoclonal gammopathy of undetermined significance (MGUS), Solitary plasmacytoma (Bone, Extramedullar), Lymphoplasmacytic lymphoma (LPL), Waldenstrom's Macroglobulinemia, Plasma cell leukemia, Primary Amyloidosis (AL), Heavy chain disease, Systemic lupus erythematosus (SLE), POEMS syndrome/osteosclerotic myeloma, Type I and II cryoglobulinemia, Light chain deposition disease, Goodpasture's syndrome, Idiopathic thrombocytopenic purpura (ITP), Acute glomerulonephritis, Pemphigus and Pemphigoid disorders, and Epidermolysis bullosa acquisita; or any Non-Hodgkin's Lymphoma B-cell leukemia or Hodgkin's lymphoma (HL) with BCMA expression or any diseases in which patients develop neutralising antibodies to recombinant protein replacement therapy wherein said method comprises the step of administering to said patient a therapeutically effective amount of the antibody as described herein.

B-cell disorders can be divided into defects of B-cell development/immunoglobulin production (immunodeficiencies) and excessive/uncontrolled proliferation (lymphomas, leukemias). As used herein, B-cell disorder refers to both types of diseases, and methods are provided for treating B-cell disorders with an antibody.

In one aspect of the present invention the disease is Multiple Myeloma.

Use of the antibody as described herein in the manufacture of a medicament for the treatment of diseases and disorders as described herein is also provided.

For example in one aspect of the invention there is provided the use of the antibody as described herein for use in the treatment or prophylaxis of diseases and disorders responsive to modulation (such as inhibiting or blocking) of the interaction between BCMA and the ligands BAFF and APRIL.

In one embodiment of the invention the isolated antibody or antibody fragment is intended for use in the treatment of B lymphocyte cancers, such as Hodgkin's lymphoma.

In one embodiment of the invention the isolated antibody or antibody fragment is intended for use in the treatment of an autoimmune disease, such as a medical disorder associated with inflammation, preferably autoimmune disease with an inflammatory component, whereby the autoimmune disease is selected from Takayasu Arteritis, Giant-cell arteritis, familial Mediterranean fever, Kawasaki disease, Polyarteritis nodosa, cutanous Polyarteritis nodosa, Hepatitis-associated arteritis, Behcet's syndrome, Wegener's granulomatosis, ANCA-vasculitidies, Churg-Strauss syndrome, microscopic polyangiitis, Vasculitis of connective tissue diseases, Hennoch-Schönlein purpura, Cryoglobulinemic vasculitis, Cutaneous leukocytoclastic angiitis, Tropical aortitis, Sarcoidosis, Cogan's syndrome, Wiskott-Aldrich Syndrome, Lepromatous arteritis, Primary angiitis of the CNS, Thromboangiitis obliterans, Paraneoplastic ateritis, Urticaria, Dego's disease, Myelodysplastic syndrome, Eythema elevatum diutinum, Hyperimmunoglobulin D, Allergic Rhinitis, Asthma bronchiale, chronic obstructive pulmonary disease, periodontitis, Rheumatoid Arthritis, atherosclerosis, Amyloidosis, Morbus Chron, Colitis ulcerosa, Autoimmune Myositis, Diabetes mellitus, Multiple sclerosis, Guillain-Barre Syndrome, histiocytosis, Osteoarthritis, atopic dermatitis, periodontitis, chronic rhinosinusitis, Psoriasis, psoriatic arthritis, Microscopic colitis, Pulmonary fibrosis, glomerulonephritis, Whipple's disease, Still's disease, erythema nodosum, otitis, cryoglobulinemia, Sjogren's syndrome, Lupus erythematosus, aplastic anemia, Osteomyelofibrosis, chronic inflammatory demyelinating polyneuropathy, Kimura's disease, systemic sclerosis, chronic periaortitis, chronic prostatitis, idiopathic pulmonary fibrosis, chronic granulomatous disease, Idiopathic achalasia, bleomycin-induced lung inflammation, cytarabine-induced lung inflammation, Autoimmunthrombocytopenia, Autoimmunneutropenia, Autoimmunhemolytic anemia, Autoimmunlymphocytopenia, Chagas' disease, chronic autoimmune thyroiditis, autoimmune hepatitis, Hashimoto's Thyroiditis, atropic thyroiditis, Graves disase, Autoimmune polyglandular syndrome, Autoimmune Addison Syndrome, Pemphigus vulgaris, Pemphigus foliaceus, Dermatitis herpetiformis, Autoimmune alopecia, Vitiligo, Antiphospholipid syndrome, Myasthenia gravis, Stiff-man syndrome, Goodpasture's syndrome, Sympathetic ophthalmia, Folliculitis, Sharp syndrome and/or Evans syndrome, in particular hay fever, periodontitis, atherosclerosis, rheumatoid arthritis, preferably rheumatoid arthritis or multiple sclerosis.

Sequences

Preferred Antibody Sequences of the Invention:

SEQUENCES

| SEQ ID No. | Sequence | Description |
|---|---|---|
| Preferred antibody sequences of the invention: | | |
| SEQ ID No. 1 | QVQLQQSGGGLVQPGGSLKLSCAASGIDFS<u>RYWMS</u>WVR RAPGKGLEWIG<u>EINPDSSTINYAPSLKDKF</u>IISRDNAK NTLYLQMSKVRSEDTALYYCA<u>SLYYDYGDAMDY</u>WGQGT SVTVSS | HC (VH) mouse |
| SEQ ID No. 2 | EVQLVESGGGLVQPGGSLRLSCAASGFTFD<u>DYWMS</u>WVR QAPGKGLEWVG<u>EINPDSSTINYAPSLKGRF</u>TISRDNAK NTLYLQMNSLRAEDTAVYYCA<u>SLYYDYGDAMDY</u>WGQGT LVTVSS | HC partially humanized |
| SEQ ID No. 3 | EVQLVESGGGLVQPGGSLRLSCAASGFTFS<u>RYWMS</u>WVR QAPGKGLVWVG<u>EINPDSSTINYAPSLKDKF</u>TISRDNAK NTLYLQMNSLRAEDTAVYYCA<u>SLYYDYGDAMDY</u>WGQGT LVTVSS | hHC01 |
| SEQ ID No. 4 | EVQLVESGGGLVQPGGSLRLSCAASGFTFSRYWX₁SWV RQAPGKGLVWVGEINPX₂X₃STINYAPSLKDKFTISRD NAKNTLYLQMNSLRAEDTAVYYCA<u>SLYX₄DYGDAX₅DY</u> <u>W</u>GQGTLVTVSS<br>Wherein<br>X₁: I, F, L, V, Y. C, G, A, S, T, preferably I or F;<br>X₂X₃: SS, NS, TS, GS, KS, RS, SD, SN, DE, preferably SS;<br>X₄: Y, L, A, V, F, I, W, preferably Y; and/or<br>X₅: Y, L, F, I, V, A, C, preferably Y | hHC02 |
| SEQ ID No. 5 | EVQLVESGGGLVQPGGSLRLSCAASGFTFSRYX₁MX₂W VRQAPGKGLVX₃VGX₄<u>INPDSSTINYAPSLKDKF</u>TISR DNAKNTLYLQMNSLRAEDTAVYYCASX₅X₆X₇<u>DYGDX₈M</u> <u>DY</u>WGQGTLVTVSS<br>Wherein<br>X₁: W, F, Y, preferred W;<br>X₂: S, T, N, Q, D, E, preferred S;<br>X₃: W, F, Y, preferred W;<br>X₄: E, Q, preferred E;<br>X₅: L, I, V, G, A, preferred L;<br>X₆: Y, X, preferred Y;<br>X₇: Y, F, L, I, V, M, preferred Y; and/or<br>X₈: A, G, V, preferred A | hHC03 |
| SEQ ID No. 6 | EVQLVESGGGLVQPGGSLRLSCAASGFTFS<u>RYW</u> <u>IS</u>WVRQAPGKGLVWVG<u>EINPNSSTINYAPSLKD</u> <u>KF</u>TISRDNAKNTLYLQMNSLRAEDTAVYYCA<u>SL</u> <u>YYDYGDAYDY</u>WGQGTLVTVSS | hHC04 |

-continued

| SEQ ID No. | Sequence | Description |
|---|---|---|
| SEQ ID No. 7 | EVQLVESGGGLVQPGGSLRLSCAASGFTFS<u>RYW</u><br><u>F</u>SWVRQAPGKGLVWVGE<u>INPNSSTINYAPSLKD</u><br><u>K</u>FTISRDNAKNTLYLQMNSLRAEDTAVYYCA<u>SL</u><br><u>YYDYGDAYDYW</u>GQGTLVTVSS | hHC05 |
| SEQ ID No. 8 | EVQLVESGGGLVQPGGSLRLSCAASGFTFS<u>RYW</u><br><u>I</u>SWVRQAPGKGLVWVGE<u>INPSSSTINYAPSLKD</u><br><u>K</u>FTISRDNAKNTLYLQMNSLRAEDTAVYYCA<u>SL</u><br><u>YYDYGDAYDYW</u>GQGTLVTVSS | hHC06 |
| SEQ ID No. 9 | EVQLVESGGGLVQPGGSLRLSCAASGFTFS<u>RYW</u><br><u>F</u>SWVRQAPGKGLVWVGE<u>INPSSSTINYAPSLKD</u><br><u>K</u>FTISRDNAKNTLYLQMNSLRAEDTAVYYCA<u>SL</u><br><u>YYDYGDAYDYW</u>GQGTLVTVSS | hHC07 |
| SEQ ID No. 43 | DIVMTQSQRFMTTSVGDRVSVTC<u>KASQSVDSNV</u><br><u>A</u>WYQQKPRQSPKALIF<u>SASLRFS</u>GVPARFTGSG<br>SGTDFTLTISNLQSEDLAEYFC<u>QQYNNYPLTFG</u><br>AGTKLELKR | LC (VL) mouse |
| SEQ ID No. 10 | DIVMTQSPATLSVSVGDEVTLTC<u>KASQSVDSNVA</u>WYQQ<br>KPGQAPKLLIY<u>SDDLRFS</u>GVPARFSGSGSGTDFTLTIS<br>SLQSEDFAVYYC<u>QQYNNYPLTFG</u>AGTKLELKR | LC partially humanized |
| SEQ ID No. 11 | E IVMTQSPATLSVSPGERATLSC<u>KASQSVDSNVA</u>WYQQ<br>KPGQAPRALIY<u>SASLRFS</u>GIPARFSGSGSGTEFTLTIS<br>SL QSEDFAVYYC<u>QQYNNYPLTFG</u>AGTKLELKR | hLC01 |
| SEQ ID No. 12 | EIVMTQSPATLSVSPGERATLSC<u>KASQSVX₁X₂NVAWY</u><br>QQKPGQAPRALIY<u>SASLRFS</u>GIPARFSGSGSGTEFTLT<br>ISSLQSEDFAVYYC<u>QQYNNYPLTFG</u>AGTKLELKR<br>Wherein:<br>X₁X₂: ES, SS, TS, QS, HS, DH, preferably ES. | hLC02 |
| SEQ ID No. 13 | EIVMTQSPATLSVSPGERATLSC<u>KASQSVDX₁X₂VX₃WX₄</u><br>QQKPGQAPRALIX₅<u>X₆AX₇X₈RX₉S</u>GIPARFSGSX₁₀X₁₁<br>GTEFTLTISSLQSEDFAVYYC<u>X₁₂QX₁₃NNX₁₄PX₁₅TFG</u><br>AGTKLELKR<br>Wherein:<br>X₁: S, H, T, N, D, Q;<br>X₂: N, E, Q;<br>X₃: A, G, V, S, T, L, I;<br>X₄: Y, F, L, I, V, A, G;<br>X₅: Y, F, L;<br>X₆: S, T;<br>X₇: S, T, D, N, H, E, Q;<br>X₈: L, V, I, M;<br>X₉: F, L, I, V, Y, M;<br>X₁₀: G, X;<br>X₁₁: S, X;<br>X₁₂: Q, V, L, I, M;<br>X₁₃: Y, F, L, I, Q;<br>X₁₄: Y, F, R, Q, K; and/or<br>X₁₅: L, I, V, F | hLC03 |
| SEQ ID No. 14 | EIVMTQSPATLSVSPGERATLSC<u>KASQSVESNVA</u>WYQQ<br>KPGQAPRALIY<u>SASLRFS</u>GIPARFSGSGSGTEFTLTIS<br>SLQSEDFAVYYC<u>QQYNNYPLTFG</u>AGTKLELKR | hLC04 |
| SEQ ID No. 15 | RYWX₁S<br>Wherein:<br>X₁: I, F, L, V, Y. C, G, A, S, T, preferably I or F | H-CDR1 PTM |
| SEQ ID No. 16 | EINPX₂X₃STINYAPSLKDK<br>Wherein:<br>X₂X₃: SS, NS, TS, GS, KS, RS, SD, SN, DE,<br>preferably SS | H-CDR2 PTM |
| SEQ ID No. 17 | SLYX₄DYGDAX₅DYW<br>Wherein:<br>X₄: Y, L, A, V, F, I, W, preferably Y; and/or<br>X₅: Y, L, F, I, V, A, C, preferably Y | H-CDR3 PTM |
| SEQ ID No. 18 | RYWIS | H-CDR1 PTM a |

-continued

| SEQUENCES | | |
|---|---|---|
| SEQ ID No. | Sequence | Description |
| SEQ ID No. 19 | RYWFS | H-CDR1 PTM b |
| SEQ ID No. 20 | EINPNSSTINYAPSLKDK | H-CDR2 PTM a |
| SEQ ID No. 21 | EINPSSSTINYAPSLKDK | H-CDR2 PTM b |
| SEQ ID No. 22 | SLYYDYGDAYDYW | H-CDR3 PTM a |
| SEQ ID No. 23 | KASQSVX$_1$X$_2$NVA<br>Wherein:<br>X$_1$X$_2$: ES, SS, TS, QS, HS, DH, preferably ES | L-CDR1 PTM |
| SEQ ID No. 24 | SASLRFS | L-CDR2 PTM |
| SEQ ID No. 25 | QQYNNYPLTFG | L-CDR3 PTM |
| SEQ ID No. 26 | KASQSVDSNVA | L-CDR1 PTM a |
| SEQ ID No. 27 | EVQLVESGGGLVQPGGSLRLSCAASGFTFSRYWMSWVR<br>QAPGKGLVWVGEINPDSSTINYAPSLKDKFTISRDNAK<br>NTLYLQMNSLRAEDTAVYYCASLYYDYGDAMDYWGQGT<br>LVTVSSASTKGPSVFPLAPSSKSTSGGTAALGCLVKDY<br>FPEPVTVSWNSGALTSGVHTFPAVLQSSGLYSLSSVVT<br>VPSSSLGTQTYICNVNHKPSNTKVDKRVEPKSCDKTHT<br>CPPCPAPELLGGPSVFLFPPKPKDTLMISRTPEVTCVV<br>VDVSHEDPEVKFNWYVDGVEVHNAKTKPREEQYNSTYR<br>VVSVLTVLHQDWLNGKEYKCKVSNKALPAPIEKTISKA<br>KGQPREPQVYTLPPSREEMTKNQVSLTCLVKGFYPSDI<br>AVEWESNGQPENNYKTTPPVLDSDGSFFLYSKLTVDKS<br>RWQQGNVFSCSVMHEALHNHYTQKSLSLSPGK | Full length<br>humanized HC |
| SEQ ID No. 28 | EVQLVESGGGLVQPGGSLRLSCAASGFTFSRYWFSWVR<br>QAPGKGLVWVGEINPSSSTINYAPSLKDKFTISRDNAK<br>NTLYLQMNSLRAEDTAVYYCASLYYDYGDAYDYWGQGT<br>LVTVSSASTKGPSVFPLAPSSKSTSGGTAALGCLVKDY<br>FPEPVTVSWNSGALTSGVHTFPAVLQSSGLYSLSSVVT<br>VPSSSLGTQTYICNVNHKPSNTKVDKRVEPKSCDKTHT<br>CPPCPAPELLGGPSVFLFPPKPKDTLMISRTPEVTCVV<br>VDVSHEDPEVKFNWYVDGVEVHNAKTKPREEQYNSTYR<br>VVSVLTVLHQDWLNGKEYKCKVSNKALPAPIEKTISKA<br>KGQPREPQVYTLPPSREEMTKNQVSLTCLVKGFYPSDI<br>AVEWESNGQPENNYKTTPPVLDSDGSFFLYSKLTVDKS<br>RWQQGNVFSCSVMHEALHNHYTQKSLSLSPGK | Full length<br>humanized HC with<br>PTM mutations 1<br>(FSY) |
| SEQ ID No. 29 | EVQLVESGGGLVQPGGSLRLSCAASGFTFSRYWISWVR<br>QAPGKGLVWVGEINPSSSTINYAPSLKDKFTISRDNAK<br>NTLYLQMNSLRAEDTAVYYCASLYYDYGDAYDYWGQGT<br>LVTVSSASTKGPSVFPLAPSSKSTSGGTAALGCLVKDY<br>FPEPVTVSWNSGALTSGVHTFPAVLQSSGLYSLSSVVT<br>VPSSSLGTQTYICNVNHKPSNTKVDKRVEPKSCDKTHT<br>CPPCPAPELLGGPSVFLFPPKPKDTLMISRTPEVTCVV<br>VDVSHEDPEVKFNWYVDGVEVHNAKTKPREEQYNSTYR<br>VVSVLTVLHQDWLNGKEYKCKVSNKALPAPIEKTISKA<br>KGQPREPQVYTLPPSREEMTKNQVSLTCLVKGFYPSDI<br>AVEWESNGQPENNYKTTPPVLDSDGSFFLYSKLTVDKS<br>RWQQGNVFSCSVMHEALHNHYTQKSLSLSPGK | Full length<br>humanized HC with<br>PTM mutations 2<br>(ISY) |
| SEQ ID No. 30 | EIVMTQSPATLSVSPGERATLSCKASQSVDSNVAWYQQ<br>KPGQAPRALIYSASLRFSGIPARFSGSGSGTEFTLTIS<br>SLQSEDFAVYYCQQYNNYPLTFGAGTKLELKRTVAAPS<br>VFIFPPSDEQLKSGTASVVCLLNNFYPREAKVQWKVDN<br>ALQSGNSQESVTEQDSKDSTYSLSSTLTLSKADYEKHK<br>VYACEVTHQGLSSPVTKSFNRGEC | Full length<br>humanized LC |
| SEQ ID No. 31 | EIVMTQSPATLSVSPGERATLSCKASQSVESNVAWYQQ<br>KPGQAPRALIYSASLRFSGIPARFSGSGSGTEFTLTIS<br>SLQSEDFAVYYCQQYNNYPLTFGAGTKLELKRTVAAPS<br>VFIFPPSDEQLKSGTASVVCLLNNFYPREAKVQWKVDN<br>ALQSGNSQESVTEQDSKDSTYSLSSTLTLSKADYEKHK<br>VYACEVTHQGLSSPVTKSFNRGEC | Full length<br>humanized LC with<br>PTM mutations |
| Preferred Nucleotide Sequences | | |
| SEQ ID No. 32 | GAATTCCACCATGGGATGGTCATGTATCATCCTTTTTCTA<br>GTAGCAACTGCAACCGGTGTCCACAGTGAAGTGCAGCTGG<br>TCGAATCTGGAGGAGGCCTGGTTCAGCCTGGTGGCAGCCT | Full length<br>humanized HC |

| SEQ ID No. | Sequence | Description |
|---|---|---|
| | TAGGCTCTCTTGTGCAGCCTCTGGCTTTACCTTCTCACGG<br>TATTGGATGAGCTGGGTGAGACAGGCTCCAGGGAAAGGTC<br>TGGTGTGGGTAGGGGAGATAAACCCCGATAGCAGCACGAT<br>CAACTATGCTCCGTCACTGAAAGACAAGTTCACCATTTCC<br>CGCGATAATGCCAAGAACACTCTCTACTTGCAGATGAATT<br>CCCTTCGAGCCGAGGATACAGCGGTGTACTACTGCGCCAG<br>TCTGTACtacgactATGGGGACGCAATGGACTATTGGGGA<br>CAAGGCACACTGGTGACTGTTAGCTCCGCGTCGACCAAGG<br>GCCCATCGGTCTTCCCCCTGGCACCCTCCTCCAAGAGCAC<br>CTCTGGGGGCACAGCGGCCCTGGGCTGCCTGGTCAAGGAC<br>TACTTCCCCGAACCTGTGACGGTCTCGTGGAACTCAGGCG<br>CCCTGACCAGCGGCGTGCACACCTTCCCGGCTGTCCTACA<br>GTCCTCAGGACTCTACTCCCTCAGCAGCGTGGTGACCGTG<br>CCCTCCAGCAGCTTGGGCACCCAGACCTACATCTGCAACG<br>TGAATCACAAGCCCAGCAACACCAAGGTGGACAAGAGAGT<br>TGAGCCCAAATCTTGTGACAAAACTCACACATGCCCACCG<br>TGCCCAGCACCTGAACTCCTGGGGGGACCGTCAGTCTTCC<br>TCTTCCCCCCAAAACCCAAGGACACCCTCATGATCTCCCG<br>GACCCCTGAGGTCACATGCGTGGTGGTGGACGTGAGCCAC<br>GAAGACCCTGAGGTCAAGTTCAACTGGTACGTGGACGGCG<br>TGGAGGTGCATAATGCCAAGACAAAGCCGCGGGAGGAGCA<br>GTACAACAGCACGTACCGTGTGGTCAGCGTCCTCACCGTC<br>CTGCACCAGGACTGGCTGAATGGCAAGGAGTACAAGTGCA<br>AGGTCTCCAACAAAGCCCTCCCAGCCCCCATCGAGAAAAC<br>CATCTCCAAAGCCAAAGGGCAGCCCCGAGAACCACAGGTG<br>TACACCCTGCCCCCATCCCGGGAGGAGATGACCAAGAACC<br>AGGTCAGCCTGACCTGCCTGGTCAAAGGCTTCTATCCCAG<br>CGACATCGCCGTGGAGTGGGAGAGCAATGGGCAGCCGGAG<br>AACAACTACAAGACCACGCCTCCCGTGCTGGACTCCGACG<br>GCTCCTTCTTCCTCTATAGCAAGCTCACCGTGGACAAGAG<br>CAGGTGGCAGCAGGGGAACGTCTTCTCATGCTCCGTGATG<br>CATGAGGCTCTGCACAACCACTACACGCAGAAGAGCCTCT<br>CCCTGTCCCCGGGTAAATGAGTGCGACGGCCGGGCGGCGG<br>CGGCGGATCC | |
| SEQ ID No. 33 | GAATTCCACCATGGGATGGTCATGTATCATCCTTTTTCTA<br>GTAGCAACTGCAACCGGTGTCCACAGTGAAGTGCAGCTGG<br>TCGAATCTGGAGGAGGCCTGGTTCAGCCTGGTGGCAGCCT<br>TAGGCTCTCTTGTGCAGCCTCTGGCTTTACCTTCTCACGG<br>TATTGGTTCAGCTGGGTGAGACAGGCTCCAGGGAAAGGTC<br>TGGTGTGGGTAGGGGAGATAAACCCCAGCAGCAGCACGAT<br>CAACTATGCTCCGTCACTGAAAGACAAGTTCACCATTTCC<br>CGCGATAATGCCAAGAACACTCTCTACTTGCAGATGAATT<br>CCCTTCGAGCCGAGGATACAGCGGTGTACTACTGCGCCAG<br>TCTGTACTACGACTATGGGGACGCATACGACTATTGGGGA<br>CAAGGCACACTGGTGACTGTTAGCTCCGCGTCGACCAAGG<br>GCCCATCGGTCTTCCCCCTGGCACCCTCCTCCAAGAGCAC<br>CTCTGGGGGCACAGCGGCCCTGGGCTGCCTGGTCAAGGAC<br>TACTTCCCCGAACCTGTGACGGTCTCGTGGAACTCAGGCG<br>CCCTGACCAGCGGCGTGCACACCTTCCCGGCTGTCCTACA<br>GTCCTCAGGACTCTACTCCCTCAGCAGCGTGGTGACCGTG<br>CCCTCCAGCAGCTTGGGCACCCAGACCTACATCTGCAACG<br>TGAATCACAAGCCCAGCAACACCAAGGTGGACAAGAGAGT<br>TGAGCCCAAATCTTGTGACAAAACTCACACATGCCCACCG<br>TGCCCAGCACCTGAACTCCTGGGGGGACCGTCAGTCTTCC<br>TCTTCCCCCCAAAACCCAAGGACACCCTCATGATCTCCCG<br>GACCCCTGAGGTCACATGCGTGGTGGTGGACGTGAGCCAC<br>GAAGACCCTGAGGTCAAGTTCAACTGGTACGTGGACGGCG<br>TGGAGGTGCATAATGCCAAGACAAAGCCGCGGGAGGAGCA<br>GTACAACAGCACGTACCGTGTGGTCAGCGTCCTCACCGTC<br>CTGCACCAGGACTGGCTGAATGGCAAGGAGTACAAGTGCA<br>AGGTCTCCAACAAAGCCCTCCCAGCCCCCATCGAGAAAAC<br>CATCTCCAAAGCCAAAGGGCAGCCCCGAGAACCACAGGTG<br>TACACCCTGCCCCCATCCCGGGAGGAGATGACCAAGAACC<br>AGGTCAGCCTGACCTGCCTGGTCAAAGGCTTCTATCCCAG<br>CGACATCGCCGTGGAGTGGGAGAGCAATGGGCAGCCGGAG<br>AACAACTACAAGACCACGCCTCCCGTGCTGGACTCCGACG<br>GCTCCTTCTTCCTCTATAGCAAGCTCACCGTGGACAAGAG<br>CAGGTGGCAGCAGGGGAACGTCTTCTCATGCTCCGTGATG<br>CATGAGGCTCTGCACAACCACTACACGCAGAAGAGCCTCT<br>CCCTGTCCCCGGGTAAATGAGTGCGACGGCCGGGCGGCGG<br>CGGCGGATCC | Full length<br>humanized HC with<br>PTM mutations 1 |
| SEQ ID No. 34 | GAATTCCACCATGGGATGGTCATGTATCATCCTTTTTCTA<br>GTAGCAACTGCAACCGGTGTCCACAGTGAAGTGCAGCTGG | Full length<br>humanized HC with |

| SEQ ID No. | Sequence | Description |
|---|---|---|
| | TCGAATCTGGAGGAGGCCTGGTTCAGCCTGGTGGCAGCCT<br>TAGGCTCTCTTGTGCAGCCTCTGGCTTTACCTTCTCACGG<br>TATTGGaTCAGCTGGGTGAGACAGGCTCCAGGGAAAGGTC<br>TGGTGTGGGTAGGGGAGATAAACCCCAGCAGCAGCACGAT<br>CAACTATGCTCCGTCACTGAAAGACAAGTTCACCATTTCC<br>CGCGATAATGCCAAGAACACTCTCTACTTGCAGATGAATT<br>CCCTTCGAGCCGAGGATACAGCGGTGTACTACTGCGCCAG<br>TCTGTACTACGACTATGGGGACGCATACGACTATTGGGGA<br>CAAGGCACACTGGTGACTGTTAGCTCCGCGTCGACCAAGG<br>GCCCATCGGTCTTCCCCCTGGCACCCTCCTCCAAGAGCAC<br>CTCTGGGGGCACAGCGGCCCTGGGCTGCCTGGTCAAGGAC<br>TACTTCCCCGAACCTGTGACGGTCTCGTGGAACTCAGGCG<br>CCCTGACCAGCGGCGTGCACACCTTCCCGGCTGTCCTACA<br>GTCCTCAGGACTCTACTCCCTCAGCAGCGTGGTGACCGTG<br>CCCTCCAGCAGCTTGGGCACCCAGACCTACATCTGCAACG<br>TGAATCACAAGCCCAGCAACACCAAGGTGGACAAGAGAGT<br>TGAGCCCAAATCTTGTGACAAAACTCACACATGCCCACCG<br>TGCCCAGCACCTGAACTCCTGGGGGGACCGTCAGTCTTCC<br>TCTTCCCCCCAAAACCCAAGGACACCCTCATGATCTCCCG<br>GACCCCTGAGGTCACATGCGTGGTGGTGGACGTGAGCCAC<br>GAAGACCCTGAGGTCAAGTTCAACTGGTACGTGGACGGCG<br>TGGAGGTGCATAATGCCAAGACAAAGCCGCGGGAGGAGCA<br>GTACAACAGCACGTACCGTGTGGTCAGCGTCCTCACCGTC<br>CTGCACCAGGACTGGCTGAATGGCAAGGAGTACAAGTGCA<br>AGGTCTCCAACAAAGCCCTCCCAGCCCCCATCGAGAAAAC<br>CATCTCCAAAGCCAAAGGGCAGCCCCGAGAACCACAGGTG<br>TACACCCTGCCCCCATCCCGGGAGGAGATGACCAAGAACC<br>AGGTCAGCCTGACCTGCCTGGTCAAAGGCTTCTATCCCAG<br>CGACATCGCCGTGGAGTGGGAGAGCAATGGGCAGCCGGAG<br>AACAACTACAAGACCACGCCTCCCGTGCTGGACTCCGACG<br>GCTCCTTCTTCCTCTATAGCAAGCTCACCGTGGACAAGAG<br>CAGGTGGCAGCAGGGGAACGTCTTCTCATGCTCCGTGATG<br>CATGAGGCTCTGCACAACCACTACACGCAGAAGAGCCTCT<br>CCCTGTCCCCGGGTAAATGAGTGCGACGGCCGGGCGGCGG<br>CGGCGGATCC | PTM mutations 2 |
| SEQ ID No. 35 | GAATTCCACCATGGGATGGtcATGTATCATCCTTTTTCTA<br>GTAGCAACTGCAACCGGTGTACACTCCGAGATCGTGATGA<br>CCCAGTCTCCTGCTACCCTGAGCGTTTCTCCCGGTGAAAG<br>GGCCACACTCAGCTGCAAAGCCTCTCAAAGCGTGGACAGC<br>AATGTCGCCTGGTATCAGCAGAAACCTGGCCAAGCTCCGA<br>GAGCACTGATCTATTCCGCGTCATTGCGCTTTTCCGGCAT<br>ACCAGCACGGTTTAGTGGCTCAGGGAGTGGGACTGAGTTC<br>ACTCTGACGATTAGCTCCCTTCAGTCAGAGGATTTCGCCG<br>TGTACTACTGTCAGCAGTACAACAACTATCCCCTCACATT<br>CGGAGCTGGAACCAAGCTGGAACTGAAGCGTACGGTGGCT<br>GCACCATCTGTCTTCATCTTCCCGCCATCTGATGAGCAGT<br>TGAAATCTGGAACTGCCTCTGTTGTGTGCCTGCTGAATAA<br>CTTCTATCCCAGAGAGGCCAAAGTACAGTGGAAGGTGGAT<br>AACGCCCTCCAATCGGGTAACTCCCAGGAGAGTGTCACAG<br>AGCAGGACAGCAAGGACAGCACCTACAGCCTCAGCAGCAC<br>CCTGACGCTGAGCAAAGCAGACTACGAGAAACACAAAGTC<br>TACGCCTGCGAAGTCACCCATCAGGGCCTGAGCTCGCCCG<br>TCACAAAGAGCTTCAACAGGGGAGAGTGTTAGGGATCC | Full length<br>humanized LC |
| SEQ ID No. 36 | GAATTCCACCATGGGATGGtcATGTATCATCCTTTTTCTA<br>GTAGCAACTGCAACCGGTGTACACTCCGAGATCGTGATGA<br>CCCAGTCTCCTGCTACCCTGAGCGTTTCTCCCGGTGAAAG<br>GGCCACACTCAGCTGCAAAGCCTCTCAAAGCGTGGAGAGC<br>AATGTCGCCTGGTATCAGCAGAAACCTGGCCAAGCTCCGA<br>GAGCACTGATCTATTCCGCGTCATTGCGCTTTTCCGGCAT<br>ACCAGCACGGTTTAGTGGCTCAGGGAGTGGGACTGAGTTC<br>ACTCTGACGATTAGCTCCCTTCAGTCAGAGGATTTCGCCG<br>TGTACTACTGTCAGCAGTACAACAACTATCCCCTCACATT<br>CGGAGCTGGAACCAAGCTGGAACTGAAGCGTACGGTGGCT<br>GCACCATCTGTCTTCATCTTCCCGCCATCTGATGAGCAGT<br>TGAAATCTGGAACTGCCTCTGTTGTGTGCCTGCTGAATAA<br>CTTCTATCCCAGAGAGGCCAAAGTACAGTGGAAGGTGGAT<br>AACGCCCTCCAATCGGGTAACTCCCAGGAGAGTGTCACAG<br>AGCAGGACAGCAAGGACAGCACCTACAGCCTCAGCAGCAC<br>CCTGACGCTGAGCAAAGCAGACTACGAGAAACACAAAGTC<br>TACGCCTGCGAAGTCACCCATCAGGGCCTGAGCTCGCCCG<br>TCACAAAGAGCTTCAACAGGGGAGAGTGTTAGGGATCC | Full length<br>humanized LC with<br>PTM mutations |

SEQUENCES

| SEQ ID No. | Sequence | Description |
|---|---|---|
| Preferred sequences of the invention pertaining to CD269 (BCMA): | | |
| SEQ ID No. 37 | MSPILGYWKIGLVQPTRLLLEYLEEKYEEHLYERDEGDK<br>WRNKKFELGLEFPNLPYYIDGDVKLTQSMAIIRYIADKHN<br>MLGGCPKERAEISMLEGAVLDIRYGVSRIAYSKDFETLKV<br>DFLSKLPEMLKMFEDRLCHKTYLNGDHVTHPDFMLYDALD<br>VVLYMDPMCLDAFPKLVCFKKRIEAIPQIDKYLKSSKYIA<br>WPLQGWQATFGGGDHPPKSDLVPRGSMAGQCSQNEYFDSL<br>LHACIPCQLRCSSNTPPLTCQRYCNASVTNSVKGTNALEH<br>HHHHH | GST-BCMA-His |
| SEQ ID No. 38 | MAGQCSQNEYFDSLLHACIPCQLRCSSNTPPLTCQRYCNA<br>SVTNSVKGTNALE | BCMA extracellular domain |
| SEQ ID No. 39 | MLQMAGQCSQNEYFDSLLHACIPCQLRCSSNTPPLTCQRY<br>CNASVTNSVKGTNALE | BCMA N-terminus sequence |
| SEQ ID No. 40 | YFDSLLHACIPCQLRCSSNT | BCMA antibody epitope - amino acids 13 to 32 of BCNA |
| Preferred generalized amino acid sequences comprising the humanized sequence modifications: | | |
| SEQ ID No. 41 | $X_1$VQLX$_2$X$_3$SGGGLVQPGGSLX$_4$LSCAASGX$_5$X$_6$FX$_7$X$_8$YWZ$_1$<br>SWVRX$_9$APGKGLEWX$_{10}$GEINPZ$_2$SSTINYAPSLKX$_{11}$X$_{12}$F<br>X$_{13}$ISRDNAKNTLYLQMX$_{14}$X$_{15}$X$_{16}$RX$_{17}$EDTAX$_{18}$YYCASLY<br>YDYGDAZ$_3$DYWGQGTX$_{19}$*VTVSS*<br>wherein XI: Q, E; X2: Q, V; X3: Q, E: X4: K. R: X5: I,<br>F; X6: D, T: X7: S, D: X8: R, D: X9: R, Q: X10: I, V;<br>X11: D. G: X12: K. R; X13: I, T; X14: S, N; X15: K, S;<br>X16: V, L; X17: S, A; X18: L, V; X19: S, L; and<br>wherein at least one of Z$_1$: 1 or F; Z2: S and/or Z3: Y. | General sequence for humanized HC antibodies comprising the PTM deletion modifications |
| SEQ ID No. 42 | $X_1$IVMTQSX$_2$X$_3$X$_4$X$_5$X$_6$X$_7$SVGDX$_8$VX$_9$X$_{10}$TCKASQSVESNV<br>AWYQQKPX$_{11}$QX$_{12}$PKX$_{13}$LIX$_{14}$SX$_{15}$X$_{16}$LRFSGVPARFX$_{17}$G<br>SGSGTDFTLTXSX$_{18}$LQSEDX$_{19}$AX$_{20}$YX$_{21}$CQQYNNYPLTF<br>GAGTKLELKR<br>wherein X1: D, E; X2: Q, P; X3: R, A; X4: F, T; X5:<br>M, L; X6: T, S; X7: T, V; X8: R, E; X9: S, T; X10: V,<br>L; X11: R, G; X12: S, A; X13: A, L; X14: F, Y; X15:<br>A, D; X16: S, D; X17: T, S; X18: N, S; X19: L, F;<br>X20: E, V; X21: F, Y | General sequence for humanized LC antibodies comprising the PTM deletion modifications |

EXAMPLES

The invention is demonstrated by way of the examples disclosed herein. The examples provided herein represent only particular embodiments of the invention and are not intended to limit the scope of the invention. The examples are to be considered as providing a further description of possible and potentially preferred embodiments that enhance the technical support of one or more non-limiting embodiments.

Although the examples with respect to crystallization of the antibody-epitope complex and the in vitro and in vivo anti-tumor effect was carried out using the original chimeric antibody J22.9-xi, the inventors assert that these technical effects are maintained in the humanized variants of the present invention, due to the maintenance of binding characteristics in the humanized variants compared to the original chimeric antibody tested. The data provided from the chimeric antibody is therefore provided as reference material and an indication of the industrial applicability and usefulness of the claimed human variants. Preliminary biological data indicates comparable effects between J22.9-xi and the humanized variants.

Binding and Blocking Characteristics of the J22.9-xi and BCMA Interaction

The novel chimeric antibody (J22.9-xi) binds to the extracellular domain of human CD269 (BCMA, TNFRSF17). This was initially ascertained by ELISA and flow cytometry on the human multiple myeloma cell line MM.1S (FIG. 1a,b). The affinity of J22.9-xi to BCMA was determined using surface plasmon resonance (SPR). The mean Kd is 54 pM as shown in FIG. 1c.

BCMA is known to trigger signals important for the survival of multiple myeloma and plasma cells in vivo through interaction with its ligands BAFF and/or APRIL (Mackay F et al. (2003) Annu Rev Immunol 21:231-264). An in vitro blocking assay was therefore performed with the extracellular domain of human BCMA and recombinant BAFF. The binding of J22.9-xi to BCMA clearly blocks the interaction between the receptor and its ligand BAFF. Using the isotype control antibody instead of J22.9-xi, recombinant BAFF binding to BCMA is unaffected (FIG. 1d).

The Crystal Structure of the J22.9-xi-Fab-BCMA-Complex Reveals an Extensive Binding Interface with BCMA Fab fragments prepared from J22.9-xi were crystallized in complex with the purified 46 amino acid residue BCMA extracellular domain and the complex structure solved to 1.9 angstroms resolution. High quality electron density is observable for residues 6 to 41 of BCMA and shows an extensive interaction with J22.9-xi, primarily with the light chain of the antibody (FIG. 2B). This interface, which buries 740.4 square angstroms and involves one third of the BCMA residues, covers 12 of 16 residues of the identical epitope observed in the crystal structures of BMCA complexes with APRIL and sTALL1 (also known as BAFF), including the conserved DxL motif (Gordon N C, et al. (2003), BAFF/BlysS receptor 3 comprises a minimal TNF receptor-like module that encodes a highly focused ligand-binding site. Biochemistry 42(20): 5977-83, and Patel D R, et al. (2004), Engineering an APRIL-specific B Cell Maturation Antigen. JBC 279(16): 16727-35), providing clear rationalization of the blocking effect seen in the in vitro assays with BAFF (FIG. 2A). The interaction with J22.9-xi additionally comprises a direct side chain contact with Ala20 and Pro23 in BCMA, residues not part of the binding epitope covered by BAFF and APRIL, and several water-mediated hydrogen bonds. The overall conformation of BCMA in all three structures is very similar, with a C-alpha rmsd of 1.4 angstroms between the J22.9-xi and APRIL complexes and 1.5 angstroms between the J22.9-xi and sTALL1 complexes; the respective C-alpha rmsds for the J22.9-xi BCMA binding epitope (residues 13-30) are 0.98 and 0.88 angstroms. Although recognizing the same BCMA epitope having the DxL motif at its core, the binding site of J22.9-xi is very different from those of sTALL1 and APRIL, as is the collection of interactions comprising the interface.

As can be seen in FIG. 2B and Tables 1 and 2, 19 amino acids from J22.9-xi (6 from the heavy chain (Table 1), 13 from the light chain (Table 2)) form direct linkages to 12 residues from the extracellular domain of CD269.

TABLE 1

Amino acid interaction list between heavy chain of J22.9-xi and BCMA. These interaction lists were generated using the software PDBsum (Laskowski R A (2009)).

| Heavy chain | | CD269 |
|---|---|---|
| Trp33 | > | His19 |
| Glu50 | > | His19 |
| Leu99 | > | Leu17 |
|  | > | Leu18 |
| Tyr100 |  | Leu18 |
| Tyr101 | > | Ala20 |
|  | > | Ile22 |
|  | > | Pro23 |
| Ala106 | > | Leu18 |

TABLE 2

Amino acid interaction list between light chain of J22.9-xi and BCMA. These interaction lists were generated using the software PDBsum (Laskowski R A (2009)).

| Light chain | | CD269 |
|---|---|---|
| Ser31 | > | Arg27 |
|  |  | Thr32 |
| Ala34 | > | Leu17 |
| Tyr36 | > | Leu17 |
| Phe49 | > | Leu18 |
|  |  | Asp15 |
| Ser50 | > | Tyr13 |
|  |  | Asp15 |
|  |  | Arg27 |
| Ser52 | > | Arg27 |
| Ser67 | > | Thr32 |
| Leu53 | > | Tyr13 |
|  |  | Leu26 |
|  |  | Arg27 |
| Phe55 | > | Leu18 |
| Gln89 | > | Leu17 |

TABLE 2-continued

Amino acid interaction list between light chain of J22.9-xi and BCMA. These interaction lists were generated using the software PDBsum (Laskowski R A (2009)).

| Light chain | | CD269 |
|---|---|---|
| Tyr91 | > | Asp15 |
|  |  | Ser16 |
|  |  | Leu17 |
| Tyr94 | > | His19 |
| Leu96 | > | Leu17 |

TABLE 3

Interaction list of the residues involved in CD269:APRIL und CD269:BAFF binding (residues NOT directly contacted by J22.9 are underlined). These interaction lists were generated using the software PDBsum (Laskowski R A (2009)).

| | CD269 |
|---|---|
| APRIL | |
| Asp121 | Leu35 |
| Asp123 | Pro33 |
|  | Pro34 |
|  | Leu35 |
| Asp164 | Asn31 |
| Thr166 | Arg27 |
|  | Ser30 |
| Phe167 | Tyr13 |
|  | Leu18 |
|  | Ile22 |
|  | Leu26 |
|  | Arg27 |
|  | Asn31 |
| Thr168 | Leu18 |
|  | Leu26 |
| Met169 | Leu17 |
| Gly170 | Leu17 |
|  | His19 |
| Gln171 | Leu17 |
| Arg186 | Leu17 |
|  | Leu18 |
|  | His19 |
| Cys187 | Leu17 |
| Ile188 | Asp15 |
|  | Leu17 |
|  | Leu18 |
| Asp196 | Leu26 |
| Arg197 | Leu26 |
| Tyr199 | Leu18 |
| Pro221 | Leu17 |
|  | His19 |
| Arg222 | Asp15 |
|  | Leu17 |
|  | Arg27 |
| Asn224 | Thr32 |
| Lys226 | Asn31 |
| His232 | His19 |
| BAFF | |
| Tyr22 | Ser16 |
| Asp62 | Asn31 |
| Lys63 | Ser30 |
|  | Asn31 |
| Thr64 | Arg27 |
|  | Ser30 |
|  | Asn31 |
| Tyr65 | Tyr13 |
|  | Asp15 |
|  | Leu18 |
|  | Ile22 |

TABLE 3-continued

Interaction list of the residues involved in CD269:APRIL und CD269:BAFF binding (residues NOT directly contacted by J22.9 are underlined). These interaction lists were generated using the software PDBsum (Laskowski R A (2009)).

|  | CD269 |
|---|---|
| Ala66 | Leu17 |
| Met67 | Leu17 |
| Gly68 | Leu17 |
| Arg90 | Leu17 |
|  | His19 |
| Cys91 | Leu17 |
| Ile92 | Leu17 |
|  | Leu18 |
| Glu97 | Ser29 |
|  | Ser30 |
|  | Asn31 |
| Leu99 | Ile22 |
|  | Leu26 |
| Asn101 | Leu18 |
| Pro123 | Ser16 |
|  | Leu17 |
| Arg124 | Tyr13 |
|  | Asp15 |
|  | Leu17 |
|  | Arg27 |
| Glu125 | Arg27 |
|  | Thr25 |
|  | Pro34 |
|  | Leu35 |
| Asn126 | Thr32 |
| Asp132 | His19 |

TABLE 4

Residues of the CD269 target bound by direct contacts of J22.9, APRIL and/or BAFF. Residues of the CD269 target directly contacted only by J22.9 are underlined (20, 23). Residues of the CD269 target NOT directly contacted by J22.9 are in bold type (30, 31, 33, 34, 35 for APRIL; 25, 29, 30, 31, 34, 35 for BAFF).

J22.9: 13, 15, 16, 17, 18, 19, 20, 22, 23, 26, 27, 32
APRIL: 13, 15, 17, 18, 19, 22, 26, 27, 30, 31, 32, 33, 34, 35
BAFF: 13, 15,16, 17,18, 19, 22, 25, 26, 27, 29, 30, 31, 32, 34, 35

TABLE 5

J22.9 Water interactions (J22.9-xi:H2O:CD269). The data in table 5 was generated using the software LigPlot (Wallace and Laskowski, European Bioinformatics Institute).

|  | H$_2$O# | CD269 |
|---|---|---|
| Light Chain |  |  |
| Ser31 (sc) | 285 | Thr32 (sc, mc) |
|  | 285, 286 | Arg27 (sc) |
|  | 285, 286 | Ser30 (sc) |
| Ser31 (mc) | 283, 284 | Arg27 (sc) |
| Asn32 (sc) | 105 | Asp15 (sc) |
|  | 105, 284 | Arg27 (sc) |
|  | 56 | Ser16 (sc) |
| Tyr36 | 66, 93, 450 | Leu17 (mc) |
| Ser50 (sc) | 105 | Asp15 (sc) |
| Ser52 (sc) | 286 | Ser30 (sc) |
|  | 286 | Arg27 (sc) |
|  | 286, 285 | Thr32 (sc, mc) |
| Gly66 (mc) | 287 | Thr32 (sc) |
|  | 285, 286 | Arg27 (sc) |
|  | 285, 286 | Ser30 (sc) |
| Gln89 (sc) | 66, 93, 450 | Leu17 (mc) |
| Tyr91 (mc) | 282 | Ser16 (sc) |
|  | 282, 281 | Ser16 (mc) |
| Tyr94 (sc) | 281 | Ser16 (mc) |
|  | 281, 282 | Ser16 (sc) |
| Heavy Chain |  |  |
| Trp33 (mc) | 42, 280 | Leu17 (mc) |
|  | 183, 279, 26 | Leu18 (mc) |
| Ser35 (sc) | 42, 66, 93, 280, 450 | Leu17 (mc) |
| Trp47 (sc) | 93, 450 | Leu17 (mc) |
| Glu50 (sc) | 281 | Ser16 (mc) |
|  | 281, 282 | Ser16 (sc) |
|  | 450 | Leu17 (mc) |
|  | 450, 280 | Leu17 (mc) |
| Leu99 (mc) | 280 | Leu17 (mc) |
| Tyr101 (mc) | 26 | Leu18 (mc) |

(sc = side chain H-bond; mc = main chain H-bond)

Strong Cytotoxic Efficacy of J22.9-xi is Strongly Decreased after Deglycosylation A luciferase-based cytotoxicity assay was established using the luciferase transduced MM.1S-Luc cell line. In this assay, bioluminescence is only detected from living cells since luciferase released by dead cells is unable to function due to the lack of ATP in the medium. PBMCs from healthy donors were isolated and mixed with MM.1S-Luc cells in a ratio of 20 to 1. After 4 hours the bioluminescence was measured.

With a selection of 4 unstimulated donor PBMC preparations, the in vitro cytotoxicity of J22.9-xi was determined. The cytotoxic potential varies slightly between PBMCs from different donors. Within 4 hours of incubation, cell lysis reached 18 to 35% at a concentration of 125 ng/ml J22.9-xi. Increasing the J22.9-xi concentration to 1 ug/ml increased cell lysis up to 56% (FIG. 3a).

After deglycosylation of J22.9-xi (J22.9-xi-N-glycan) with PNGase F, the cytotoxic activity dropped to below 8%, whereas the binding of J22.9-xi-N-glycan to BCMA-positive MM.1S cells remained unaltered (FIG. 3a,b).

J22.9-xi Reduces Tumor Burden in Xenografted Mice and Prolongs Survival

Figure 4:
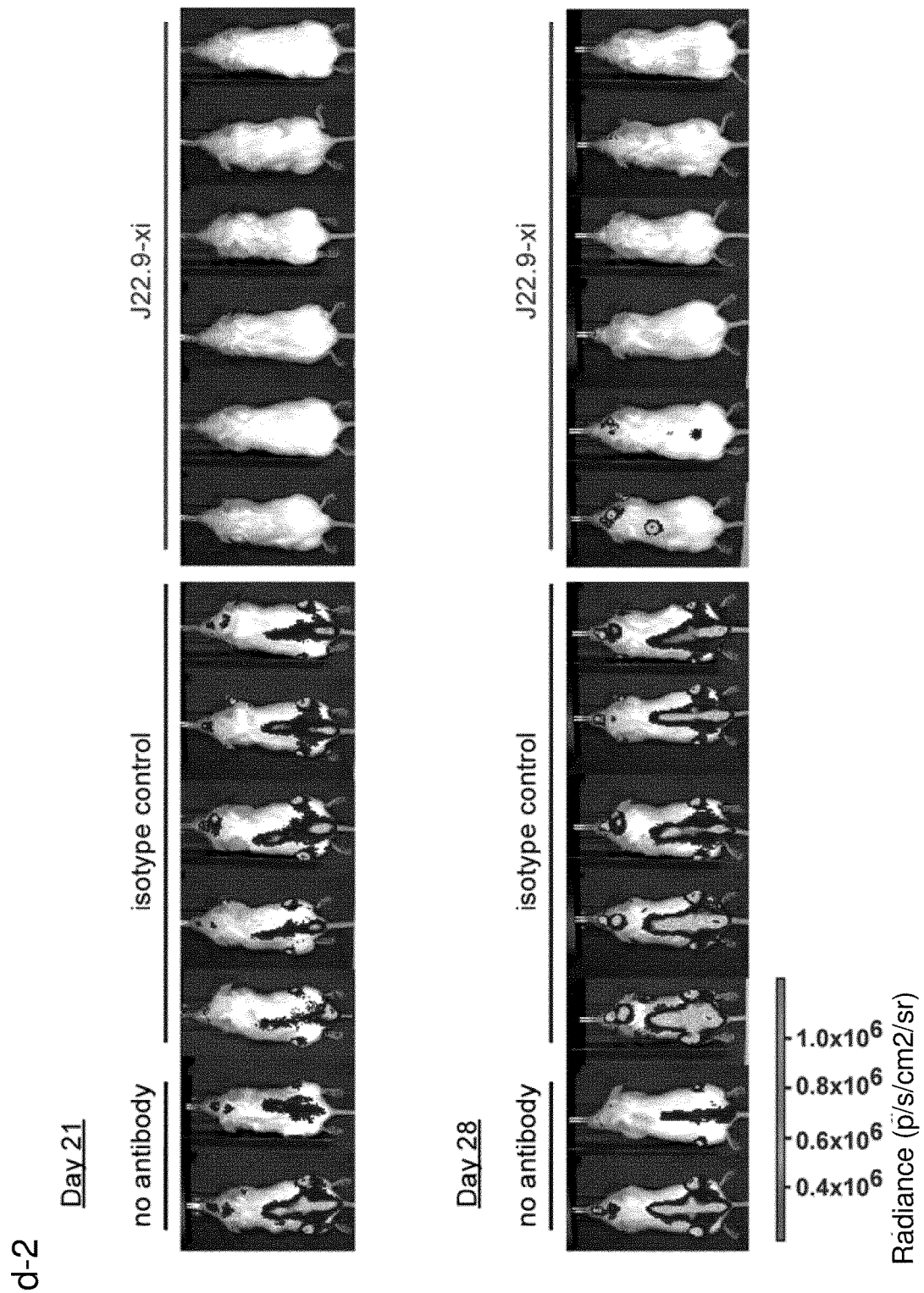
FIG. 4: Efficacy of J22.9-xi in xenografted NSG mice. (a) Tumor development over time with administration of 200 µg of J22.9-xi or the control antibody twice a week, and untreated control mice. (b) Total tumor burden between day 6 and 41 (Area under the curve (AUC) of (a)). Plotted are the mean values with SEM (P<0.01, *P<0.001, t-test). (c) Overall survival of J22.9-xi and isotype control mice. The P value was calculated using the Log-rank (Mantel-Cox) Test. (d-1) Detection of MM.1S-Luc cells in the indicated groups without administration of therapeutic antibody. Below the rightmost image the numbers (41, 41, 44, 40) indicate the days post-tumor cell injection on which the specific mouse died. (d-2) Detection of MM.1S-Luc cells in the indicated groups at day 21 and 28. Dorsal view. (e) Relationship between J22.9-xi concentration and tumor development. (f) Total tumor load between day 6 and 42 (AUC of (e)). Mean values with SEM (P<0.01, *P<0.001, t-test). (g) Overview of experimental time line.

We used NOD scid common gamma chain knock out (NSG) mice lacking functional B, T and NK cell populations. These mice, injected with $1*10^7$ MM.1S-Luc cells intravenously, develop hind limb paralysis within 6 weeks (FIG. 4d-1). The day on which the first symptom appears, defines the day of killing.

After injection of $1 \times 10^7$ MM.1S-Luc in the tail vein, the mice were divided randomly into 3 groups. The first group (n=2) received no treatment until the end of the experiment, whereas the second (n=5) and the third (n=6) group received twice weekly injections of 200 µg of an isotype control or the J22.9-xi antibody, respectively. The antibodies were administered for a period of 6 weeks intraperitoneally (i.p.) starting with the day of tumor cell injection. Tumor growth was monitored once a week using the IVIS Spectrum. Bioluminescence was measured 3 minutes after i.p. injection of luciferin.

Figure 2:
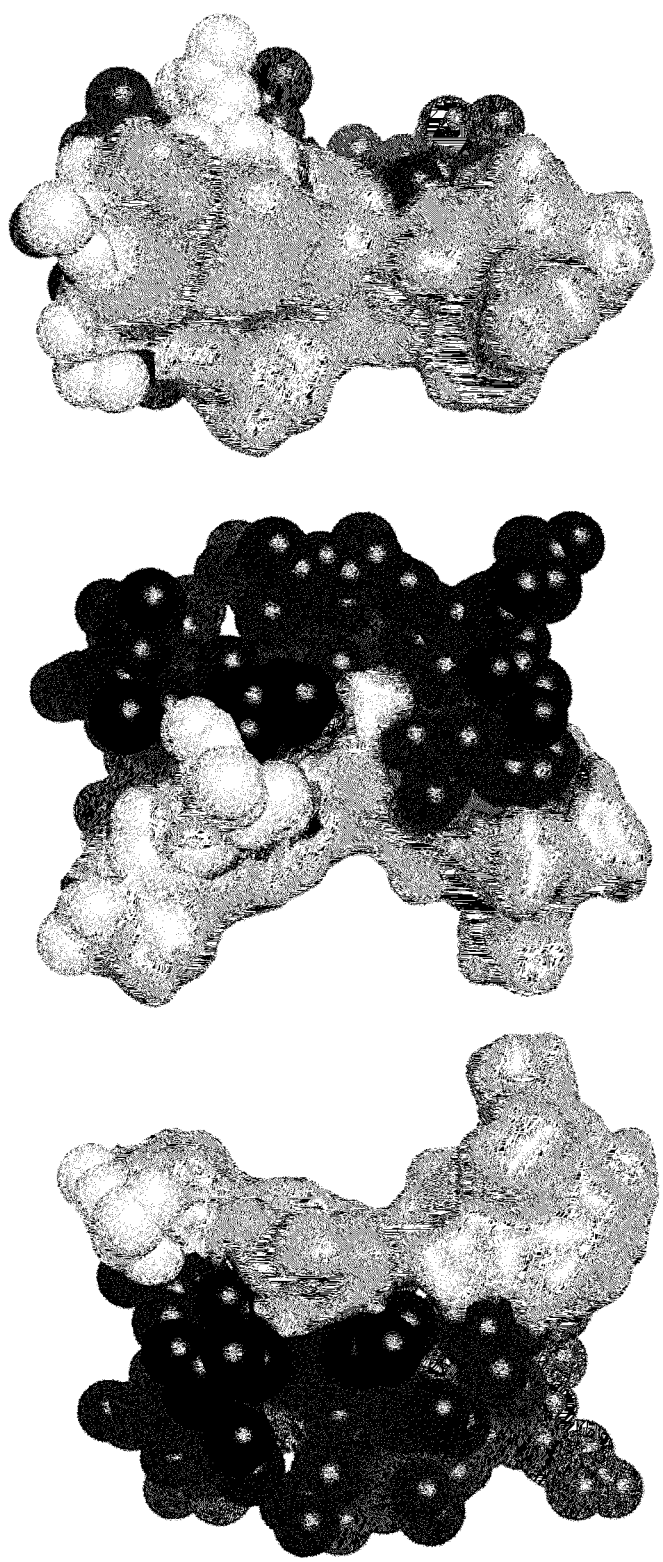
FIG. 2: The structure of CD269 (BCMA) and the J22.9-xi Fab:CD269 complex. (a) CD269 (BCMA) recognition surface. Three views of the extracellular domain of CD269 (BCMA) showing the binding epitope residues for BAFF/APRIL and J22.9-xi. At top, a view directly on the binding face of CD269 (BCMA): the light grey shading indicates all residues comprising the binding epitope of BAFF and APRIL as identified from their crystal structures, black residues (shown as spheres) do not contact either BAFF, APRIL or J22.9-xi; the subset of epitope residues involved in J22.9-xi binding are shown in surface representation; remaining light grey residues shown as spheres are part of both the BAFF and APRIL epitopes but make no direct contacts to J22.9-xi. The middle and lower panels show the same representation as in the top panel but rotated 90° toward and away from the viewer, respectively. (b) Two views of the J22.9-xi Fab:CD269 complex. J22.9-xi is shown in surface representation with the heavy chain coloured light grey and the light chain in dark grey. CD269 (BCMA) is shown in ribbon representation bound to the J22.9-xi antigen pocket. At left, full view of the Fab:CD269 complex; at right, the complex tilted toward the viewer to show the binding pocket.
Figure 2:
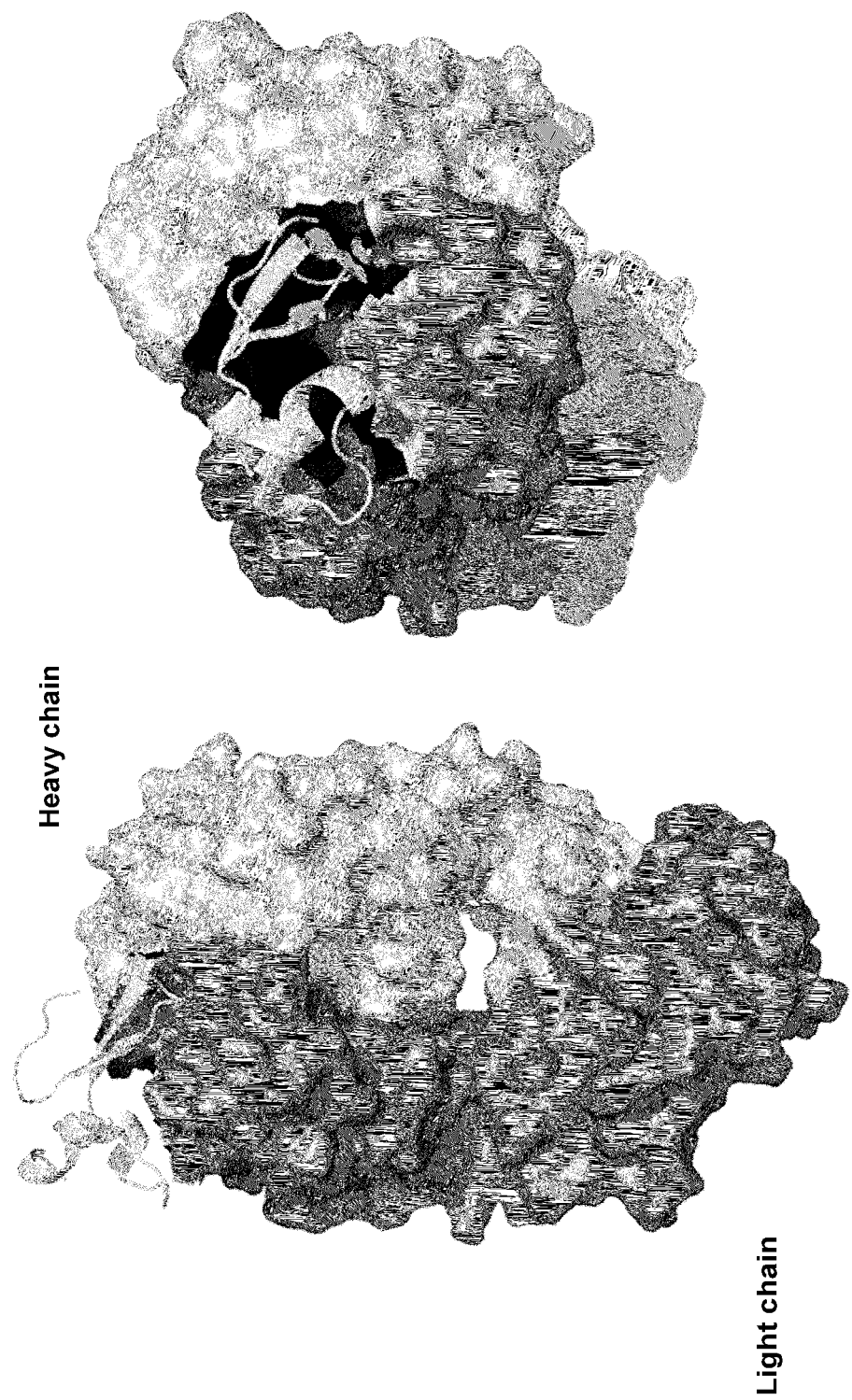

A similar course of tumor development was seen in both the untreated group and the group receiving the control antibody, whereas the group treated with J22.9-xi showed significantly less tumor burden, already beginning at the first measurement point at day six (FIG. 4a). In addition, this group showed a smaller overall tumor load during the whole monitoring period (FIG. 4b). Isotype control treated animals had a median survival of 46 days after cell injection. Mice receiving J22.9-xi lived an average of 26 days longer. This corresponds to an extended survival of 55% compared with mice receiving the control antibody (FIG. 4c). Massive infiltrations of tumor cells into the spine and inguinal lymph nodes were seen in non-treated mice and in mice receiving the isotype control antibody by day 28 after cell injection (FIG. 4d-2).

Administration of 200 µg of an antibody to a mouse corresponds to approximately 10 mg/kg bodyweight. To test the efficacy of J22.9-xi at lower doses we divided MM.1S-Luc-xenografted mice into four groups. The first group (n=7) received 200 µg of the control antibody twice weekly, and groups 2, 3 (each n=3) and 4 (n=9) were injected with 2 µg, 20 µg or 200 µg twice a week, respectively. Injection and monitoring were performed as described above.

Although tumors developed as expected in the control group mice, dramatically restricted tumor growth was observed in the groups receiving 20 µg or 200 µg of J22.9-xi (FIG. 4e,f). An overview of the experimental timeline is provided in FIG. 4g.

Growth of Established Tumors Arrests for 5 Weeks During J22.9-xi Treatment

Therapeutic administration was mimicked by delaying the start of antibody treatment to 5 days after tumor cell injection. The xenografted mice were divided into 2 groups (n=6). The animals received 200 µg per injection of either the isotype control or J22.9-xi antibody twice a week. The first measurement was done at day 8 post cell injection. While there is no tumor-derived bioluminescence measurable to day 35 in the group receiving J22.9-xi (n=5), a steady increase in tumor load was seen in animals receiving the isotype control antibody (n=6) (FIG. 5a,b). Mice from the isotype control group survived an average of 56 days after the cell injection, whereas all mice receiving J22.9-xi are still alive at day 77 (FIG. 5c). An overview of the experimental timeline is provided in FIG. 5d.

Intensive Early Phase Treatment with J22.9-xi Prevents Tumor Growth for 7 Weeks

Figure 6:
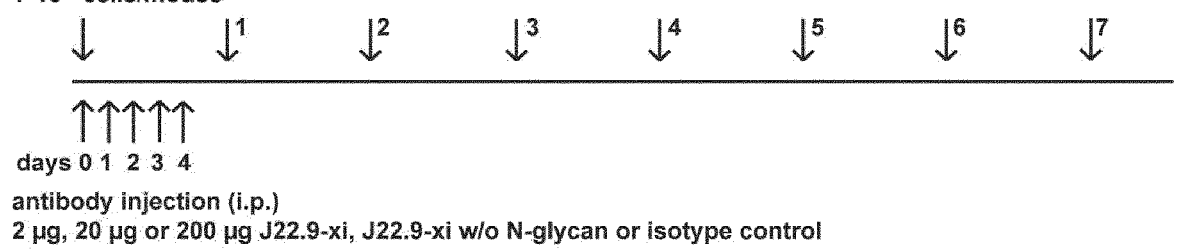
FIG. 6: Tumor treatment in the early phase of disease. (a) Course of tumor growth when treated with 2 μg, 20 μg or 200 μg of J22.9-xi or 200 μg of either the isotype control antibody or J22.9-xi without —N-glycans, and without tumor. (b) Total tumor burden within day 9 to 44 (AUC of (a)). Shown are the mean values with SEM (*P<0.05, **P<0.01, t-test). (c) Survival of antibody-treated and control xenograft SCID-Beige mice. The P values were calculated using Log-rank (Mantel-Cox) Test. (d) An overview of the experimental time line is provided.
Figure 7:
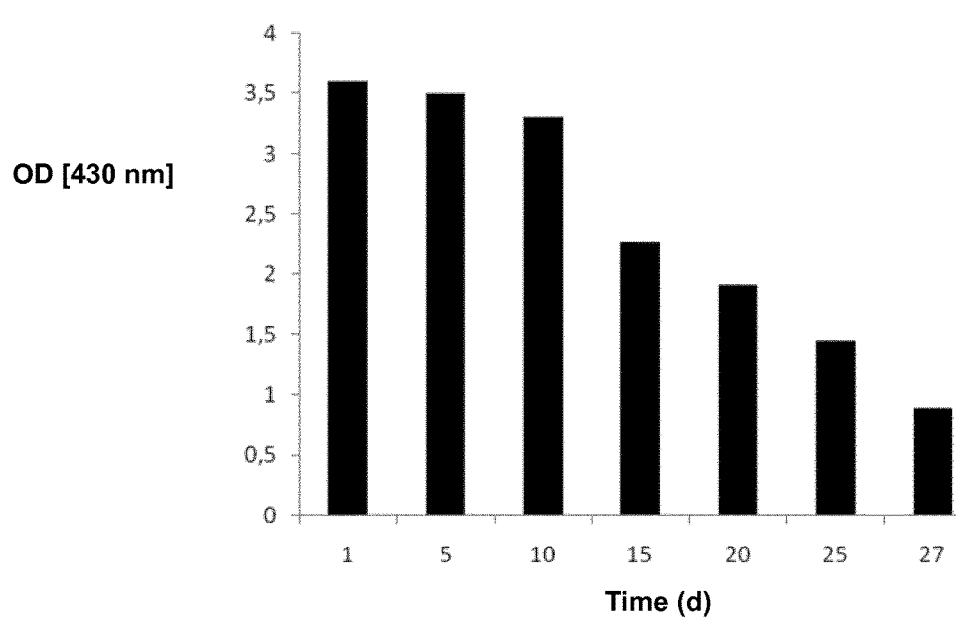
FIG. 7: Instability of hybridoma J22.9. The supernatant of hybridoma J22.9 tested positive for binding to BCMA in ELISA on BCMA-coated microtiter plates at day 1. Later analysis at indicated time points revealed a reduction of binding capacity of the supernatant. The medium was exchanged on days 7, 14 and 21.

In order to further assess the effect of treatment timing on tumor growth, different antibodies were administered for five consecutive days starting from the day of tumor cell injection. Subsequent to i.v. cell injection, the animals were divided randomly into 5 groups. Group 1 (n=5) was treated with 200 µg of the isotype control antibody per injection (i.p.), whereas group 2 (n=6) received 200 µg/injection of the J22.9-xi-N-glycan antibody. The mice from groups 3 (n=4), group 4 (n=5) and group 5 (n=5) obtained 200 µg, 20 µg and 2 µg per injection of the J22.9-xi antibody, respectively. Bioluminescence measurements began at day 9 post cell injection. Up to day 44, no tumor-derived bioluminescence was seen in any of the groups receiving the intact J22.9-xi antibody. Although the tumor growth in the animals treated with J22.9-xi-N-glycan is decelerated, the overall tumor load is not significantly different from those animals receiving the isotype control antibody (FIG. 6a,b). Although the overall tumor load of animals treated with J22.9-xi-N-glycan (deglycosylated) was not significantly different (FIG. 6b), the lifespan of these mice was substantially increased compared to the isoAb-treated group (FIG. 6c). Since J22.9-xi-N-glycan was shown to be unable to induce ADCC or CDC, this result indicates that alone the binding of J22.9-xi to BCMA hinders tumor growth. It may be reasonably considered that this is due to blocking of the interaction between the receptor and its native ligands (APRIL and BAFF). An overview of the experimental timeline is provided in FIG. 6d.

Humanisation of J22.9-xi

The J22.9-xi antibody was humanized based on sequence alignment and the data obtained from the crystal structure. The sequences of the variable regions were aligned to their respective human homologs using IgBLAST (NCBI) or Clustal (EBI). Each proposed mutation was evaluated by visual inspection of the structure before alteration.

Binding of Humanized Variants to BCMA Target

Binding of the mutants to BCMA was tested using flow cytometry, ELISA and SPR. The affinity of the humanized antibodies was measured using surface plasmon resonance (ProteOn™ XPR36; Bio-Rad). The binding data show surprising results with respect to the specificity and affinity of the humanized antibody variants to the same epitope as tested for J22.9-xi binding. As shown in the table below, it was entirely surprising that the humanized antibodies as described herein exhibited comparable binding characteristics as the original chimeric antibody. The SPR data reveals that the affinities of the humanized variants are similar to those of the chimera and are sufficient to assume their clinical relevance in light of the data provided herein for the original chimeric antibody. A skilled person would not have expected that through the modification of the CDRs during humanization of the chimera that the binding characteristics would be maintained to such an extent.

ELISA was carried out as described herein using BCMA-coated microtiter plates (1 microg/ml). As observed in FIG. 10, binding was comparable for all humanized variants in comparison to J22.9-xi using both human and cynomlgous BCMA.

Figure 11:
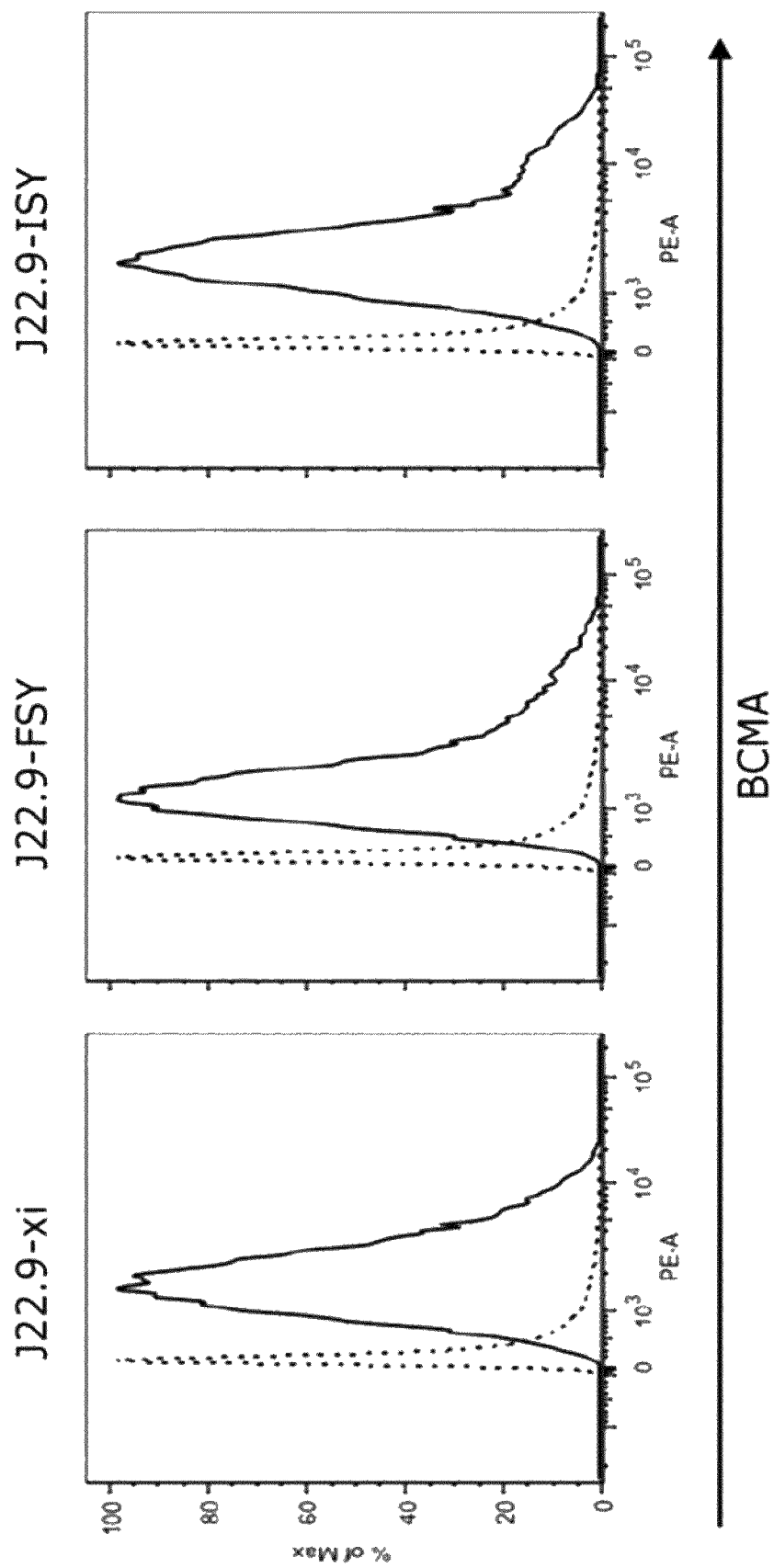
FIG. 11: Sequence optimized variants of J22.9-xi show similar binding in flow cytometry. Binding of the chimeric J22.9-xi and humanized variants was tested via flow cytometry using the human MM cell line RPMI-8226 (J22.9-FSY corresponds to humanized and PTM modified SEQ ID No. 28; J22.9-ISY corresponds to humanized and PTM modified SEQ ID No. 29).
Figure 12:
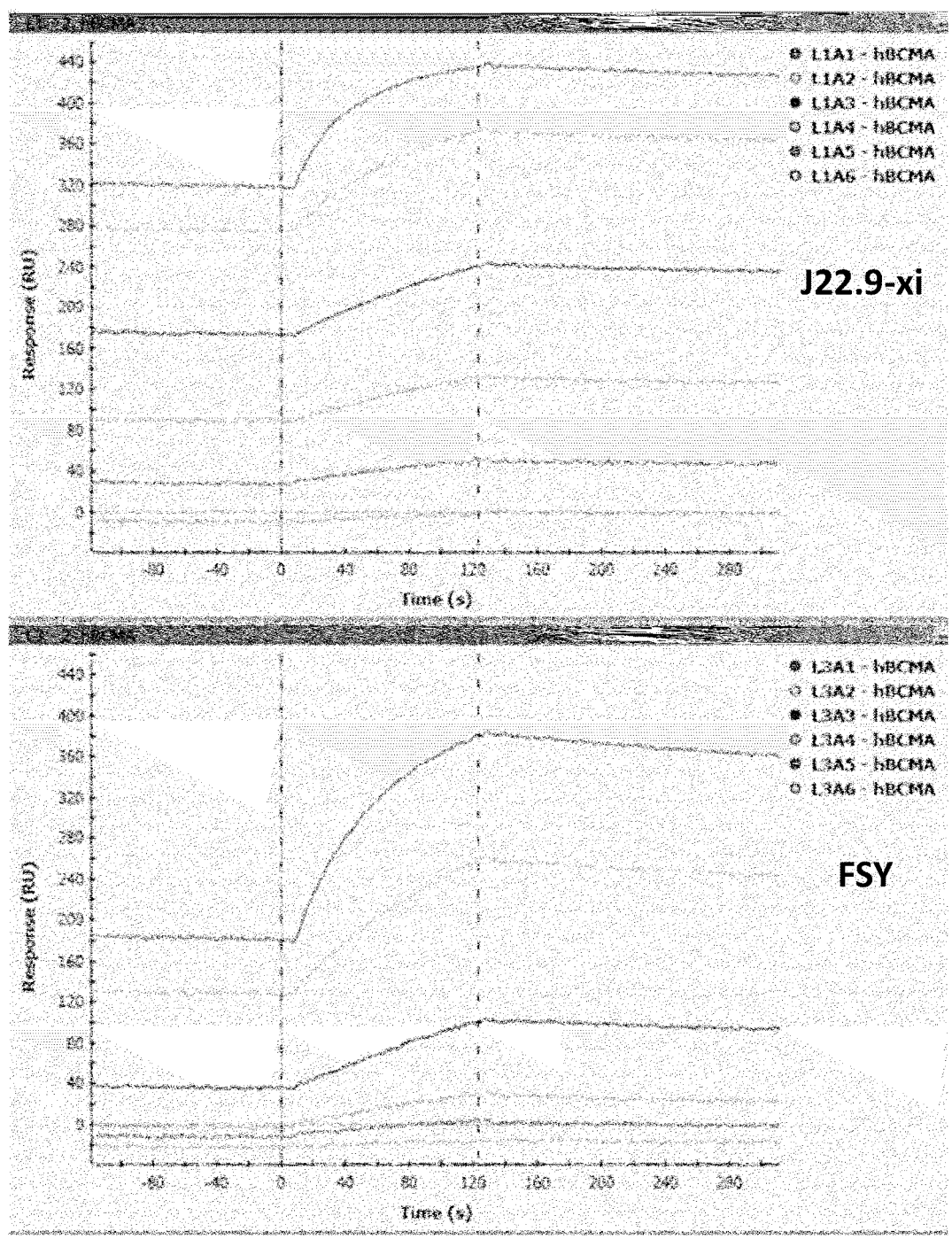
FIG. 12: SPR raw data: Binding affinities of the chimeric J22.9-xi and humanized variants to human (A) and cynomolgus (B) BCMA was measured by Surface Plasmon Resonance (SPR) Spectrometry. IgGs were immobilized via amine chemistry to a Proteon GLH sensor chip and binding measured with BCMA in the mobile phase. The order of raw data traces in the graph corresponds to the order to samples listed in the legend of the figure.
Figure 12:
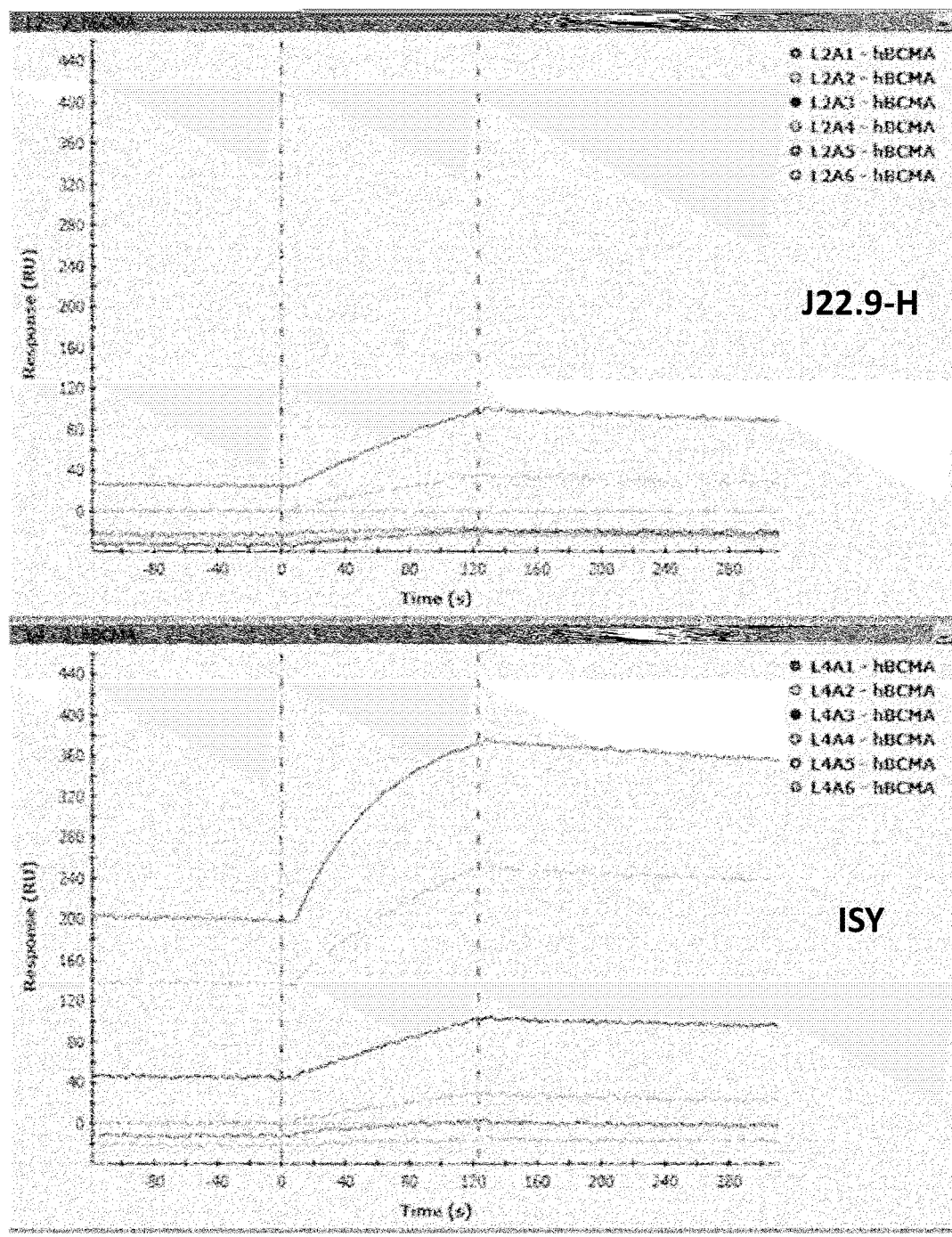
Figure 12:
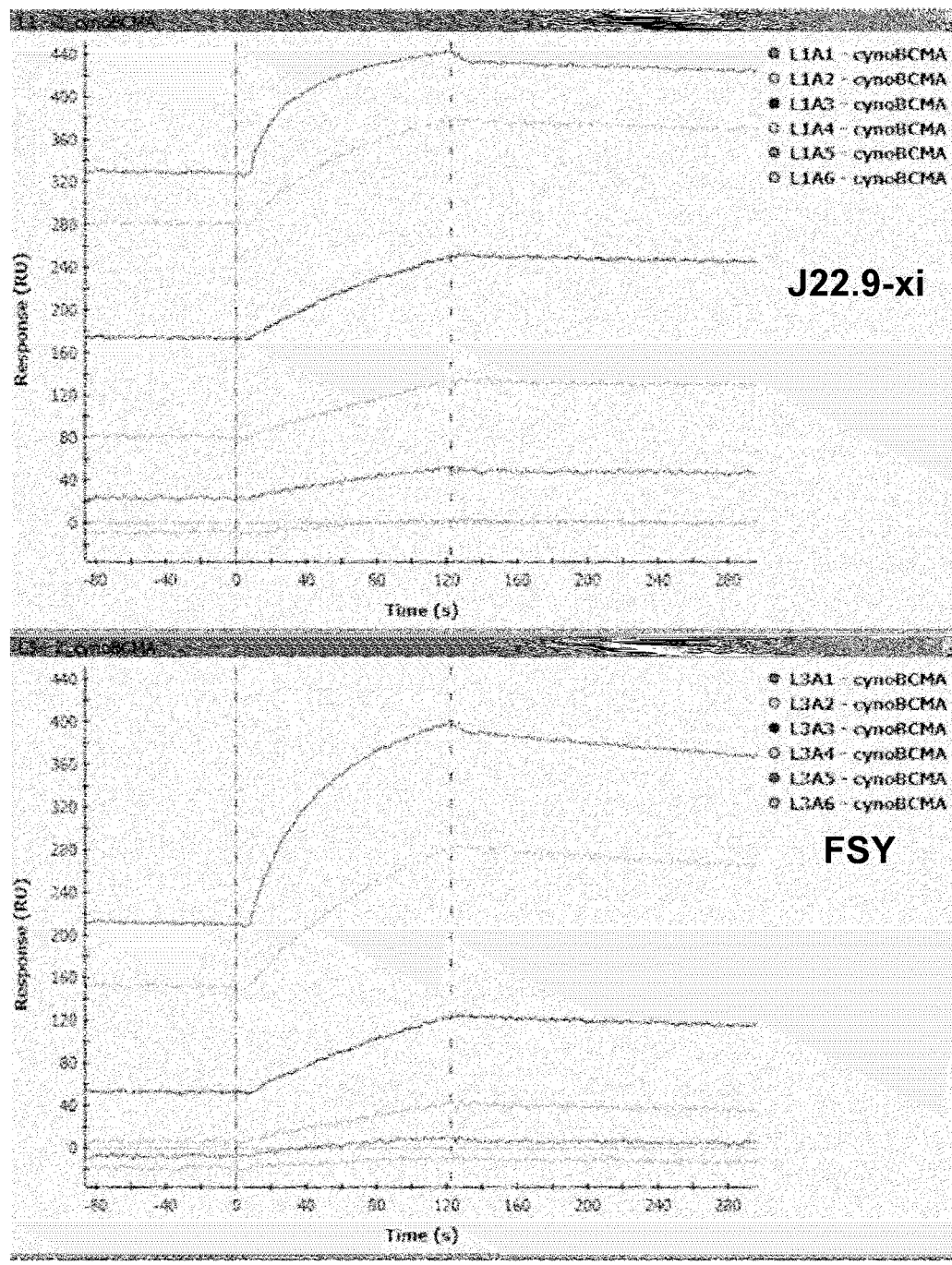
Figure 12:
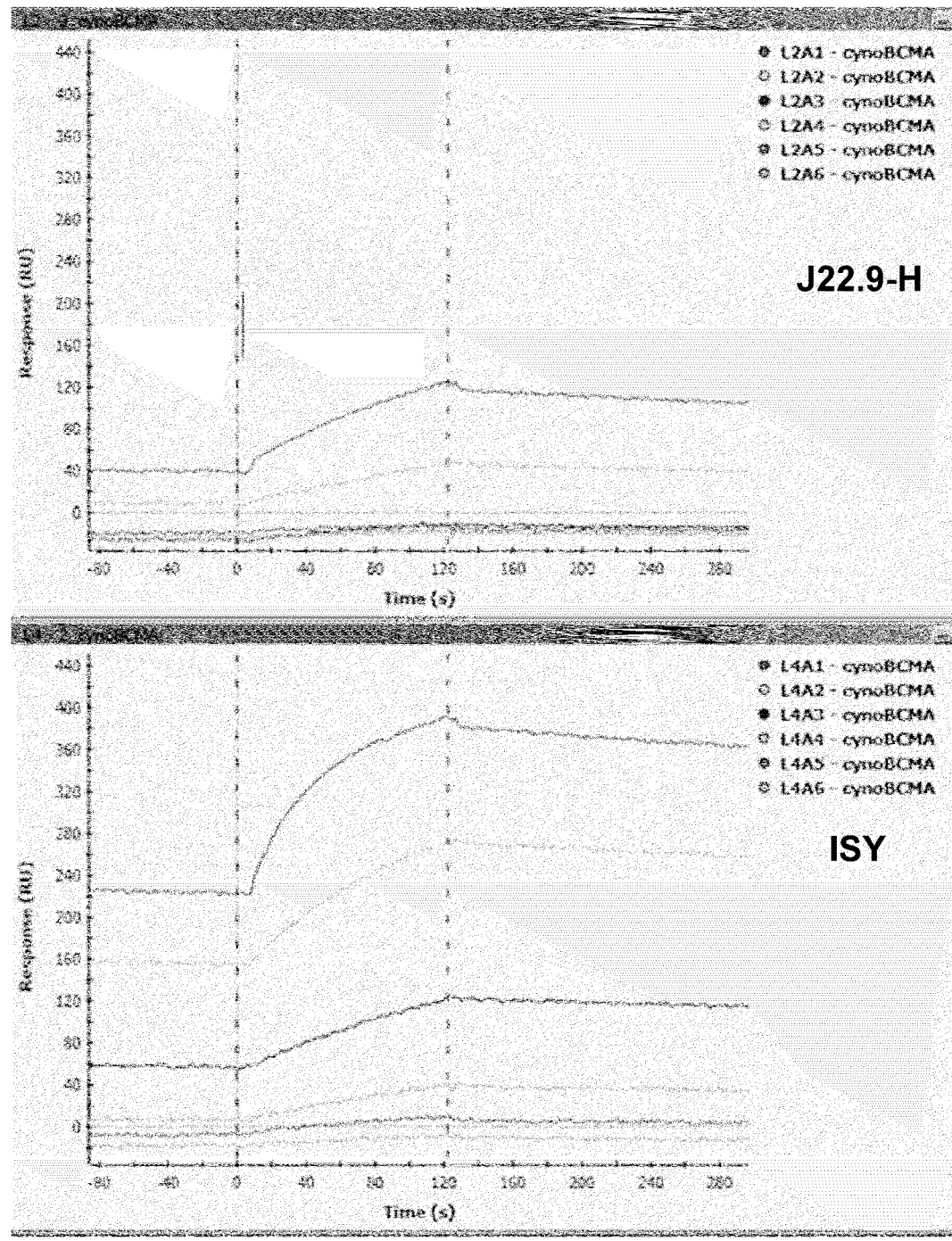

Flow cytometry was also carried out using the humanized variants described herein and equivalent binding to both human and cynomlgous BCMA for all humanized variants tested was shown (refer FIG. 11).

SPR analysis was also conducted and affinities measured for humanized antibody variants. As can be observed in the table below (table 6), the affinities of the humanized variants (J22.9-H corresponds to humanized sequence SEQ ID No. 27; J22.9-FSY corresponds to humanized and PTM modified SEQ ID No. 28; J22.9-ISY corresponds to humanized and PTM modified SEQ ID No. 29).

TABLE 6

| | | | | | SPR Data | |
|---|---|---|---|---|---|---|
| Name | ELISA (human) | ELISA (cynomolgous) | Flow cytometry | Melting temperatures | Affinity (SPR) (human) (n = 3) | Affinity (SPR) (cynomolgous) (n = 2) |
| J22.9-xi | +++ | +++ | +++ | 86/94° C. | $2.8 \pm 0.7 \times 10^{-10}$M | $2.7 \times 10^{-9}$M |

TABLE 6-continued

SPR Data

| Name | ELISA (human) | ELISA (cynomolgous) | Flow cytometry | Melting temperatures | Affinity (SPR) (human) (n = 3) | Affinity (SPR) (cynomolgous) (n = 2) |
|---|---|---|---|---|---|---|
| J22.9-H | ++ | + | nd | 86/94° C. | $1.5 \pm 0.3 \times 10^{-8}$M | $2.0 \times 10^{-7}$M |
| J22.9-FSY | +++ | +++ | +++ | 87/94° C. | $2.2 \pm 0.3 \times 10^{-9}$M | $2.0 \times 10^{-8}$M |
| J22.9-ISY | +++ | +++ | +++ | 86/94° C. | $2.0 \pm 0.2 \times 10^{-9}$M | $1.7 \times 10^{-8}$M |

Figure 13:
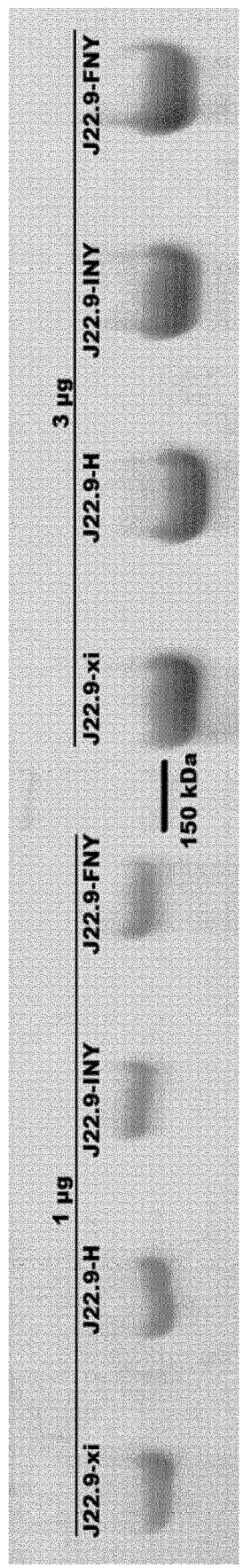
FIG. 13: Gel electrophoresis of antibody variants. Antibody variants were run in non-reduced SDS-PAGE and stained to show protein migration.

Amino Acid 54 in CDR2 of the J22.9 Heavy Chain:

In order to remove a potential post-translational modification site in the humanized J22.9, residue D54 of the heavy chain CDR2 was mutated to asparagine (N), inadvertently creating a new potential modification site for N-linked glycosylation. The mutated heavy chain containing N54 migrated slower on SDS gels (FIG. 13), indicating a larger size and that the CDR was glycosylated.

The corresponding IgG, J22.9-FNY, nevertheless bound BCMA in FACS and ELISA, and was crystallized in complex with BCMA. Although not completely refined, the 2.7 Angstrom resolution structure shows clear electron density extending from the N54 side chain—consistent with a sugar modification of the residue. It is surprising that such a large extension of the side chain would not disrupt binding to BCMA and it could be expected from these observations that multiple and various amino acid substitutions would be tolerated at this position, potentially also derivatizations other than sugars.

Methods

Cell Lines and Culture

The human multiple myeloma cell line MM.1S (Greenstein et al. (2003) Exp Hematol 31:271-282) was obtained from Prof. B. Dörken (MDC, Berlin, Germany). For in vivo monitoring of tumor cell growth, Luciferase and GFP were cloned into the pFU vector of the lentiviral vector system ViraPower (Invitrogen). Via GFP-expression of transduced cells, monoclonal cell lines were isolated using fluorescence-activated single cell sorting. Cell lines were cultured in RPMI-1640 medium without phenol red, containing 10% fetal calf serum, 100 units/ml of penicillin, and 100 µg/ml of streptomycin (all from PAA).

The HEK293-6E cells, purchased from the National Research Council of Canada, were maintained in Freestyle F17 medium (Invitrogen) supplemented with 7.5 mM L-Glutamine (PAA), 0.1% Pluronic F-68 (Invitrogen), and 25 µg/ml G418 (Invitrogen). Cells were grown in Erlenmeyer flasks (Corning) at 110 rpm and 37° C. in a 5% CO2 atmosphere.

Antibody Production and Purification

To obtain a BCMA-binding antibody, standard hybridoma technique was used. 4 BL/6 wild type mice were immunized 6 times with incomplete Freund's adjuvant and 30 µg of the extracellular domain of human BCMA C-terminally fused to Glutathione S-transferase (GST). After cell fusion followed by a screening period the J22.9 hybridoma was shown to secrete an anti-BCMA antibody.

Due to the instability of the hybridomas the variable regions of the light and heavy chain of hybridoma J22.9 were amplified and cloned upstream of the human kappa or the IgG1 constant domain genes, respectively. The chimeric J22.9-xi antibody was produced by transient cotransfection of 293-6E cells with a 1:2 DNA plasmid mixture encoding the light and heavy chains, respectively. In brief: 293-6E cells were resuspended to $1.7 \times 10^6$ cells/ml in serum free Freestyle F17 medium and transfected using polyethyleneimine at a final concentration of 1 µg/ml culture. Two days after transfection, cells were fed with 100% of the transfection volume Freestyle F17 medium containing 1% tryptone N1 (Organo Technie). At day 7 cells were harvested by centrifugation and the filtered (0.45 µm) culture medium was passed over a 3.5 ml Protein A Sepharose column (Bio-Rad). The column was washed with 10 ml phosphate buffered saline (PBS) and antibody eluted by addition of 20 mM sodium acetate, 150 mM NaCl, pH 3.5. Fractions of 2 ml were collected directly into tubes containing 100 µl 1 M HEPES, pH 7.5 for neutralization. The final yield of full length IgG was approximately 40 mg/l culture.

Since hybridoma J22.9 lost the capacity to produce/secrete the anti-BCMA antibody (FIG. 8), the variable regions of the heavy and light chains were amplified using PCR and subsequently cloned at the 5' end of the human constant IgG1 and K light chain genes, respectively. Through co-transfection of 293-6E cells with these two plasmids, the chimeric J22.9-xi antibody was produced. The production of the antibody of the invention was therefore inherently difficult and not achievable by straightforward routine methods.

The isotype control antibody composed of the J22.9-xi heavy chain and a random chimeric kappa light chain was produced in parallel with the J22.9-xi antibody. This antibody was shown by ELISA and flow cytometry to be unable to bind to BCMA.

The N-linked oligosaccharide chains at Asn297 of the heavy chain of J22.9-xi were removed enzymatically using N-Glycosidase F (PNGase F) (NEB). 10 mg of J22.9-xi were incubated with 15,000 units PNGase F in 500 µl PBS (pH 7.4) for 36 hours at 37° C. followed by buffer exchange into sterile PBS.

Determination of Binding and Blocking Capacities of J22.9-xi by Enzyme-Linked Immunosorbent Assays (ELISA)

Microtiter plates were coated with 10 µg/ml of the extracellular domain of human BCMA. Coated BCMA was detected with serial dilution of J22.9-xi and the isotype control ranging from 1 to 1000 ng. Binding of J22.9-xi or isotype control antibody to the coated BCMA was detected with horseradish peroxidase (HRP)-conjugated goat anti-human secondary antibody (Jackson ImmunoResearch, 109-035-098, dilution 1:5,000).

Microtiter plates were coated with 1 µg/ml of the extracellular domain of human or cynomolgous BCMA (hBCMA or cyBCMA, respectively). Coated BCMA was detected with serial dilution of J22.9-xi, J22.9-H, J22.9-ISY and J22.9-FSY ranging from 0.26 pM to 500 nM. Binding of antibodies to the coated BCMA was detected with horseradish peroxidase (HRP)-conjugated goat anti-human secondary antibody (Jackson ImmunoResearch, 109-035-098, dilution 1:5,000).

For the blocking experiment, 1 mg/ml of human recombinant BAFF fused to a His-tag (Biomol) was applied after the antibodies and washing and detected using the mouse anti-His tag (AbD Serotec, AD1.1.10, dilution 1:5,000, HRP-conjugated) antibody. All ELISAs were developed using BD OptEIA reagents A and B (BD Bioscience) and measured with a microplate spectrophotometer (BioTek) at 450 nm and 570 nm.

Flow Cytometry Analysis

For cell surface antigen detection experiments, self-made antibodies (J22.9-xi, J22.9-H, J22.9-ISY, J22.9-FSY and the isotype control) and commercially available mouse anti-His tag (AbD Serotec, AD1.1.10, dilution 1:100, Alexa Fluor 488-conjugated) and goat anti-human IgG1 (Jackson ImmunoResearch, 109-116-098, dilution 1:400, PE-conjugated) antibodies and human recombinant BAFF fused to a His-tag (Biomol) were used. Experiments were performed on a FACSCalibur or a FACSCanto II flow cytometer (BD Bioscience). The data were analysed with Flowjo software version 7.6 (TreeStar Inc.).

Generation of Fab and Fab:BCMA Complexes (Fab)$_2$ fragments were generated from full length J22.9-xi IgG by incubation with pepsin. J22.9-xi was passed over a PD-10 buffer exchange column into 50 mM sodium acetate, pH 3.5 and pepsin added at 30 µg per milligram J22.9-xi. Incubation at 37° C. for 2.5 hours was sufficient to completely digest the fragment crystallizable (Fc) region and pepsin was inactivated by exchange over a PD-10 column into PBS (pH 7.2). The reduction of the (Fab)$_2$ fragments to individual Fabs was accomplished in PBS by addition of 2-Mercaptoethylamine (50 mM) in the presence of 5 mM ethylenediaminetetraacetic acid (EDTA). After incubation for 90 minutes at 37° C., the reduced cysteines were blocked by alkylation with 500 µM iodoacetamide for 30 minutes followed by buffer exchange into fresh PBS. The Fab fragments were combined with 1.5 molar equivalents of purified BCMA and the complexes isolated by size exclusion chromatography on a Superdex 75 16/60 column. Fractions were analyzed on 4-12% SDS polyacrylamide gels and fractions containing both Fab and BCMA were pooled and concentrated for crystallization trials.

Crystallization of Fab:BCMA Complexes

Concentrated complexes were supplemented with 0.5 molar equivalents of pure BCMA to ensure saturation and were subjected to crystallization screening. Initial Fab:BCMA crystallization conditions were identified from commercial screens (Qiagen) in 96-well sitting drop format plates using a Gryphon pipetting robot (200 nl drops) and optimized in 24 well plates in hanging drops (2-3 ul). The complex was concentrated to 8 mg/ml and crystallized in 21% PEG 3350, 0.1 M BisTris pH 6.5 and 5 mM CuCl$_2$ at 20° C. Crystals appeared after three days as clusters of thin plates and attained their final size (0.2-0.3 mm) within approximately 7 days. Clusters were separated and individual plates were flash frozen in liquid nitrogen in mother liquor with 20% glycerol as cryoprotectant. Complete diffraction data was collected from a single crystal at the BESSY synchrotron of the Helmoltz Zentrum Berlin. The structure was solved to a resolution of 1.9 angstroms by molecular replacement using the experimental phases from the structure of Efalizumab (3E09) as the search model. Data processing was performed with the ccp4 suite of programs, structure refinement was performed using Phenix (Adams P D, et al. (2010), Acta Cryst. D66: 213-221) and model building and assessment using Coot. (Emsley et al, Acta Crystallographica Section D—Biological Crystallography, 2010, 66:486-501) Images were made using PyMOL (The PyMOL Molecular Graphics System, Version 1.5.0.4 Schrödinger, LLC).

In Vitro Cytotoxicity Assay

In this assay the cytotoxic effect of J22.9-xi was determined by measuring the luminescence of the remaining living cells in a bioluminescence reader. In short: freshly obtained human filter buffy coats (FBC) were back-flushed by gravity with 160 ml elution buffer (PBS (pH 7.4) containing 5 mM Na$_2$-EDTA and 2.5 [w/v] sucrose). Mononuclear cells were isolated from the eluted cells by Ficoll gradient centrifugation. Mononuclear cells from the interphases were taken and washed twice in elution buffer. After erythrocyte lysis, PBMCs were washed again, counted and adjusted by dilution in RPMI/10% FCS w/o phenol red to 1*10$^7$ cells/ml. 5*10$^4$ MM.1S-Luc cells in 50 µl RPMI were plated in microtiter plates. Ten minutes prior to the addition of 100 µl PBMCs, the MM.1S-Luc cells were incubated with J22.9-xi or the isotype control antibody serial dilutions in a sample volume of 200 µl. After addition of target cells, antibodies and effector cells, microtiter plates were centrifuged (300×g) for 2 minutes at room temperature (RT) and stored at 37° C. with 5% CO2. Control wells were treated with 1 Triton X instead of antibody for complete lysis. After 4 hours of incubation, 25 µl of PBS with luciferin (250 ng/ml) were applied to each well, and the bioluminescence of the living cells was measured in a bioluminescence reader (Tecan). The specific cytotoxicity was calculated according to the following formula:

$$100-[value(J22.9\text{-}xi)-value(total\ lysis)]/[value(isotype\ control)-value(total\ lysis)]*100.$$

In Vivo Studies

NOD.Cg-Prkdcscid Il2rgtm1Wjl Tg(CSF2)2Ygy Tg(IL3) 1Ygy Tg(KITLG)3YgyJGckRolyJ mice (NSG) from The Jackson Laboratory and CB17.Cg-Prkdcscid Lystbg/Crl mice from Charles River Deutschland (Sulzfeld, Germany) were used. Experiments were performed with mice between 8-14 weeks old. All animal studies were performed according to institutional and state guidelines, under specific pathogen-free conditions. In the experimental examples relating to treatment of established tumours and tumour treatment in the early phase of disease the CB17.Cg-Prkdcscid Lystbg/Crl mice were used. The phenotype of the two mice strains mentioned herein is very similar. The animals have no functional B-, T- and NK-cells. A slightly slower tumour growth was observed in the CB17.Cg mice, indicating an even more promising effect of the therapeutic antibody of the present invention.

The xenograft model of multiple myeloma was induced by intravenous injection of 1*10$^7$ MM.1S-Luc cells in the tail vein at day zero. In this model, untreated animals develop hind limb paralysis within 6 weeks. Occurrence of this symptom indicates the end point of the experiment.

For the efficacy studies, the antibodies were administered intraperitoneally (i.p.) twice a week or on 5 consecutive days starting at day zero. The J22.9-xi antibody was given in doses of 2 µg, 20 µg or 200 µg per injection; for the isotype control antibody, 200 µg/injection was used. The bioluminescence of the MM.1S-Luc cells was measured after i.p. injection of 150 µg luciferin using the IVIS Spectrum (Caliper Life Sciences). Measurements were done weekly. At each timepoint, 3 untreated control mice were also administered luciferin. Total flux values of these animals are either subtracted from each measurement or shown in the graphs.

To treat established tumors, antibody therapy was begun 5 days after injection of the MM.1S-Luc cells. 200 μg of the J22.9-xi or isotype control antibody was administered twice a week for a period of 6 weeks.

Humanization of J22.9-xi

The heavy and light chain variable region sequences (mouse) were aligned with those from the corresponding heavy and light chain subtype human sequences to determine which residue alterations were required to produce a fully humanized sequence variant. Using the crystal structure of the J22.9-xi:hBCMA complex, each modification was first assessed in silico to identify mutations that could potentially disrupt binding of the antibody to BCMA. Two complete J22.9 variable region genes for each chain were synthesized, one with the original mouse sequence and one with a completely humanized sequence (i.e. containing all of the necessary humanizing mutations) with two added restriction enzyme sites to divide the genes into three cassettes each. After flagging potentially problematic mutations, various combinations of the original mouse and fully humanized gene cassettes were produced and their corresponding IgGs were expressed, purified and subjected to FACS analysis with BCMA positive cells to assess binding. Flagged problematic residues were mutated individually using PCR to verify their effect on affinity to BCMA and the final optimized constructs were subsequently quantitatively assessed for binding to both human and cynomolgus BCMA via SPR.

SPR

SPR was performed on a ProteonXPR36 using phosphate buffered saline supplemented with 0.005% Tween-20 (PBST). Whole IgG at a concentration of 15 ug/ml was immobilized to a Proteon GLH sensor chip using standard amine chemistry according to the manufacturer's instructions. For binding experiments, human or cynomolgus BCMA in PBST was used as the mobile phase. Binding affinities ($K_d$) were calculated from association ($k_{on}$) and dissociation ($k_o11$) constants determined in parallel at multiple concentrations of BCMA (ranging from 0.4 to 800 nM for hBCMA and 2.7 nM to 1 μM for cynoBCMA) assuming a single-site binding model.

Additionally, further experimentation shows that the preferred embodiments of the invention provide surprising and unexpected effects, thereby solving the problem of the invention in a non-obvious fashion.

REFERENCES

Adams, P. D., Afonine, P. V., Bunkoczi, G., Chen, V. B., Davis, I. W., Echols, N., Headd, J. J., Hung, L. W., Kapral, G. J., Grosse-Kunstleve, R. W., et al. (2010). PHENIX: a comprehensive Python-based system for macromolecular structure solution. Acta Crystallogr D Biol Crystallogr 66, 213-221.

Al-Lazikani, B., Lesk, A. M., and Chothia, C. (1997). Standard conformations for the canonical structures of immunoglobulins. J Mol Biol 273, 927-948.

Anthony, R. M., and Ravetch, J. V. (2010). A novel role for the IgG Fc glycan: the anti-inflammatory activity of sialylated IgG Fcs. J Clin Immunol 30 Suppl 1, S9-14.

Chan et al. (2010) Nat Rev Immunol 10:301-316

Chavez-Galan, L., Arenas-Del Angel, M. C., Zenteno, E., Chavez, R., and Lascurain, R. (2009). Cell death mechanisms induced by cytotoxic lymphocytes. Cell Mol Immunol 6, 15-25.

Chiu, A., Xu, W., He, B., Dillon, S. R., Gross, J. A., Sievers, E., Qiao, X., Santini, P., Hyjek, E., Lee, J. W., et al. (2007). Hodgkin lymphoma cells express TACI and BCMA receptors and generate survival and proliferation signals in response to BAFF and APRIL. Blood 109, 729-739.

Gordon, N. C., Pan, B., Hymowitz, S. G., Yin, J., Kelley, R. F., Cochran, A. G., Yan, M., Dixit, V. M., Fairbrother, W. J., and Starovasnik, M. A. (2003). BAFF/BLyS receptor 3 comprises a minimal TNF receptor-like module that encodes a highly focused ligand-binding site. Biochemistry 42, 5977-5983.

Greenstein, S., Krett, N. L., Kurosawa, Y., Ma, C., Chauhan, D., Hideshima, T., Anderson, K. C., and Rosen, S. T. (2003). Characterization of the MM.1 human multiple myeloma (MM) cell lines: a model system to elucidate the characteristics, behavior, and signaling of steroid-sensitive and -resistant MM cells. Exp Hematol 31, 271-282.

Jacobi, A. M., Huang, W., Wang, T., Freimuth, W., Sanz, I., Furie, R., Mackay, M., Aranow, C., Diamond, B., and Davidson, A. (2010). Effect of long-term belimumab treatment on B cells in systemic lupus erythematosus: extension of a phase II, double-blind, placebo-controlled, dose-ranging study. Arthritis Rheum 62, 201-210.

Kapoor, P., Ramakrishnan, V., and Rajkumar, S. V. (2012). Bortezomib combination therapy in multiple myeloma. Semin Hematol 49, 228-242.

Keyser, F. D. (2011). Choice of Biologic Therapy for Patients with Rheumatoid Arthritis: The Infection Perspective. Curr Rheumatol Rev 7, 77-87.

Laskowski, R. A. (2009). PDBsum new things. Nucleic Acids Res 37, D355-359.

Mackay, F., Schneider, P., Rennert, P., and Browning, J. (2003). BAFF AND APRIL: a tutorial on B cell survival. Annu Rev Immunol 21, 231-264.

Nimmerjahn, F., and Ravetch, J. V. (2008). Fcgamma receptors as regulators of immune responses. Nat Rev Immunol 8, 34-47.

Novak, A. J., Darce, J. R., Arendt, B. K., Harder, B., Henderson, K., Kindsvogel, W., Gross, J. A., Greipp, P. R., and Jelinek, D. F. (2004). Expression of BCMA, TACI, and BAFF-R in multiple myeloma: a mechanism for growth and survival. Blood 103, 689-694.

Queen et al., 1989; WO 90/07861

Patel, D. R., Wallweber, H. J., Yin, J., Shriver, S. K., Marsters, S. A., Gordon, N. C., Starovasnik, M. A., and Kelley, R. F. (2004). Engineering an APRIL-specific B cell maturation antigen. J Biol Chem 279, 16727-16735.

Presta, L. G. (2008). Molecular engineering and design of therapeutic antibodies. Curr Opin Immunol 20, 460-470.

Raab, M. S., Podar, K., Breitkreutz, I., Richardson, P. G., and Anderson, K. C. (2009). Multiple myeloma. Lancet 374, 324-339.

Richardson et al. (2003) New Engl J Med 348:2609-2617.

Ryan et al (Molecular Cancer Therapeutics, 2007 6(11), 3009)

Roopenian, D. C., and Akilesh, S. (2007). FcRn: the neonatal Fc receptor comes of age. Nat Rev Immunol 7, 715-725.

Suzuki, K. (2013). Current therapeutic strategy for multiple myeloma. Jpn J Clin Oncol 43, 116-124.

Thorpe et al., 1982, Immunol. Rev. 62:119-58

Wang, S. Y., and Weiner, G. (2008). Complement and cellular cytotoxicity in antibody therapy of cancer. Expert Opin Biol Ther 8, 759-768.

Woyke et al. (2001) Antimicrob. Agents and Chemother. 45(12):3580-3584

What is claimed is:

1. A method of treating a human subject to trigger cytotoxicity in pathogenic B cells expressing B cell maturation antigen (BCMA) or pathogenic plasma cells expressing BCMA, the method comprising administering to the subject an antibody fragment comprising:
   (a) a VH domain that comprises:
      CDR1 sequence RYWIS (SEQ ID NO: 18) or RYWES (SEQ ID NO. 19);
      CDR2 sequence EINPNSSTINYAPSLKDK (SEQ ID NO: 20) or EINPSSSTINYAPSLKDK (SEQ ID NO: 21); and
      CDR3 sequence SLYYDYGDAYDYW (SEQ ID NO. 22); and
   (b) a VL domain that comprises:
      CDR1 sequence KASQSVX$_1$X$_2$NVA (SEQ ID NO. 23), wherein X$_1$X$_2$ is ES;
      CDR2 sequence SASLRFS (SEQ ID NO 24); and
      CDR3 sequence QQYNNYPLTFG (SEQ ID NO. 25), wherein said antibody or antibody fragment binds an epitope of the extracellular domain of CD269 (BCMA).

2. The method of claim 1, wherein the administering is effective to treat a cancer of plasma cells or a cancer of B lymphocytes.

3. The method of claim 1, wherein the subject has an autoimmune disease associated with autoreactive plasma cells and/or autoreactive memory B cells.

4. The method of claim 2, wherein said cancer of B lymphocytes is Hodgkin's disease.

5. The method of claim 2, wherein said cancer of plasma cells is multiple myeloma, plasmacytoma, Waldenström macroglobulinemia or plasma cell leukemia.

6. The method of claim 1, wherein the subject has an inflammatory autoimmune disease.

7. The method of claim 6, wherein the inflammatory autoimmune disease is systemic lupus erythematosus (SLE) or rheumatic arthritis.

8. The method of claim 1, wherein the antibody or antibody fragment is in an antibody-drug conjugate (ADC) comprising the antibody or antibody fragment conjugated to a therapeutic agent.

9. The method of claim 1, wherein the antibody or antibody fragment comprises a VH domain that comprises the sequence of SEQ ID NO. 6, SEQ ID NO. 7, SEQ ID NO. 8 or SEQ ID NO. 9.

10. The method of claim 1, wherein the VL domain comprises the sequence of SEQ ID NO. 14.

11. The method of claim 1, wherein the antibody binds an epitope of the N-terminus of CD269, wherein the epitope consists of amino acids 13, 15, 16, 17, 18, 19, 20, 22, 23, 26, 27 or 32 of SEQ ID NO: 39.

12. The method of claim 1, wherein the antibody binding to CD269 (BCMA) disrupts BAFF-CD269 and/or APRIL-CD269 interaction.

13. The method of claim 1, wherein the antibody is glycosylated.

14. The method of claim 13, wherein the antibody comprises the sequence of SEQ ID NO: 29, and wherein the antibody comprises a glycan that is an N-linked oligosaccharide chain at Asn297 of the heavy chain consisting of the sequence of SEQ ID NO: 29.

15. The method of claim 1, wherein the antibody or antibody fragment is administered to the subject together with a pharmaceutically acceptable carrier.

16. The method of claim 1, wherein the VH domain has at least 80% sequence identity to the sequence of SEQ ID NO: 6, SEQ ID NO: 7, SEQ ID NO: 8 or SEQ ID NO: 9 and wherein the CDR sequences are those recited in claim 1.

17. The method of claim 1, wherein the VH domain has at least 90% sequence identity to the sequence of SEQ ID NO; 6, SEQ ID NO: 7, SEQ ID NO: 8 or SEQ ID NO: 9 and wherein the CDR sequences are those recited in claim 1.

\* \* \* \* \*

UNITED STATES PATENT AND TRADEMARK OFFICE
CERTIFICATE OF CORRECTION

| | | |
|---|---|---|
| PATENT NO. | : 10,851,172 B2 | Page 1 of 5 |
| APPLICATION NO. | : 16/170575 | |
| DATED | : December 1, 2020 | |
| INVENTOR(S) | : Felix Oden et al. | |

It is certified that error appears in the above-identified patent and that said Letters Patent is hereby corrected as shown below:

On the Title Page

Column 2, Item (56), Line 10, under Other Publications, delete "2015)." and insert --2015.--.

Column 2, under Other Publications, Line 6, delete "B cell" and insert --B-cell--.

Column 2, Item (57), under Abstract, Line 2, delete "B cells expressing B cell" and insert --B-cells expressing B-cell--.

In the Specification

In Column 1, Line 22, delete "B cell" and insert --B-cell--.

In Column 1, Line 24, delete "B cell" and insert --B-cell--.

In Column 1, Line 28, delete "B cell" and insert --B-cell--.

In Column 1, Line 31, delete "B cell" and insert --B-cell--.

In Column 2, Line 25, delete "B cell" and insert --B-cell--.

In Column 2, Line 26, delete "B cell" and insert --B-cell--.

In Column 2, Line 41, delete "cyclophosphamid" and insert --cyclophosphamide--.

In Column 2, Line 56, delete "B cell" and insert --B-cell--.

In Column 2, Line 60, delete "B cell" and insert --B-cell--.

In Column 3, Line 37, delete "Y." and insert --Y,--.

Signed and Sealed this
Twenty-second Day of June, 2021

Drew Hirshfeld
*Performing the Functions and Duties of the*
*Under Secretary of Commerce for Intellectual Property and*
*Director of the United States Patent and Trademark Office*

In Column 3, Line 37, delete "T)" and insert --T--.

In Column 5, Line 1, delete "Y." and insert --Y,--.

In Column 5, Line 29, delete "Z," and insert --$Z_1$--.

In Column 5, Line 30, delete "$FX_{13}1$" and insert --$FX_{13}I$--.

In Column 5, Line 37, delete "Y." and insert --Y,--.

In Column 6, Line 59, delete "Y." and insert --Y,--.

In Column 8, Line 56, delete "LCmouse" and insert --LC mouse--.

In Column 9, Line 47, delete "sequence.)" and insert --sequence.--.

In Column 23, Line 30, delete "Defucolylation" and insert --Defucosylation--.

In Column 25, Line 57, delete "NSO," and insert --$NS_0$,--.

In Column 26, Line 57, delete "(See" and insert --See--.

In Column 27, Line 21, delete "Phytolaca" and insert --Phytolacca--.

In Column 27, Line 22, delete "Momordica" and insert --momordica--.

In Column 27, Line 23, delete "Sapaonaria" and insert --Saponaria--.

In Column 27, Line 42, delete "combretatstatin," and insert --combretastatin,--.

In Column 27, Line 42, delete "chalicheamicin," and insert --calicheamicin,--.

In Column 27, Lines 45-46, delete "cryptophysin," and insert --cryptophycin,--.

In Column 27, Line 48, delete "phenylened-iamine" and insert --phenylenediamine--.

In Column 27, Line 52, delete "colcimid," and insert --colcemid,--.

In Column 27, Line 55, delete "dolostatin" and insert --dolastatin--.

In Column 28, Line 6, delete "dolaisoleuine" and insert --dolaisoleucine--.

In Column 28, Line 17, delete "mitototic" and insert --mitotic--.

In Column 28, Line 23, delete "drugs drugs" and insert --drugs--.

In Column 28, Line 53, delete "streptozoicin," and insert --streptozotocin,--.

In Column 31, Line 3, delete "cutanous" and insert --cutaneous--.

In Column 31, Line 7, delete "Hennoch" and insert --Henoch--.

In Column 31, Line 11, delete "ateritis," and insert --arteritis,--.

In Column 31, Line 12, delete "Eythema" and insert --Erythema--.

In Column 31, Line 42 (Approx.), delete "Y." and insert --Y,--.

In Column 32, Line 8, delete "Autoimmunthrombocytopenia," and insert --Autoimmunethrombocytopenia,--.

In Column 32, Line 8, delete "Autoimmunneutropenia," and insert --Autoimmuneneutropenia,--.

In Column 32, Line 9, delete "Autoimmunhemolytic" and insert --Autoimmunehemolytic--.

In Column 32, Lines 9-10, delete "Autoimmunlymphocytopenia" and insert --Autoimmunelymphocytopenia--.

In Column 32, Line 11, delete "atropic" and insert --atrophic--.

In Column 32, Line 12, delete "disase," and insert --disease,--.

In Column 33, Line 57 (Approx.), delete "Y." and insert --Y,--.

In Column 37, Line 9, delete "tacgact" and insert --TACGACT--.

In Columns 41-42, Line 17 (Approx.), delete "BCNA" and insert --BCMA--.

In Columns 41-42, Line 24 (Approx.), delete "XI" and insert --X1--.

In Columns 41-42, Line 24 (Approx.), delete "E:" and insert --E;--.

In Columns 41-42, Line 24 (Approx.), delete "K." and insert --K,--.

In Columns 41-42, Line 25 (Approx.), delete "T:" and insert --T;--.

In Columns 41-42, Line 26 (Approx.), delete "D." and insert --D,--.

In Columns 41-42, Line 26 (Approx.), delete "G:" and insert --G;--.

In Columns 41-42, Line 26 (Approx.), delete "K." and insert --K,--.

In Columns 41-42, Line 29 (Approx.), delete "1" and insert --I--.

In Column 43, Line 2, delete "(Gordon" and insert --Gordon--.

In Column 43, Line 6, delete "B cell" and insert --B-cell--.

In Column 48, Line 44, delete "cynomlgous" and insert --cynomolgus--.

In Column 48, Line 48, delete "cynomlgous" and insert --cynomolgus--.

In Column 50, Line 23, delete "(Organo Technie)." and insert --(Organotechnie).--.

In Column 50, Line 29, delete "µI" and insert --µl--.

In Column 50, Line 50, delete "µI" and insert --µl--.

In Column 51, Line 62, delete "Helmoltz" and insert --Helmholtz--.

In Column 52, Line 20, delete "µI" and insert --µl--.

In Column 52, Line 22, delete "µI" and insert --µl--.

In Column 52, Line 24, delete "µI." and insert --µl.--.

In Column 52, Line 28, delete "1" and insert --1%--.

In Column 52, Line 29, delete "µI" and insert --µl--.

In Column 52, Line 38, delete "Il2rgtm1Wjl" and insert --Il2rgtmlWjl--.

In Column 53, Line 40, delete "($k_011$)" and insert --($k_{off}$)--.

In Column 53, Line 63, delete "316" and insert --316.--.

In Column 54, under References, Line 22, delete "B cell" and insert --B-cell--.

In Column 54, under References, Line 34, delete "B cell" and insert --B-cell--.

In Column 54, Line 44, delete "90/07861" and insert --90/07861.--.

In Column 54, under References, Lines 47-48, delete "B cell" and insert --B-cell--.

In Column 54, Line 56, delete "3009)" and insert --3009).--.

In Column 55, Line 62, delete "58" and insert --58.--.

CERTIFICATE OF CORRECTION (continued)
U.S. Pat. No. 10,851,172 B2

In Column 55, Line 67, delete "3584" and insert --3584.--.

In the Claims

In Column 97, Claim 1, Line 39, delete "B cells expressing B cell" and insert --B-cells expressing B cell--.

In Column 97, Claim 1, Line 42, delete "antibody fragment" and insert --antibody or antibody fragment--.

In Column 97, Claim 1, Line 44, delete "RYWES" and insert --RYWFS--.

In Column 97, Claim 1, Line 47, delete "NO" and insert --NO.--.

In Column 97, Claim 1, Line 48 (Approx.), delete "NO" and insert --NO.--.

In Column 97, Claim 3, Line 62, delete "B cell" and insert --B-cell--.

In Column 99, Claim 17, Line 7, delete "NO;" and insert --NO.--.

SEQUENCE LISTING

<160> NUMBER OF SEQ ID NOS: 43

<210> SEQ ID NO 1
<211> LENGTH: 120
<212> TYPE: PRT
<213> ORGANISM: Artificial Sequence
<220> FEATURE:
<223> OTHER INFORMATION: Synthetic peptide

<400> SEQUENCE: 1

Gln Val Gln Leu Gln Gln Ser Gly Gly Gly Leu Val Gln Pro Gly Gly
1               5                   10                  15

Ser Leu Lys Leu Ser Cys Ala Ala Ser Gly Ile Asp Phe Ser Arg Tyr
            20                  25                  30

Trp Met Ser Trp Val Arg Arg Ala Pro Gly Lys Gly Leu Glu Trp Ile
        35                  40                  45

Gly Glu Ile Asn Pro Asp Ser Ser Thr Ile Asn Tyr Ala Pro Ser Leu
    50                  55                  60

Lys Asp Lys Phe Ile Ile Ser Arg Asp Asn Ala Lys Asn Thr Leu Tyr
65                  70                  75                  80

Leu Gln Met Ser Lys Val Arg Ser Glu Asp Thr Ala Leu Tyr Tyr Cys
                85                  90                  95

Ala Ser Leu Tyr Tyr Asp Tyr Gly Asp Ala Met Asp Tyr Trp Gly Gln
            100                 105                 110

Gly Thr Ser Val Thr Val Ser Ser
        115                 120

<210> SEQ ID NO 2
<211> LENGTH: 120
<212> TYPE: PRT
<213> ORGANISM: Artificial Sequence
<220> FEATURE:
<223> OTHER INFORMATION: Synthetic peptide

<400> SEQUENCE: 2

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asp Asp Tyr
            20                  25                  30

Trp Met Ser Trp Val Arg Gln Ala Pro Gly Lys Gly Leu Glu Trp Val
        35                  40                  45

Gly Glu Ile Asn Pro Asp Ser Ser Thr Ile Asn Tyr Ala Pro Ser Leu
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ser Leu Tyr Tyr Asp Tyr Gly Asp Ala Met Asp Tyr Trp Gly Gln
            100                 105                 110

Gly Thr Leu Val Thr Val Ser Ser
        115                 120

<210> SEQ ID NO 3
<211> LENGTH: 120
<212> TYPE: PRT
<213> ORGANISM: Artificial Sequence
<220> FEATURE:
<223> OTHER INFORMATION: Synthetic peptide

<400> SEQUENCE: 3

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Arg Tyr
            20                  25                  30

Trp Met Ser Trp Val Arg Gln Ala Pro Gly Lys Gly Leu Val Trp Val
        35                  40                  45

Gly Glu Ile Asn Pro Asp Ser Ser Thr Ile Asn Tyr Ala Pro Ser Leu
    50                  55                  60

Lys Asp Lys Phe Thr Ile Ser Arg Asp Asn Ala Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ser Leu Tyr Tyr Asp Tyr Gly Asp Ala Met Asp Tyr Trp Gly Gln
            100                 105                 110

Gly Thr Leu Val Thr Val Ser Ser
        115                 120
```

```
<210> SEQ ID NO 4
<211> LENGTH: 120
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (34)..(34)
<223> OTHER INFORMATION: Xaa can be any naturally occurring amino acid
<220> FEATURE:
<221> NAME/KEY: misc_feature
<222> LOCATION: (54)..(55)
<223> OTHER INFORMATION: Xaa can be any naturally occurring amino acid
<220> FEATURE:
<221> NAME/KEY: misc_feature
<222> LOCATION: (101)..(101)
<223> OTHER INFORMATION: Xaa can be any naturally occurring amino acid
<220> FEATURE:
<221> NAME/KEY: misc_feature
<222> LOCATION: (107)..(107)
<223> OTHER INFORMATION: Xaa can be any naturally occurring amino acid

<400> SEQUENCE: 4

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Arg Tyr
            20                  25                  30

Trp Xaa Ser Trp Val Arg Gln Ala Pro Gly Lys Gly Leu Val Trp Val
        35                  40                  45

Gly Glu Ile Asn Pro Xaa Xaa Ser Thr Ile Asn Tyr Ala Pro Ser Leu
    50                  55                  60

Lys Asp Lys Phe Thr Ile Ser Arg Asp Asn Ala Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ser Leu Tyr Xaa Asp Tyr Gly Asp Ala Xaa Asp Tyr Trp Gly Gln
            100                 105                 110

Gly Thr Leu Val Thr Val Ser Ser
        115                 120

<210> SEQ ID NO 5
<211> LENGTH: 120
<212> TYPE: PRT
```

```
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (33)..(33)
<223> OTHER INFORMATION: Xaa can be any naturally occurring amino acid
<220> FEATURE:
<221> NAME/KEY: misc_feature
<222> LOCATION: (35)..(35)
<223> OTHER INFORMATION: Xaa can be any naturally occurring amino acid
<220> FEATURE:
<221> NAME/KEY: misc_feature
<222> LOCATION: (47)..(47)
<223> OTHER INFORMATION: Xaa can be any naturally occurring amino acid
<220> FEATURE:
<221> NAME/KEY: misc_feature
<222> LOCATION: (50)..(50)
<223> OTHER INFORMATION: Xaa can be any naturally occurring amino acid
<220> FEATURE:
<221> NAME/KEY: misc_feature
<222> LOCATION: (99)..(101)
<223> OTHER INFORMATION: Xaa can be any naturally occurring amino acid
<220> FEATURE:
<221> NAME/KEY: misc_feature
<222> LOCATION: (106)..(106)
<223> OTHER INFORMATION: Xaa can be any naturally occurring amino acid

<400> SEQUENCE: 5

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Arg Tyr
            20                  25                  30

Xaa Met Xaa Trp Val Arg Gln Ala Pro Gly Lys Gly Leu Val Xaa Val
        35                  40                  45

Gly Xaa Ile Asn Pro Asp Ser Ser Thr Ile Asn Tyr Ala Pro Ser Leu
    50                  55                  60

Lys Asp Lys Phe Thr Ile Ser Arg Asp Asn Ala Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ser Xaa Xaa Xaa Asp Tyr Gly Asp Xaa Met Asp Tyr Trp Gly Gln
            100                 105                 110

Gly Thr Leu Val Thr Val Ser Ser
        115                 120

<210> SEQ ID NO 6
<211> LENGTH: 120
<212> TYPE: PRT
<213> ORGANISM: Artificial Sequence
<220> FEATURE:
<223> OTHER INFORMATION: Synthetic peptide

<400> SEQUENCE: 6

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Arg Tyr
            20                  25                  30

Trp Ile Ser Trp Val Arg Gln Ala Pro Gly Lys Gly Leu Val Trp Val
        35                  40                  45

Gly Glu Ile Asn Pro Asn Ser Ser Thr Ile Asn Tyr Ala Pro Ser Leu
    50                  55                  60

Lys Asp Lys Phe Thr Ile Ser Arg Asp Asn Ala Lys Asn Thr Leu Tyr
65                  70                  75                  80
```

```
Leu Gln Met Asn Ser Leu Arg Ala Glu Asp Thr Ala Val Tyr Tyr Cys
                85                  90                  95

Ala Ser Leu Tyr Tyr Asp Tyr Gly Asp Ala Tyr Asp Tyr Trp Gly Gln
            100                 105                 110

Gly Thr Leu Val Thr Val Ser Ser
        115                 120

<210> SEQ ID NO 7
<211> LENGTH: 120
<212> TYPE: PRT
<213> ORGANISM: Artificial Sequence
<220> FEATURE:
<223> OTHER INFORMATION: Synthetic peptide

<400> SEQUENCE: 7

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Arg Tyr
            20                  25                  30

Trp Phe Ser Trp Val Arg Gln Ala Pro Gly Lys Gly Leu Val Trp Val
        35                  40                  45

Gly Glu Ile Asn Pro Asn Ser Ser Thr Ile Asn Tyr Ala Pro Ser Leu
    50                  55                  60

Lys Asp Lys Phe Thr Ile Ser Arg Asp Asn Ala Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ser Leu Tyr Tyr Asp Tyr Gly Asp Ala Tyr Asp Tyr Trp Gly Gln
            100                 105                 110

Gly Thr Leu Val Thr Val Ser Ser
        115                 120

<210> SEQ ID NO 8
<211> LENGTH: 120
<212> TYPE: PRT
<213> ORGANISM: Artificial Sequence
<220> FEATURE:
<223> OTHER INFORMATION: Synthetic peptide

<400> SEQUENCE: 8

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Arg Tyr
            20                  25                  30

Trp Ile Ser Trp Val Arg Gln Ala Pro Gly Lys Gly Leu Val Trp Val
        35                  40                  45

Gly Glu Ile Asn Pro Ser Ser Ser Thr Ile Asn Tyr Ala Pro Ser Leu
    50                  55                  60

Lys Asp Lys Phe Thr Ile Ser Arg Asp Asn Ala Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ser Leu Tyr Tyr Asp Tyr Gly Asp Ala Tyr Asp Tyr Trp Gly Gln
            100                 105                 110

Gly Thr Leu Val Thr Val Ser Ser
        115                 120

<210> SEQ ID NO 9
```

<211> LENGTH: 120
<212> TYPE: PRT
<213> ORGANISM: Artificial Sequence
<220> FEATURE:
<223> OTHER INFORMATION: Synthetic peptide

<400> SEQUENCE: 9

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Arg Tyr
            20                  25                  30

Trp Phe Ser Trp Val Arg Gln Ala Pro Gly Lys Gly Leu Val Trp Val
        35                  40                  45

Gly Glu Ile Asn Pro Ser Ser Ser Thr Ile Asn Tyr Ala Pro Ser Leu
    50                  55                  60

Lys Asp Lys Phe Thr Ile Ser Arg Asp Asn Ala Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ser Leu Tyr Tyr Asp Tyr Gly Asp Ala Tyr Asp Tyr Trp Gly Gln
            100                 105                 110

Gly Thr Leu Val Thr Val Ser Ser
        115                 120

<210> SEQ ID NO 10
<211> LENGTH: 108
<212> TYPE: PRT
<213> ORGANISM: Artificial Sequence
<220> FEATURE:
<223> OTHER INFORMATION: Synthetic peptide

<400> SEQUENCE: 10

Asp Ile Val Met Thr Gln Ser Pro Ala Thr Leu Ser Val Ser Val Gly
1               5                   10                  15

Asp Glu Val Thr Leu Thr Cys Lys Ala Ser Gln Ser Val Asp Ser Asn
            20                  25                  30

Val Ala Trp Tyr Gln Gln Lys Pro Gly Gln Ala Pro Lys Leu Leu Ile
        35                  40                  45

Tyr Ser Asp Asp Leu Arg Phe Ser Gly Val Pro Ala Arg Phe Ser Gly
    50                  55                  60

Ser Gly Ser Gly Thr Asp Phe Thr Leu Thr Ile Ser Ser Leu Gln Ser
65                  70                  75                  80

Glu Asp Phe Ala Val Tyr Tyr Cys Gln Gln Tyr Asn Asn Tyr Pro Leu
                85                  90                  95

Thr Phe Gly Ala Gly Thr Lys Leu Glu Leu Lys Arg
            100                 105

<210> SEQ ID NO 11
<211> LENGTH: 108
<212> TYPE: PRT
<213> ORGANISM: Artificial Sequence
<220> FEATURE:
<223> OTHER INFORMATION: Synthetic peptide

<400> SEQUENCE: 11

Glu Ile Val Met Thr Gln Ser Pro Ala Thr Leu Ser Val Ser Pro Gly
1               5                   10                  15

Glu Arg Ala Thr Leu Ser Cys Lys Ala Ser Gln Ser Val Asp Ser Asn
            20                  25                  30

Val Ala Trp Tyr Gln Gln Lys Pro Gly Gln Ala Pro Arg Ala Leu Ile
            35                  40                  45

Tyr Ser Ala Ser Leu Arg Phe Ser Gly Ile Pro Ala Arg Phe Ser Gly
 50                  55                  60

Ser Gly Ser Gly Thr Glu Phe Thr Leu Thr Ile Ser Ser Leu Gln Ser
 65                  70                  75                  80

Glu Asp Phe Ala Val Tyr Tyr Cys Gln Gln Tyr Asn Asn Tyr Pro Leu
                 85                  90                  95

Thr Phe Gly Ala Gly Thr Lys Leu Glu Leu Lys Arg
             100                 105

<210> SEQ ID NO 12
<211> LENGTH: 108
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (30)..(31)
<223> OTHER INFORMATION: Xaa can be any naturally occurring amino acid

<400> SEQUENCE: 12

Glu Ile Val Met Thr Gln Ser Pro Ala Thr Leu Ser Val Ser Pro Gly
 1               5                  10                  15

Glu Arg Ala Thr Leu Ser Cys Lys Ala Ser Gln Ser Val Xaa Xaa Asn
             20                  25                  30

Val Ala Trp Tyr Gln Gln Lys Pro Gly Gln Ala Pro Arg Ala Leu Ile
            35                  40                  45

Tyr Ser Ala Ser Leu Arg Phe Ser Gly Ile Pro Ala Arg Phe Ser Gly
 50                  55                  60

Ser Gly Ser Gly Thr Glu Phe Thr Leu Thr Ile Ser Ser Leu Gln Ser
 65                  70                  75                  80

Glu Asp Phe Ala Val Tyr Tyr Cys Gln Gln Tyr Asn Asn Tyr Pro Leu
                 85                  90                  95

Thr Phe Gly Ala Gly Thr Lys Leu Glu Leu Lys Arg
             100                 105

<210> SEQ ID NO 13
<211> LENGTH: 108
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (31)..(32)
<223> OTHER INFORMATION: Xaa can be any naturally occurring amino acid
<220> FEATURE:
<221> NAME/KEY: misc_feature
<222> LOCATION: (34)..(34)
<223> OTHER INFORMATION: Xaa can be any naturally occurring amino acid
<220> FEATURE:
<221> NAME/KEY: misc_feature
<222> LOCATION: (36)..(36)
<223> OTHER INFORMATION: Xaa can be any naturally occurring amino acid
<220> FEATURE:
<221> NAME/KEY: misc_feature
<222> LOCATION: (49)..(50)
<223> OTHER INFORMATION: Xaa can be any naturally occurring amino acid
<220> FEATURE:
<221> NAME/KEY: misc_feature
<222> LOCATION: (52)..(53)
<223> OTHER INFORMATION: Xaa can be any naturally occurring amino acid
<220> FEATURE:
<221> NAME/KEY: misc_feature

```
<222> LOCATION: (55)..(55)
<223> OTHER INFORMATION: Xaa can be any naturally occurring amino acid
<220> FEATURE:
<221> NAME/KEY: misc_feature
<222> LOCATION: (66)..(67)
<223> OTHER INFORMATION: Xaa can be any naturally occurring amino acid
<220> FEATURE:
<221> NAME/KEY: misc_feature
<222> LOCATION: (89)..(89)
<223> OTHER INFORMATION: Xaa can be any naturally occurring amino acid
<220> FEATURE:
<221> NAME/KEY: misc_feature
<222> LOCATION: (91)..(91)
<223> OTHER INFORMATION: Xaa can be any naturally occurring amino acid
<220> FEATURE:
<221> NAME/KEY: misc_feature
<222> LOCATION: (94)..(94)
<223> OTHER INFORMATION: Xaa can be any naturally occurring amino acid
<220> FEATURE:
<221> NAME/KEY: misc_feature
<222> LOCATION: (96)..(96)
<223> OTHER INFORMATION: Xaa can be any naturally occurring amino acid

<400> SEQUENCE: 13

Glu Ile Val Met Thr Gln Ser Pro Ala Thr Leu Ser Val Ser Pro Gly
1               5                   10                  15

Glu Arg Ala Thr Leu Ser Cys Lys Ala Ser Gln Ser Val Asp Xaa Xaa
            20                  25                  30

Val Xaa Trp Xaa Gln Gln Lys Pro Gly Gln Ala Pro Arg Ala Leu Ile
        35                  40                  45

Xaa Xaa Ala Xaa Xaa Arg Xaa Ser Gly Ile Pro Ala Arg Phe Ser Gly
    50                  55                  60

Ser Xaa Xaa Gly Thr Glu Phe Thr Leu Thr Ile Ser Ser Leu Gln Ser
65                  70                  75                  80

Glu Asp Phe Ala Val Tyr Tyr Cys Xaa Gln Xaa Asn Asn Xaa Pro Xaa
                85                  90                  95

Thr Phe Gly Ala Gly Thr Lys Leu Glu Leu Lys Arg
            100                 105

<210> SEQ ID NO 14
<211> LENGTH: 108
<212> TYPE: PRT
<213> ORGANISM: Artificial Sequence
<220> FEATURE:
<223> OTHER INFORMATION: Synthetic peptide

<400> SEQUENCE: 14

Glu Ile Val Met Thr Gln Ser Pro Ala Thr Leu Ser Val Ser Pro Gly
1               5                   10                  15

Glu Arg Ala Thr Leu Ser Cys Lys Ala Ser Gln Ser Val Glu Ser Asn
            20                  25                  30

Val Ala Trp Tyr Gln Gln Lys Pro Gly Gln Ala Pro Arg Ala Leu Ile
        35                  40                  45

Tyr Ser Ala Ser Leu Arg Phe Ser Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asn Asn Tyr Pro Leu
                85                  90                  95

Thr Phe Gly Ala Gly Thr Lys Leu Glu Leu Lys Arg
            100                 105

<210> SEQ ID NO 15
```

```
<211> LENGTH: 5
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (4)..(4)
<223> OTHER INFORMATION: Xaa can be any naturally occurring amino acid

<400> SEQUENCE: 15

Arg Tyr Trp Xaa Ser
1               5

<210> SEQ ID NO 16
<211> LENGTH: 18
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (5)..(6)
<223> OTHER INFORMATION: Xaa can be any naturally occurring amino acid

<400> SEQUENCE: 16

Glu Ile Asn Pro Xaa Xaa Ser Thr Ile Asn Tyr Ala Pro Ser Leu Lys
1               5                   10                  15

Asp Lys

<210> SEQ ID NO 17
<211> LENGTH: 13
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (10)..(10)
<223> OTHER INFORMATION: Xaa can be any naturally occurring amino acid

<400> SEQUENCE: 17

Ser Leu Tyr Xaa Asp Tyr Gly Asp Ala Xaa Asp Tyr Trp
1               5                   10

<210> SEQ ID NO 18
<211> LENGTH: 5
<212> TYPE: PRT
<213> ORGANISM: Artificial Sequence
<220> FEATURE:
<223> OTHER INFORMATION: Synthetic peptide

<400> SEQUENCE: 18

Arg Tyr Trp Ile Ser
1               5

<210> SEQ ID NO 19
<211> LENGTH: 5
<212> TYPE: PRT
<213> ORGANISM: Artificial Sequence
<220> FEATURE:
<223> OTHER INFORMATION: Synthetic peptide

<400> SEQUENCE: 19

Arg Tyr Trp Phe Ser
```

-continued

```
<210> SEQ ID NO 20
<211> LENGTH: 18
<212> TYPE: PRT
<213> ORGANISM: Artificial Sequence
<220> FEATURE:
<223> OTHER INFORMATION: Synthetic peptide

<400> SEQUENCE: 20

Glu Ile Asn Pro Asn Ser Ser Thr Ile Asn Tyr Ala Pro Ser Leu Lys
1               5                   10                  15
Asp Lys

<210> SEQ ID NO 21
<211> LENGTH: 18
<212> TYPE: PRT
<213> ORGANISM: Artificial Sequence
<220> FEATURE:
<223> OTHER INFORMATION: Synthetic peptide

<400> SEQUENCE: 21

Glu Ile Asn Pro Ser Ser Ser Thr Ile Asn Tyr Ala Pro Ser Leu Lys
1               5                   10                  15
Asp Lys

<210> SEQ ID NO 22
<211> LENGTH: 13
<212> TYPE: PRT
<213> ORGANISM: Artificial Sequence
<220> FEATURE:
<223> OTHER INFORMATION: Synthetic peptide

<400> SEQUENCE: 22

Ser Leu Tyr Tyr Asp Tyr Gly Asp Ala Tyr Asp Tyr Trp
1               5                   10

<210> SEQ ID NO 23
<211> LENGTH: 11
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (7)..(8)
<223> OTHER INFORMATION: Xaa can be any naturally occurring amino acid

<400> SEQUENCE: 23

Lys Ala Ser Gln Ser Val Xaa Xaa Asn Val Ala
1               5                   10

<210> SEQ ID NO 24
<211> LENGTH: 7
<212> TYPE: PRT
<213> ORGANISM: Artificial Sequence
<220> FEATURE:
<223> OTHER INFORMATION: Synthetic peptide

<400> SEQUENCE: 24

Ser Ala Ser Leu Arg Phe Ser
1               5

<210> SEQ ID NO 25
<211> LENGTH: 11
<212> TYPE: PRT
```

<210> SEQ ID NO 26
<211> LENGTH: 11
<212> TYPE: PRT
<213> ORGANISM: Artificial Sequence
<220> FEATURE:
<223> OTHER INFORMATION: Synthetic peptide

<400> SEQUENCE: 25

```
Gln Gln Tyr Asn Asn Tyr Pro Leu Thr Phe Gly
1               5                   10
```

<210> SEQ ID NO 26
<211> LENGTH: 11
<212> TYPE: PRT
<213> ORGANISM: Artificial Sequence
<220> FEATURE:
<223> OTHER INFORMATION: Synthetic peptide

<400> SEQUENCE: 26

```
Lys Ala Ser Gln Ser Val Asp Ser Asn Val Ala
1               5                   10
```

<210> SEQ ID NO 27
<211> LENGTH: 450
<212> TYPE: PRT
<213> ORGANISM: Artificial Sequence
<220> FEATURE:
<223> OTHER INFORMATION: Synthetic peptide

<400> SEQUENCE: 27

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Arg Tyr
            20                  25                  30

Trp Met Ser Trp Val Arg Gln Ala Pro Gly Lys Gly Leu Val Trp Val
        35                  40                  45

Gly Glu Ile Asn Pro Asp Ser Ser Thr Ile Asn Tyr Ala Pro Ser Leu
    50                  55                  60

Lys Asp Lys Phe Thr Ile Ser Arg Asp Asn Ala Lys Asn Thr Leu Tyr
65                  70                  75                  80

Leu Gln Met Asn Ser Leu Arg Ala Glu Asp Thr Ala Val Tyr Tyr Cys
            85                  90                  95

Ala Ser Leu Tyr Tyr Asp Tyr Gly Asp Ala Met Asp Tyr Trp Gly Gln
        100                 105                 110

Gly Thr Leu Val Thr Val Ser Ser Ala Ser Thr Lys Gly Pro Ser Val
    115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
            165                 170                 175

Leu Gln Ser Ser Gly Leu Tyr Ser Leu Ser Ser Val Val Thr Val Pro
        180                 185                 190

Ser Ser Ser Leu Gly Thr Gln Thr Tyr Ile Cys Asn Val Asn His Lys
    195                 200                 205

Pro Ser Asn Thr Lys Val Asp Lys Arg Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
            245                 250                 255
```

```
Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 28
<211> LENGTH: 450
<212> TYPE: PRT
<213> ORGANISM: Artificial Sequence
<220> FEATURE:
<223> OTHER INFORMATION: Synthetic peptide

<400> SEQUENCE: 28

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Arg Tyr
            20                  25                  30

Trp Phe Ser Trp Val Arg Gln Ala Pro Gly Lys Gly Leu Val Trp Val
        35                  40                  45

Gly Glu Ile Asn Pro Ser Ser Ser Thr Ile Asn Tyr Ala Pro Ser Leu
    50                  55                  60

Lys Asp Lys Phe Thr Ile Ser Arg Asp Asn Ala Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ser Leu Tyr Tyr Asp Tyr Gly Asp Ala Tyr Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160
```

Trp Asn Ser Gly Ala Leu Thr Ser Gly Val His Thr Phe Pro Ala Val
            165                 170                 175

Leu Gln Ser Ser Gly Leu Tyr Ser Leu Ser Ser Val Val Thr Val Pro
        180                 185                 190

Ser Ser Ser Leu Gly Thr Gln Thr Tyr Ile Cys Asn Val Asn His Lys
    195                 200                 205

Pro Ser Asn Thr Lys Val Asp Lys Arg Val Glu Pro Lys Ser Cys Asp
210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
            245                 250                 255

Ser Arg Thr Pro Glu Val Thr Cys Val Val Val Asp Val Ser His Glu
        260                 265                 270

Asp Pro Glu Val Lys Phe Asn Trp Tyr Val Asp Gly Val Glu Val His
    275                 280                 285

Asn Ala Lys Thr Lys Pro Arg Glu Glu Gln Tyr Asn Ser Thr Tyr Arg
290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
            325                 330                 335

Lys Thr Ile Ser Lys Ala Lys Gly Gln Pro Arg Glu Pro Gln Val Tyr
        340                 345                 350

Thr Leu Pro Pro Ser Arg Glu Glu Met Thr Lys Asn Gln Val Ser Leu
    355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
            405                 410                 415

Lys Ser Arg Trp Gln Gln Gly Asn Val Phe Ser Cys Ser Val Met His
        420                 425                 430

Glu Ala Leu His Asn His Tyr Thr Gln Lys Ser Leu Ser Leu Ser Pro
    435                 440                 445

Gly Lys
450

<210> SEQ ID NO 29
<211> LENGTH: 450
<212> TYPE: PRT
<213> ORGANISM: Artificial Sequence
<220> FEATURE:
<223> OTHER INFORMATION: Synthetic peptide

<400> SEQUENCE: 29

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Arg Tyr
            20                  25                  30

Trp Ile Ser Trp Val Arg Gln Ala Pro Gly Lys Gly Leu Val Trp Val
        35                  40                  45

Gly Glu Ile Asn Pro Ser Ser Ser Thr Ile Asn Tyr Ala Pro Ser Leu
    50                  55                  60

```
Lys Asp Lys Phe Thr Ile Ser Arg Asp Asn Ala Lys Asn Thr Leu Tyr
 65                  70                  75                  80

Leu Gln Met Asn Ser Leu Arg Ala Glu Asp Thr Ala Val Tyr Tyr Cys
             85                  90                  95

Ala Ser Leu Tyr Tyr Asp Tyr Gly Asp Ala Tyr Asp Tyr Trp Gly Gln
            100                 105                 110

Gly Thr Leu Val Thr Val Ser Ala Ser Thr Lys Gly Pro Ser Val
        115                 120                 125

Phe Pro Leu Ala Pro Ser Ser Lys Ser Thr Ser Gly Gly Thr Ala Ala
130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Arg Val Glu Pro Lys Ser Cys Asp
210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 30
<211> LENGTH: 214
```

```
<212> TYPE: PRT
<213> ORGANISM: Artificial Sequence
<220> FEATURE:
<223> OTHER INFORMATION: Synthetic peptide

<400> SEQUENCE: 30

Glu Ile Val Met Thr Gln Ser Pro Ala Thr Leu Ser Val Ser Pro Gly
1               5                   10                  15

Glu Arg Ala Thr Leu Ser Cys Lys Ala Ser Gln Ser Val Asp Ser Asn
            20                  25                  30

Val Ala Trp Tyr Gln Gln Lys Pro Gly Gln Ala Pro Arg Ala Leu Ile
        35                  40                  45

Tyr Ser Ala Ser Leu Arg Phe Ser Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asn Asn Tyr Pro Leu
                85                  90                  95

Thr Phe Gly Ala Gly Thr Lys Leu Glu Leu Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 31
<211> LENGTH: 214
<212> TYPE: PRT
<213> ORGANISM: Artificial Sequence
<220> FEATURE:
<223> OTHER INFORMATION: Synthetic peptide

<400> SEQUENCE: 31

Glu Ile Val Met Thr Gln Ser Pro Ala Thr Leu Ser Val Ser Pro Gly
1               5                   10                  15

Glu Arg Ala Thr Leu Ser Cys Lys Ala Ser Gln Ser Val Glu Ser Asn
            20                  25                  30

Val Ala Trp Tyr Gln Gln Lys Pro Gly Gln Ala Pro Arg Ala Leu Ile
        35                  40                  45

Tyr Ser Ala Ser Leu Arg Phe Ser Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asn Asn Tyr Pro Leu
                85                  90                  95

Thr Phe Gly Ala Gly Thr Lys Leu Glu Leu Lys Arg Thr Val Ala Ala
            100                 105                 110
```

```
          Pro Ser Val Phe Ile Phe Pro Pro Ser Asp Glu Gln Leu Lys Ser Gly
                  115                 120                 125

Thr Ala Ser Val Val Cys Leu Leu Asn Asn Phe Tyr Pro Arg Glu Ala
              130                 135                 140

Lys Val Gln Trp Lys Val Asp Asn Ala Leu Gln Ser Gly Asn Ser Gln
          145                 150                 155                 160

Glu Ser Val Thr Glu Gln Asp Ser Lys Asp Ser Thr Tyr Ser Leu Ser
                          165                 170                 175

Ser Thr Leu Thr Leu Ser Lys Ala Asp Tyr Glu Lys His Lys Val Tyr
                      180                 185                 190

Ala Cys Glu Val Thr His Gln Gly Leu Ser Ser Pro Val Thr Lys Ser
                  195                 200                 205

Phe Asn Arg Gly Glu Cys
              210

<210> SEQ ID NO 32
<211> LENGTH: 1450
<212> TYPE: DNA
<213> ORGANISM: Artificial Sequence
<220> FEATURE:
<223> OTHER INFORMATION: Synthetic coding sequence

<400> SEQUENCE: 32
gaattccacc atgggatggt catgtatcat ccttttttcta gtagcaactg caaccggtgt      60
ccacagtgaa gtgcagctgg tcgaatctgg aggaggcctg gttcagcctg gtggcagcct     120
taggctctct tgtgcagcct ctggctttac cttctcacgg tattgatga gctgggtgag      180 acaggctcca gggaaaggtc tggtgtgggt aggggagata accccgata gcagcacgat      240 caactatgct ccgtcactga agacaagtt caccatttcc cgcgataatg ccaagaacac      300
tctctacttg cagatgaatt ccctttcgagc cgaggataca gcggtgtact actgcgccag     360
tctgtactac gactatgggg acgcaatgga ctattgggga caaggcacac tggtgactgt     420
tagctccgcg tcgaccaagg gcccatcggt cttccccctg caccctcct caagagcac      480 ctctgggggc acagcggccc tgggctgcct ggtcaaggac tacttccccg aacctgtgac     540
ggtctcgtgg aactcaggcg ccctgaccag cggcgtgcac accttcccgg ctgtcctaca     600
gtcctcagga ctctactccc tcagcagcgt ggtgaccgtg ccctccagca gcttgggcac     660
ccagacctac atctgcaacg tgaatcacaa gcccagcaac accaaggtgg acaagagagt     720
tgagcccaaa tcttgtgaca aaactcacac atgcccaccg tgcccagcac ctgaactcct     780
ggggggaccg tcagtcttcc tcttcccccc aaaacccaag gacaccctca tgatctcccg     840 gaccctgag gtcacatgcg tggtggtgga cgtgagccac gaagaccctg aggtcaagtt     900
caactggtac gtggacggcg tggaggtgca taatgccaag acaaagccgc gggaggagca     960
gtacaacagc acgtaccgtg tggtcagcgt cctcaccgtc ctgcaccagg actggctgaa    1020
tggcaaggag tacaagtgca aggtctccaa caaagccctc ccagccccca tcgagaaaac    1080
catctccaaa gccaagggc agccccgaga accacaggtg tacaccctgc ccccatcccg    1140
ggaggagatg accaagaacc aggtcagcct gacctgcctg gtcaaaggct tctatcccag    1200
cgacatcgcc gtggagtggg agagcaatgg gcagccggag aacaactaca agaccacgcc    1260
tcccgtgctg gactccgacg gctccttctt cctctatagc aagctcaccg tggacaagag    1320
caggtggcag caggggaacg tcttctcatg ctccgtgatg catgaggctc tgcacaacca    1380
ctacacgcag aagagcctct ccctgtcccc gggtaaatga gtgcgacggc cgggcggcgg    1440
```

<210> SEQ ID NO 33
<211> LENGTH: 1450
<212> TYPE: DNA
<213> ORGANISM: Artificial Sequence
<220> FEATURE:
<223> OTHER INFORMATION: Synthetic coding sequence

<400> SEQUENCE: 33

```
gaattccacc atgggatggt catgtatcat ccttttttcta gtagcaactg caaccggtgt      60
ccacagtgaa gtgcagctgg tcgaatctgg aggaggcctg gttcagcctg gtggcagcct     120
taggctctct tgtgcagcct ctggctttac cttctcacgg tattggttca gctgggtgag     180
acaggctcca gggaaaggtc tggtgtgggt aggggagata acccccagca gcagcacgat     240
caactatgct ccgtcactga agacaagtt caccatttcc cgcgataatg ccaagaacac       300
tctctacttg cagatgaatt cccttcgagc cgaggataca gcggtgtact actgcgccag     360
tctgtactac gactatgggg acgcatacga ctattgggga caaggcacac tggtgactgt    420
tagctccgcg tcgaccaagg gcccatcggt cttccccctg gcaccctcct ccaagagcac    480
ctctggggggc acagcggccc tgggctgcct ggtcaaggac tacttccccg aacctgtgac  540
ggtctcgtgg aactcaggcg ccctgaccag cggcgtgcac accttcccgg ctgtcctaca    600
gtcctcagga ctctactccc tcagcagcgt ggtgaccgtg ccctccagca gcttgggcac    660
ccagacctac atctgcaacg tgaatcacaa gcccagcaac accaaggtgg acaagagagt   720
tgagcccaaa tcttgtgaca aaactcacac atgcccaccg tgcccagcac ctgaactcct    780
ggggggaccg tcagtcttcc tcttcccccc aaaacccaag gacaccctca tgatctcccg  840
gacccctgag gtcacatgcg tggtggtgga cgtgagccac gaagaccctg aggtcaagtt   900
caactggtac gtggacggcg tggaggtgca taatgccaag acaaagccgc gggaggagca  960
gtacaacagc acgtaccgtg tggtcagcgt cctcaccgtc ctgcaccagg actggctgaa  1020
tggcaaggag tacaagtgca aggtctccaa caaagccctc ccagccccca tcgagaaaac  1080
catctccaaa gccaagggc agccccgaga accacaggtg tacaccctgc ccccatcccg     1140
ggaggagatg accaagaacc aggtcagcct gacctgcctg gtcaaaggct tctatcccag   1200
cgacatcgcc gtggagtggg agagcaatgg gcagccggag aacaactaca agaccacgcc  1260
tcccgtgctg gactccgacg gctccttctt cctctatagc aagctcaccg tggacaagag  1320
caggtggcag caggggaacg tcttctcatg ctccgtgatg catgaggctc tgcacaacca  1380
ctacacgcag aagagcctct ccctgtcccc gggtaaatga gtgcgacggc cggcggcgg   1440
cggcggatcc                                                                     1450
```

<210> SEQ ID NO 34
<211> LENGTH: 1450
<212> TYPE: DNA
<213> ORGANISM: Artificial Sequence
<220> FEATURE:
<223> OTHER INFORMATION: Synthetic coding sequence

<400> SEQUENCE: 34

```
gaattccacc atgggatggt catgtatcat ccttttttcta gtagcaactg caaccggtgt      60
ccacagtgaa gtgcagctgg tcgaatctgg aggaggcctg gttcagcctg gtggcagcct     120
taggctctct tgtgcagcct ctggctttac cttctcacgg tattggatca gctgggtgag    180
```

```
acaggctcca gggaaaggtc tggtgtgggt aggggagata aaccccagca gcagcacgat      240
caactatgct ccgtcactga aagacaagtt caccatttcc cgcgataatg ccaagaacac      300
tctctacttg cagatgaatt cccttcgagc cgaggataca gcggtgtact actgcgccag      360
tctgtactac gactatgggg acgcatacga ctattgggga caaggcacac tggtgactgt      420
tagctccgcg tcgaccaagg gcccatcggt cttccccctg caccctcct ccaagagcac       480 ctctgggggc acagcggccc tgggctgcct ggtcaaggac tacttccccg aacctgtgac      540
ggtctcgtgg aactcaggcg ccctgaccag cggcgtgcac accttccgg ctgtcctaca       600 gtcctcagga ctctactccc tcagcagcgt ggtgaccgtg ccctccagca gcttgggcac      660
ccagacctac atctgcaacg tgaatcacaa gcccagcaac accaaggtgg acaagagagt      720
tgagcccaaa tcttgtgaca aaactcacac atgcccaccg tgcccagcac ctgaactcct      780 gggggaccg tcagtcttcc tcttcccccc aaaacccaag gacaccctca tgatctcccg        840
gacccctgag gtcacatgcg tggtggtgga cgtgagccac gaagaccctg aggtcaagtt      900
caactggtac gtggacggcg tggaggtgca taatgccaag acaaagccgc gggaggagca      960
gtacaacagc acgtaccgtg tggtcagcgt cctcaccgtc ctgcaccagg actggctgaa     1020
tggcaaggag tacaagtgca aggtctccaa caaagccctc ccagccccca tcgagaaaac     1080
catctccaaa gccaaagggc agccccgaga accacaggtg tacaccctgc ccccatcccg     1140
ggaggagatg accaagaacc aggtcagcct gacctgcctg gtcaaaggct tctatcccag     1200
cgacatcgcc gtggagtggg agagcaatgg gcagccggag aacaactaca agaccacgcc     1260
tcccgtgctg gactccgacg gctccttctt cctctatagc aagctcaccg tggacaagag     1320
caggtggcag caggggaacg tcttctcatg ctccgtgatg catgaggctc tgcacaacca     1380
ctacacgcag aagagcctct ccctgtcccc gggtaaatga gtgcgacggc cgggcggcgg     1440
cggcggatcc                                                           1450
```

<210> SEQ ID NO 35
<211> LENGTH: 718
<212> TYPE: DNA
<213> ORGANISM: Artificial Sequence
<220> FEATURE:
<223> OTHER INFORMATION: Synthetic coding sequence

<400> SEQUENCE: 35

```
gaattccacc atgggatggt catgtatcat cctttttcta gtagcaactg caaccggtgt       60
acactccgag atcgtgatga cccagtctcc tgctaccctg agcgtttctc ccggtgaaag      120
ggccacactc agctgcaaag cctctcaaag cgtggacagc aatgtcgcct ggtatcagca      180
gaaacctggc caagctccga gagcactgat ctattccgcg tcattgcgct tttccggcat      240
accagcacgg tttagtggct cagggagtgg gactgagttc actctgacga ttagctccct      300
tcagtcagag gatttcgccg tgtactactg tcagcagtac aacaactatc ccctcacatt      360
cggagctgga accaagctgg aactgaagcg tacggtggct gcaccatctg tcttcatctt      420
cccgccatct gatgagcagt tgaaatctgg aactgcctct gttgtgtgcc tgctgaataa      480
cttctatccc agagaggcca agtacagtg gaaggtggat aacgccctcc aatcgggtaa      540
ctcccaggag agtgtcacag agcaggacag caaggacagc acctacagcc tcagcagcac      600
cctgacgctg agcaaagcag actacgagaa acacaaagtc tacgcctgcg aagtcaccca      660
tcagggcctg agctcgcccg tcacaaagag cttcaacagg ggagagtgtt agggatcc         718
```

```
<210> SEQ ID NO 36
<211> LENGTH: 718
<212> TYPE: DNA
<213> ORGANISM: Artificial Sequence
<220> FEATURE:
<223> OTHER INFORMATION: Synthetic coding sequence

<400> SEQUENCE: 36
gaattccacc atgggatggt catgtatcat ccttttttcta gtagcaactg caaccggtgt      60
acactccgag atcgtgatga cccagtctcc tgctaccctg agcgtttctc cggtgaaag      120 ggccacactc agctgcaaag cctctcaaag cgtggagagc aatgtcgcct ggtatcagca     180
gaaacctggc caagtccgag agcactgat ctattccgcg tcattgcgct tttccggcat      240
accagcacgg tttagtggct cagggagtgg gactgagttc actctgacga ttagctccct     300
tcagtcagag gatttcgccg tgtactactg tcagcagtac aacaactatc ccctcacatt     360
cggagctgga accaagctgg aactgaagcg tacggtggct gcaccatctg tcttcatctt     420
cccgccatct gatgagcagt tgaaatctgg aactgcctct gttgtgtgcc tgctgaataa     480
cttctatccc agagaggcca agtacagtg aaggtggat aacgccctcc aatcgggtaa       540
ctcccaggag agtgtcacag agcaggacag caaggacagc acctacagcc tcagcagcac     600
cctgacgctg agcaaagcag actacgagaa acacaaagtc tacgcctgcg aagtcaccca     660
tcagggcctg agctcgcccg tcacaaagag cttcaacagg ggagagtgtt agggatcc       718

<210> SEQ ID NO 37
<211> LENGTH: 285
<212> TYPE: PRT
<213> ORGANISM: Artificial Sequence
<220> FEATURE:
<223> OTHER INFORMATION: Synthetic peptide

<400> SEQUENCE: 37

Met Ser Pro Ile Leu Gly Tyr Trp Lys Ile Lys Gly Leu Val Gln Pro
1               5                   10                  15

Thr Arg Leu Leu Leu Glu Tyr Leu Glu Glu Lys Tyr Glu Glu His Leu
            20                  25                  30

Tyr Glu Arg Asp Glu Gly Asp Lys Trp Arg Asn Lys Lys Phe Glu Leu
        35                  40                  45

Gly Leu Glu Phe Pro Asn Leu Pro Tyr Tyr Ile Asp Gly Asp Val Lys
    50                  55                  60

Leu Thr Gln Ser Met Ala Ile Ile Arg Tyr Ile Ala Asp Lys His Asn
65                  70                  75                  80

Met Leu Gly Gly Cys Pro Lys Glu Arg Ala Glu Ile Ser Met Leu Glu
                85                  90                  95

Gly Ala Val Leu Asp Ile Arg Tyr Gly Val Ser Arg Ile Ala Tyr Ser
            100                 105                 110

Lys Asp Phe Glu Thr Leu Lys Val Asp Phe Leu Ser Lys Leu Pro Glu
        115                 120                 125

Met Leu Lys Met Phe Glu Asp Arg Leu Cys His Lys Thr Tyr Leu Asn
    130                 135                 140

Gly Asp His Val Thr His Pro Asp Phe Met Leu Tyr Asp Ala Leu Asp
145                 150                 155                 160

Val Val Leu Tyr Met Asp Pro Met Cys Leu Asp Ala Phe Pro Lys Leu
                165                 170                 175

Val Cys Phe Lys Lys Arg Ile Glu Ala Ile Pro Gln Ile Asp Lys Tyr
            180                 185                 190
```

```
Leu Lys Ser Ser Lys Tyr Ile Ala Trp Pro Leu Gln Gly Trp Gln Ala
            195                 200                 205

Thr Phe Gly Gly Gly Asp His Pro Pro Lys Ser Asp Leu Val Pro Arg
        210                 215                 220

Gly Ser Met Ala Gly Gln Cys Ser Gln Asn Glu Tyr Phe Asp Ser Leu
225                 230                 235                 240

Leu His Ala Cys Ile Pro Cys Gln Leu Arg Cys Ser Ser Asn Thr Pro
                245                 250                 255

Pro Leu Thr Cys Gln Arg Tyr Cys Asn Ala Ser Val Thr Asn Ser Val
            260                 265                 270

Lys Gly Thr Asn Ala Leu Glu His His His His His His
            275                 280                 285
```

<210> SEQ ID NO 38
<211> LENGTH: 53
<212> TYPE: PRT
<213> ORGANISM: Artificial Sequence
<220> FEATURE:
<223> OTHER INFORMATION: Synthetic peptide

<400> SEQUENCE: 38

```
Met Ala Gly Gln Cys Ser Gln Asn Glu Tyr Phe Asp Ser Leu Leu His
1               5                   10                  15

Ala Cys Ile Pro Cys Gln Leu Arg Cys Ser Ser Asn Thr Pro Pro Leu
            20                  25                  30

Thr Cys Gln Arg Tyr Cys Asn Ala Ser Val Thr Asn Ser Val Lys Gly
        35                  40                  45

Thr Asn Ala Leu Glu
    50
```

<210> SEQ ID NO 39
<211> LENGTH: 56
<212> TYPE: PRT
<213> ORGANISM: Homo sapiens

<400> SEQUENCE: 39

```
Met Leu Gln Met Ala Gly Gln Cys Ser Gln Asn Glu Tyr Phe Asp Ser
1               5                   10                  15

Leu Leu His Ala Cys Ile Pro Cys Gln Leu Arg Cys Ser Ser Asn Thr
            20                  25                  30

Pro Pro Leu Thr Cys Gln Arg Tyr Cys Asn Ala Ser Val Thr Asn Ser
        35                  40                  45

Val Lys Gly Thr Asn Ala Leu Glu
    50                  55
```

<210> SEQ ID NO 40
<211> LENGTH: 20
<212> TYPE: PRT
<213> ORGANISM: Homo sapiens

<400> SEQUENCE: 40

```
Tyr Phe Asp Ser Leu Leu His Ala Cys Ile Pro Cys Gln Leu Arg Cys
1               5                   10                  15

Ser Ser Asn Thr
            20
```

<210> SEQ ID NO 41
<211> LENGTH: 120
<212> TYPE: PRT
<213> ORGANISM: Artificial Sequence

```
<220> FEATURE:
<223> OTHER INFORMATION: Synthetic peptide
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (5)..(6)
<223> OTHER INFORMATION: Xaa can be any naturally occurring amino acid
<220> FEATURE:
<221> NAME/KEY: misc_feature
<222> LOCATION: (19)..(19)
<223> OTHER INFORMATION: Xaa can be any naturally occurring amino acid
<220> FEATURE:
<221> NAME/KEY: misc_feature
<222> LOCATION: (27)..(28)
<223> OTHER INFORMATION: Xaa can be any naturally occurring amino acid
<220> FEATURE:
<221> NAME/KEY: misc_feature
<222> LOCATION: (30)..(31)
<223> OTHER INFORMATION: Xaa can be any naturally occurring amino acid
<220> FEATURE:
<221> NAME/KEY: misc_feature
<222> LOCATION: (39)..(39)
<223> OTHER INFORMATION: Xaa can be any naturally occurring amino acid
<220> FEATURE:
<221> NAME/KEY: misc_feature
<222> LOCATION: (48)..(48)
<223> OTHER INFORMATION: Xaa can be any naturally occurring amino acid
<220> FEATURE:
<221> NAME/KEY: misc_feature
<222> LOCATION: (66)..(67)
<223> OTHER INFORMATION: Xaa can be any naturally occurring amino acid
<220> FEATURE:
<221> NAME/KEY: misc_feature
<222> LOCATION: (69)..(69)
<223> OTHER INFORMATION: Xaa can be any naturally occurring amino acid
<220> FEATURE:
<221> NAME/KEY: misc_feature
<222> LOCATION: (84)..(86)
<223> OTHER INFORMATION: Xaa can be any naturally occurring amino acid
<220> FEATURE:
<221> NAME/KEY: misc_feature
<222> LOCATION: (88)..(88)
<223> OTHER INFORMATION: Xaa can be any naturally occurring amino acid
<220> FEATURE:
<221> NAME/KEY: misc_feature
<222> LOCATION: (93)..(93)
<223> OTHER INFORMATION: Xaa can be any naturally occurring amino acid
<220> FEATURE:
<221> NAME/KEY: misc_feature
<222> LOCATION: (115)..(115)
<223> OTHER INFORMATION: Xaa can be any naturally occurring amino acid

<400> SEQUENCE: 41

Xaa Val Gln Leu Xaa Xaa Ser Gly Gly Gly Leu Val Gln Pro Gly Gly
1               5                   10                  15

Ser Leu Xaa Leu Ser Cys Ala Ala Ser Gly Xaa Xaa Phe Xaa Xaa Tyr
            20                  25                  30

Trp Glx Ser Trp Val Arg Xaa Ala Pro Gly Lys Gly Leu Glu Trp Xaa
        35                  40                  45

Gly Glu Ile Asn Pro Glx Ser Ser Thr Ile Asn Tyr Ala Pro Ser Leu
    50                  55                  60

Lys Xaa Xaa Phe Xaa Ile Ser Arg Asp Asn Ala Lys Asn Thr Leu Tyr
65                  70                  75                  80

Leu Gln Met Xaa Xaa Xaa Arg Xaa Glu Asp Thr Ala Xaa Tyr Tyr Cys
                85                  90                  95

Ala Ser Leu Tyr Tyr Asp Tyr Gly Asp Ala Glx Asp Tyr Trp Gly Gln
            100                 105                 110

Gly Thr Xaa Val Thr Val Ser Ser
```

<210> SEQ ID NO 42
<211> LENGTH: 108
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (8)..(13)
<223> OTHER INFORMATION: Xaa can be any naturally occurring amino acid
<220> FEATURE:
<221> NAME/KEY: misc_feature
<222> LOCATION: (18)..(18)
<223> OTHER INFORMATION: Xaa can be any naturally occurring amino acid
<220> FEATURE:
<221> NAME/KEY: misc_feature
<222> LOCATION: (20)..(21)
<223> OTHER INFORMATION: Xaa can be any naturally occurring amino acid
<220> FEATURE:
<221> NAME/KEY: misc_feature
<222> LOCATION: (41)..(41)
<223> OTHER INFORMATION: Xaa can be any naturally occurring amino acid
<220> FEATURE:
<221> NAME/KEY: misc_feature
<222> LOCATION: (43)..(43)
<223> OTHER INFORMATION: Xaa can be any naturally occurring amino acid
<220> FEATURE:
<221> NAME/KEY: misc_feature
<222> LOCATION: (46)..(46)
<223> OTHER INFORMATION: Xaa can be any naturally occurring amino acid
<220> FEATURE:
<221> NAME/KEY: misc_feature
<222> LOCATION: (49)..(49)
<223> OTHER INFORMATION: Xaa can be any naturally occurring amino acid
<220> FEATURE:
<221> NAME/KEY: misc_feature
<222> LOCATION: (51)..(52)
<223> OTHER INFORMATION: Xaa can be any naturally occurring amino acid
<220> FEATURE:
<221> NAME/KEY: misc_feature
<222> LOCATION: (63)..(63)
<223> OTHER INFORMATION: Xaa can be any naturally occurring amino acid
<220> FEATURE:
<221> NAME/KEY: misc_feature
<222> LOCATION: (77)..(77)
<223> OTHER INFORMATION: Xaa can be any naturally occurring amino acid
<220> FEATURE:
<221> NAME/KEY: misc_feature
<222> LOCATION: (83)..(83)
<223> OTHER INFORMATION: Xaa can be any naturally occurring amino acid
<220> FEATURE:
<221> NAME/KEY: misc_feature
<222> LOCATION: (85)..(85)
<223> OTHER INFORMATION: Xaa can be any naturally occurring amino acid
<220> FEATURE:
<221> NAME/KEY: misc_feature
<222> LOCATION: (87)..(87)
<223> OTHER INFORMATION: Xaa can be any naturally occurring amino acid

<400> SEQUENCE: 42

Xaa Ile Val Met Thr Gln Ser Xaa Xaa Xaa Xaa Xaa Xaa Ser Val Gly
1               5                   10                  15

Asp Xaa Val Xaa Xaa Thr Cys Lys Ala Ser Gln Ser Val Glu Ser Asn
            20                  25                  30

Val Ala Trp Tyr Gln Gln Lys Pro Xaa Gln Xaa Pro Lys Xaa Leu Ile
        35                  40                  45

Xaa Ser Xaa Xaa Leu Arg Phe Ser Gly Val Pro Ala Arg Phe Xaa Gly
50                  55                  60

```
Ser Gly Ser Gly Thr Asp Phe Thr Leu Thr Ile Ser Xaa Leu Gln Ser
 65                  70                  75                  80

Glu Asp Xaa Ala Xaa Tyr Xaa Cys Gln Gln Tyr Asn Asn Tyr Pro Leu
                 85                  90                  95

Thr Phe Gly Ala Gly Thr Lys Leu Glu Leu Lys Arg
                100                 105

<210> SEQ ID NO 43
<211> LENGTH: 108
<212> TYPE: PRT
<213> ORGANISM: Artificial Sequence
<220> FEATURE:
<223> OTHER INFORMATION: Synthetic peptide

<400> SEQUENCE: 43

Asp Ile Val Met Thr Gln Ser Gln Arg Phe Met Thr Thr Ser Val Gly
 1               5                  10                  15

Asp Arg Val Ser Val Thr Cys Lys Ala Ser Gln Ser Val Asp Ser Asn
                 20                  25                  30

Val Ala Trp Tyr Gln Gln Lys Pro Arg Gln Ser Pro Lys Ala Leu Ile
             35                  40                  45

Phe Ser Ala Ser Leu Arg Phe Ser Gly Val Pro Ala Arg Phe Thr Gly
 50                  55                  60

Ser Gly Ser Gly Thr Asp Phe Thr Leu Thr Ile Ser Asn Leu Gln Ser
 65                  70                  75                  80

Glu Asp Leu Ala Glu Tyr Phe Cys Gln Gln Tyr Asn Asn Tyr Pro Leu
                 85                  90                  95

Thr Phe Gly Ala Gly Thr Lys Leu Glu Leu Lys Arg
                100                 105
```